United States Patent
Bowers et al.

(10) Patent No.: US 9,589,107 B2
(45) Date of Patent: Mar. 7, 2017

(54) MONITORING TREATMENT COMPLIANCE USING SPEECH PATTERNS PASSIVELY CAPTURED FROM A PATIENT ENVIRONMENT

(71) Applicant: Elwha LLC, Bellevue, WA (US)

(72) Inventors: Jeffrey A. Bowers, Bellevue, WA (US); Paul Duesterhoft, Grapevine, TX (US); Daniel Hawkins, Pleasanton, CA (US); Roderick A. Hyde, Redmond, WA (US); Edward K. Y. Jung, Bellevue, WA (US); Jordin T. Kare, Seattle, WA (US); Eric C. Leuthardt, St. Louis, MO (US); Nathan P. Myhrvold, Medina, WA (US); Michael A. Smith, Phoenix, AZ (US); Elizabeth A. Sweeney, Seattle, WA (US); Clarence T. Tegreene, Mercer Island, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 153 days.

(21) Appl. No.: 14/543,030

(22) Filed: Nov. 17, 2014

(65) Prior Publication Data
US 2016/0140321 A1    May 19, 2016

(51) Int. Cl.
*G10L 15/00* (2013.01)
*G06F 19/00* (2011.01)
(Continued)

(52) U.S. Cl.
CPC ........ *G06F 19/3487* (2013.01); *A61B 5/4803* (2013.01); *A61B 5/4833* (2013.01);
(Continued)

(58) Field of Classification Search
USPC .................................. 704/231–257, 270–275
See application file for complete search history.

(56) References Cited

U.S. PATENT DOCUMENTS 4,360,708 A   11/1982 Taguchi et al.
4,455,676 A    6/1984 Kaneda
(Continued)

FOREIGN PATENT DOCUMENTS

WO   WO 2008/143908 A2    11/2008

OTHER PUBLICATIONS

Aleksic et al.; "Audio-Visual Biometrics"; Proceedings of the IEEE; Nov. 2006; pp. 2025-2044; vol. 94, No. 11; IEEE.
(Continued)

*Primary Examiner* — Jesse Pullias

(57) ABSTRACT

Methods and systems are described for monitoring patient speech to determine compliance of the patient with a prescribed regimen for treating for a brain-related disorder. Patient speech is detected with an audio sensor at the patient location, and speech data is transmitted to a monitoring location. Patient speech is processed at the patient location and/or monitoring location to identify speech parameters and/or patterns that indicate whether the patient has complied with the prescribed treatment regimen. Patient identity may be determined through biometric identification or other authentication techniques. The system may provide a report to an interested party, for example a medical care provider, based on whether (and/or the extent to which) the patient has complied with the prescribed treatment regimen. The monitoring system may transmit a report to a wireless device such as a pager or cell phone, generate an alarm or notification, and/or store information for later use.

51 Claims, 34 Drawing Sheets

(51) Int. Cl.
*A61B 5/00* (2006.01)
*G06Q 50/24* (2012.01)
*A61B 5/16* (2006.01)

(52) U.S. Cl.
CPC ............ *G06F 19/363* (2013.01); *G06Q 50/24* (2013.01); *A61B 5/16* (2013.01)

(56) References Cited

U.S. PATENT DOCUMENTS

| | | | |
|---|---|---|---|
| 4,641,349 A | 2/1987 | Flom et al. | |
| 5,572,596 A | 11/1996 | Wildes et al. | |
| 5,913,310 A | 6/1999 | Brown | |
| 6,006,188 A | 12/1999 | Bogdashevsky et al. | |
| 6,014,626 A * | 1/2000 | Cohen | G06F 19/3418 704/271 |
| 6,162,186 A | 12/2000 | Scinto et al. | |
| 6,186,145 B1 | 2/2001 | Brown | |
| 6,231,344 B1 | 5/2001 | Merzenich et al. | |
| 6,558,321 B1 * | 5/2003 | Burd | A61B 5/0022 600/300 |
| 7,315,725 B2 | 1/2008 | Sachs et al. | |
| 7,330,566 B2 | 2/2008 | Cutler | |
| 7,378,954 B2 | 5/2008 | Wendt | |
| 7,451,079 B2 | 11/2008 | Oudeyer | |
| 7,616,779 B2 | 11/2009 | Liao et al. | |
| 7,728,839 B2 | 6/2010 | Yang et al. | |
| 7,794,934 B2 | 9/2010 | Martucci et al. | |
| 7,843,356 B2 | 11/2010 | Webb | |
| 8,032,399 B2 | 10/2011 | Brown | |
| 8,229,178 B2 | 7/2012 | Zhang et al. | |
| 8,396,283 B2 | 3/2013 | Iihoshi et al. | |
| 8,494,857 B2 | 7/2013 | Pakhomov | |
| 8,631,063 B2 | 1/2014 | Helal et al. | |
| 8,667,112 B2 | 3/2014 | Roth et al. | |
| 8,808,195 B2 | 8/2014 | Tseng et al. | |
| 8,996,392 B2 | 3/2015 | Cashman et al. | |
| 9,113,795 B2 | 8/2015 | Hong et al. | |
| 9,135,403 B1 | 9/2015 | Tolmosoff | |
| 2002/0138302 A1 * | 9/2002 | Bodnick | G06F 19/323 705/2 |
| 2002/0169635 A1 | 11/2002 | Shillingburg | |
| 2002/0193990 A1 | 12/2002 | Komatsu | |
| 2003/0125610 A1 | 7/2003 | Sachs et al. | |
| 2004/0054266 A1 | 3/2004 | Covington | |
| 2004/0167774 A1 | 8/2004 | Shrivastav | |
| 2004/0197750 A1 | 10/2004 | Donaher et al. | |
| 2005/0084832 A1 | 4/2005 | Janssen et al. | |
| 2005/0273017 A1 | 12/2005 | Gordon | |
| 2006/0028556 A1 | 2/2006 | Bunn et al. | |
| 2006/0190419 A1 | 8/2006 | Bunn et al. | |
| 2007/0241261 A1 | 10/2007 | Wendt | |
| 2008/0039698 A1 | 2/2008 | Burton | |
| 2008/0242949 A1 | 10/2008 | Jung et al. | |
| 2008/0287821 A1 | 11/2008 | Jung et al. | |
| 2008/0294019 A1 | 11/2008 | Tran | |
| 2008/0312958 A1 | 12/2008 | Sachs et al. | |
| 2009/0005653 A1 | 1/2009 | Jung et al. | |
| 2009/0099848 A1 | 4/2009 | Lerner et al. | |
| 2009/0149769 A1 | 6/2009 | Pettigrew | |
| 2009/0149898 A1 | 6/2009 | Hulvershorn et al. | |
| 2009/0202966 A1 | 8/2009 | Teicher et al. | |
| 2009/0264789 A1 | 10/2009 | Molnar et al. | |
| 2009/0270786 A1 | 10/2009 | Hyde et al. | |
| 2009/0271008 A1 | 10/2009 | Hyde et al. | |
| 2010/0076249 A1 | 3/2010 | Leuthardt et al. | |
| 2010/0174533 A1 | 7/2010 | Pakhomov | |
| 2010/0211005 A1 | 8/2010 | Edwards et al. | |
| 2010/0217100 A1 | 8/2010 | LeBoeuf et al. | |
| 2010/0274577 A1 | 10/2010 | Firminger et al. | |
| 2010/0312579 A1 | 12/2010 | Firminger et al. | |
| 2011/0224912 A1 * | 9/2011 | Bhavaraju | G06F 19/3456 702/19 |
| 2012/0116186 A1 | 5/2012 | Shrivastav et al. | |
| 2013/0046477 A1 | 2/2013 | Hyde et al. | |
| 2013/0085758 A1 | 4/2013 | Csoma et al. | |
| 2013/0110511 A1 | 5/2013 | Spiegel et al. | |
| 2013/0179188 A1 | 7/2013 | Hyde et al. | |
| 2013/0253291 A1 | 9/2013 | Dixon et al. | |
| 2013/0254287 A1 | 9/2013 | Biswas et al. | |

OTHER PUBLICATIONS

Chandra et al.; "A review on Speech and Speaker Authentication System using Voice Signal feature selection and extraction"; 2009 IEEE International Advance Computing Conference (IACC 2009); Mar. 6-7, 2009; pp. 1341-1346; IEEE.

Covington et al.; "Schizophrenia and the structure of language: The linguist's view"; Schizophrenia Research; bearing dates of Dec. 10, 2004 and 2005; pp. 85-98; vol. 77; Elsevier B.V.

Coxworth, Ben; "Bipolar disorder app predicts mood swings by eavesdropping on phone conversations"; Gizmag; May 12, 2014; pp. 1-5; located at http://www.gizmag.com/priori-bipolar-disorder-voice-app/32023/.

Essig, Todd; "How Is Your Mood Today? Hey, There's an App for That"; Forbes; May 15, 2014; pp. 1-4; located at http://www.forbes.com/sites/toddessig/2014/05/15/how-is-your-mood-today-hey-theres-an-app-for-that/.

Gaba et al.; "Biometric Identification on the Basis of BPNN Classifier with Other Novel Techniques Used for Gait Analysis"; International Journal of Recent Technology and Engineering (IJRTE); Sep. 2013; pp. 137-142; vol. 2, Issue 4.

Gibin, Thomas; "Analysis of Gait of a Person for Individual Authentication"; European Journal of Academic Essays; 2014; pp. 33-38; vol. 1, No. 3.

Hancock et al.; "Hungry like the wolf: A word-pattern analysis of the language of psychopaths"; Legal and Criminological Psychology; 2011; pp. 1-13; The British Psychological Society.

Hollmer, Mark; "Smartphone app shows promise monitoring voice patterns to predict bipolar episodes"; Fierce Diagnostics; May 8, 2014; pp. 1-2; located at http://www.fiercediagnostics.com/node/2206/print.

Karam et al.; "Ecologically Valid Long-Term Mood Monitoring of Individuals With Bipolar Disorder Using Speech"; ICASSP; 2014; pp. 1-5; located at http://web.eecs.umich.edu/~emilykmp/EmilyPapers/Karam2014_ICASSP.pdf.

Kataria et al.; "A Survey of Automated Biometric Authentication Techniques"; 2013 Nirma University International Conference on Engineering (NUiCONE); 2013; pp. 1-6; IEEE.

Kuperberg et al.; "Language Dysfunction in Schizophrenia"; Chapter 19; Schiffer-7243F; Mar. 17, 2003; pp. 444-466; located at http://www.nmr.mgh.harvard.edu/kuperberglab/publications/chapters/Kuperberg&Caplan_Neurosych_2003.pdf.

Levy et al.; "The Genetic Basis of Thought Disorder and Language and Communication Disturbances in Schizophrenia"; J Neurolinguistics; May 1, 2010; pp. 1-23; vol. 23, No. 3; Elsevier Ltd.

McCowan et al.; "The Delta-Phase Spectrum With Application to Voice Activity Detection and Speaker Recognition"; IEEE Transactions on Audio, Speech, and Language Processing; Sep. 2011; pp. 2026-2038; vol. 19, No. 7; IEEE.

Nicholl et al.; "Neuropsychiatric Sequelae of Traumatic Brain Injury"; Semin Neurol.; 2009; pp. 247-255; vol. 29, No. 3.

Nixon et al.; "On Use of Biometrics in Forensics: Gait and Ear"; 18th European Signal Processing Conference (EUSIPCO-2010); Aug. 23-27, 2010; pp. 1655-1659; EURASIP.

Pell et al.; "On the Time Course of Vocal Emotion Recognition"; PLoS ONE; Nov. 2011; pp. 1-16; vol. 6, Issue 11, e27256.

physorg.com; "Speech monitoring could track Parkinson's"; Phys.org; Nov. 17, 2010; pp. 1-2; located http://phsy.org/news/2010-11-speech-track-parkinson.html.

Singer, Emily; "An App that Looks for Signs of Sickness"; MIT Technology Review; Jun. 21, 2011; pp. 1-2; located at http://www.technologyreview.com/news/424422/an-app-that-looks-for-signs-of-sickness/.

(56) References Cited

OTHER PUBLICATIONS

Strickland, Eliza; "Smartphone App Keeps Watch Over Schizophrenic Patients"; Spectrum.IEEE.org North American; Jul. 2014; pp. 1-2.
Tausczik et al.; "The Psychological Meaning of Words: LIWC and Computerized Text Analysis Methods"; Journal of Language and Social Psychology; 2010; pp. 24-54; vol. 29(I); Sage Publications.
Wheeler et al.; "Face Recognition at a Distance System for Surveillance Applications"; 2010 Fourth IEEE International Conference on Biometrics Compendium; Sep. 27-29, 2010; pp. 1-8; IEEE.
Whissell, Cynthia; "A comparison of two lists providing emotional norms for English words (ANEW and the DAL)"; Psychological Reports; 2008; pp. 597-600; vol. 102.
Yap et al.; "A Short Review of Methods for Face Detection and Multifractal Analysis"; 2009 International Conference on CyberWorlds; 2009; pp. 231-236; IEEE.
U.S. Appl. No. 14/543,066, Bowers et al.
U.S. Appl. No. 14/729,322, Bowers et al.
U.S. Appl. No. 14/729,278, Bowers et al.
biospace.com; "Measuring 'Moodtraces': New App Helps Monitor Depression"; Biospace.com; Feb. 27, 2015; pp. 1-2; located at http://www.biospace.com/news_print.aspx?NewsEntityId=366575.
U.S. Appl. No. 14/939,143, Bowers et al.
U.S. Appl. No. 14/939,013, Bowers et al.
U.S. Appl. No. 14/938,973, Bowers et al.
U.S. Appl. No. 14/938,940, Bowers et al.
Bleichner et al.; "Exploring miniaturized EEG electrodes for brain-computer interfaces. An EEG you do not see?"; Physiological Reports; 2015; pp. 1-9; vol. 3, Iss. 4, e12362; Wiley Periodicals, Inc.
Delorme et al.; "EEGLAB: an open source toolbox for analysis of single-trial EEG dynamics including independent component analysis"; Journal of Neuroscience Methods; 2004; pp. 1-14; vol. 134.
"faceLAB 5 Specifications"; Seeing Machines; 2012; pp. 1.
Fotiou et al.; "Pupil reaction to light in Alzheimer's disease: evaluation of pupil size changes and mobility"; Aging Clin Exp Res; Oct. 2007; pp. 364-371; vol. 19, No. 5 (abstract only).
Hansenne, Michel; "Event-Related Brain Potentials in Psychopathology: Clinical and Cognitive Perspectives"; Psychologica Belgica; 2006; pp. 5-36, vol. 46, Iss. 1-2.
Liao et al.; "Biosensor Technologies for Augmented Brain-Computer Interfaces in the Next Decades"; Proceedings of the IEEE; May 13, 2012; pp. 1553-1566; vol. 100; IEEE.
Lin et al.; "Assessing the feasibility of online SSVEP decoding in human walking using a consumer EEG headset"; Journal of NeuroEngineering and Rehabilitation; 2014; pp. 1-8; vol. 11.
Sumiyoshi et al.; "Neural basis for the ability of atypical antipsychotic drugs to improve cognition in schizophrenia"; Frontiers in Behavioral Neuroscience; Oct. 2013; pp. 1-8; vol. 7, Article 140.
Wise et al.; "Event-related potential and autonomic signs of maladaptive information processing during an auditory oddball task in panic disorder"; International Journal of Psychophysiology; 2009; pp. 34-44; vol. 74; Elsevier B.V.
Woodman, Geoffrey F.; "A Brief Introduction to the Use of Event-Related Potentials (ERPs) in Studies of Perception and Attention"; Nov. 2010; pp. 1-28 plus five pages; located at http://www.ncbi.nlm.nih.gov/pmc/articles/PMC3816929/.
Zander et al.; "A dry EEG-system for scientific research and brain-computer interfaces"; Frontiers in Neuroscience; May 2011; pp. 1-10; vol. 5, Article 53.
PCT International Search Report; International App. No. PCT/US2015/060803; Feb. 24, 2016; pp. 1-3.
U.S. Appl. No. 14/400,462, Bowers at al.

\* cited by examiner

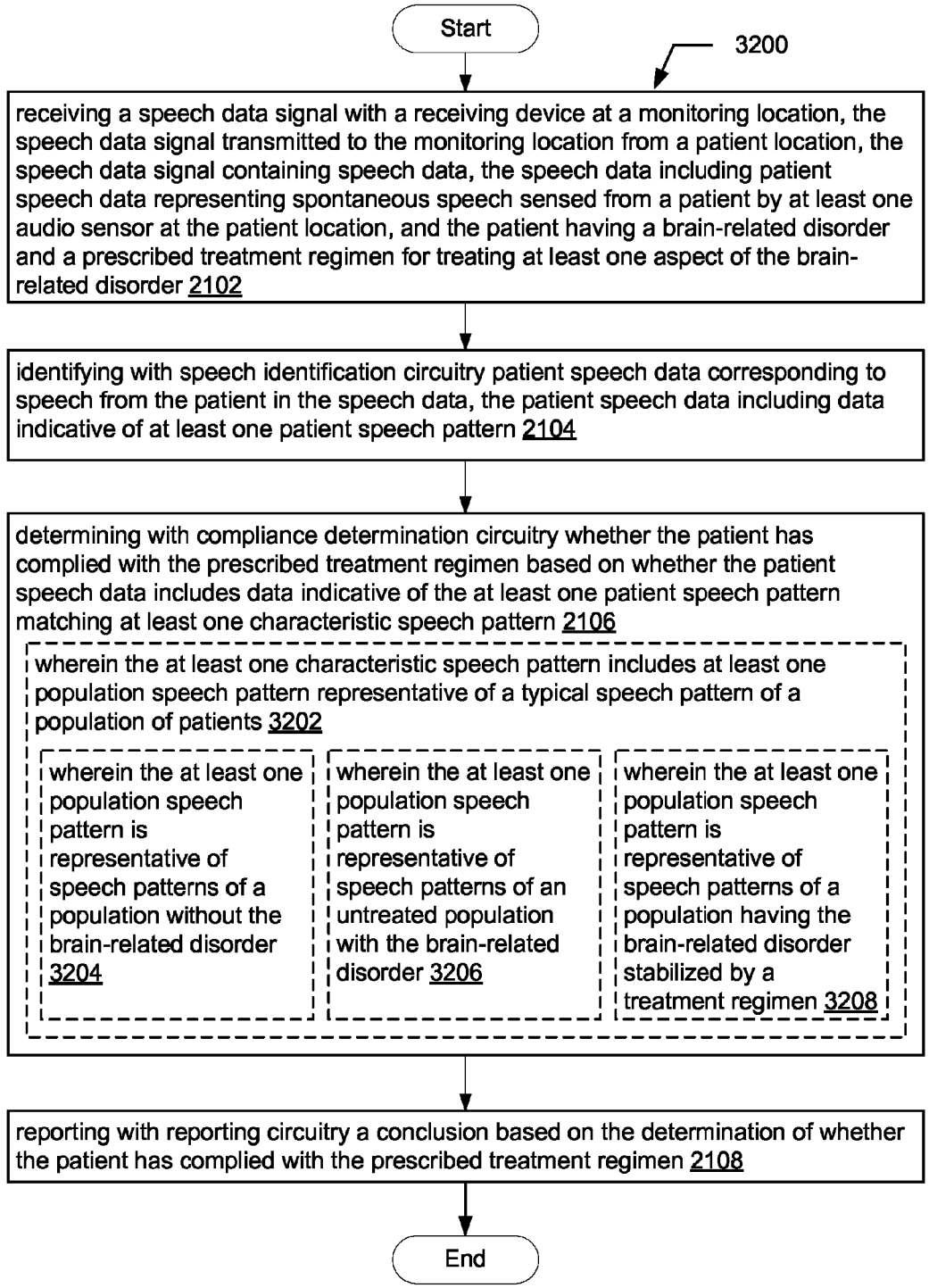

FIG. 33

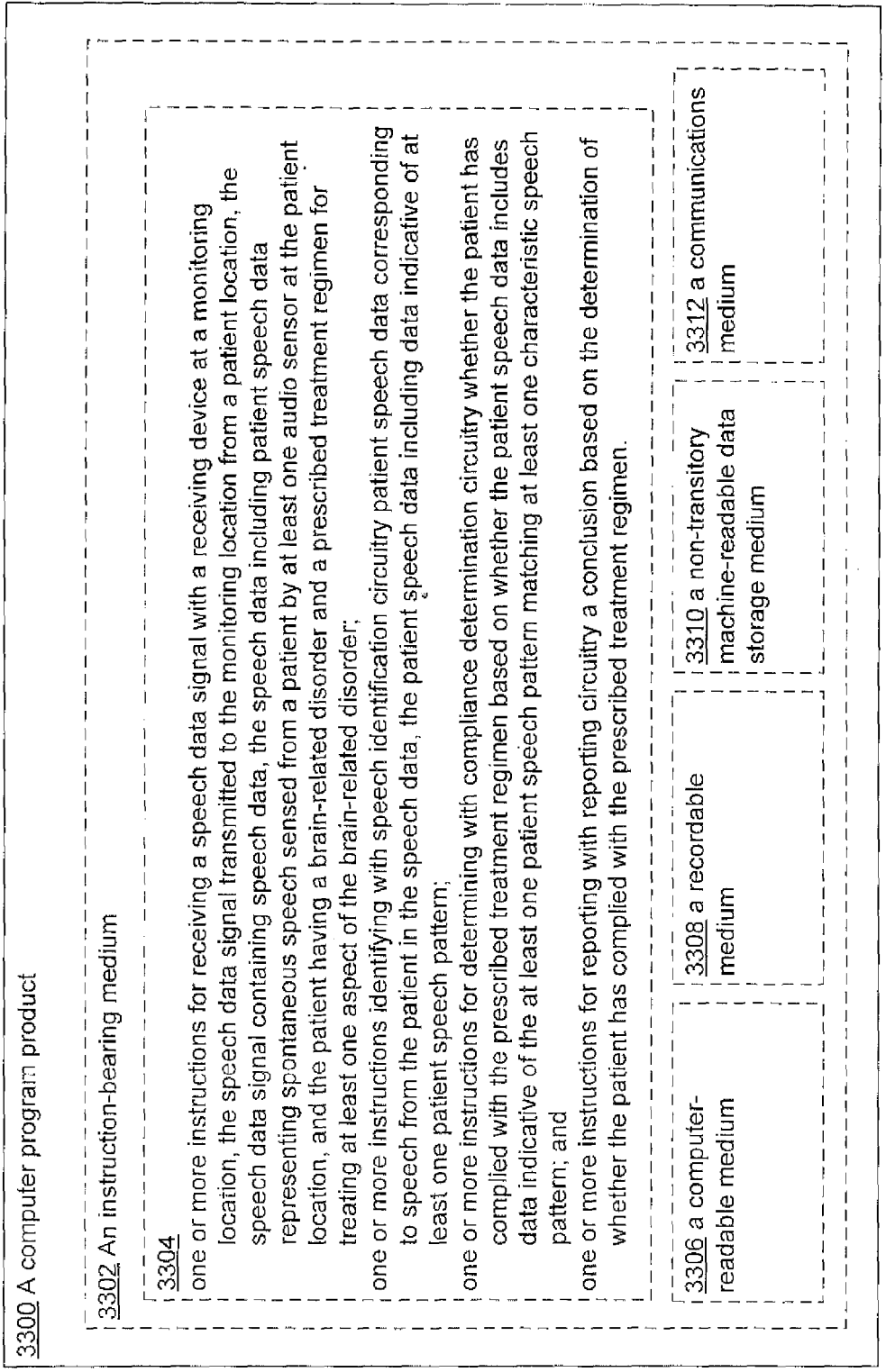

3300 A computer program product

3302 An instruction-bearing medium 3304
one or more instructions for receiving a speech data signal with a receiving device at a monitoring location, the speech data signal transmitted to the monitoring location from a patient location, the speech data signal containing speech data, the speech data including patient speech data representing spontaneous speech sensed from a patient by at least one audio sensor at the patient location, and the patient having a brain-related disorder and a prescribed treatment regimen for treating at least one aspect of the brain-related disorder;

one or more instructions identifying with speech identification circuitry patient speech data corresponding to speech from the patient in the speech data, the patient speech data including data indicative of at least one patient speech pattern;

one or more instructions for determining with compliance determination circuitry whether the patient has complied with the prescribed treatment regimen based on whether the patient speech data includes data indicative of the at least one patient speech pattern matching at least one characteristic speech pattern; and one or more instructions for reporting with reporting circuitry a conclusion based on the determination of whether the patient has complied with the prescribed treatment regimen.

3306 a computer-readable medium 3308 a recordable medium 3310 a non-transitory machine-readable data storage medium 3312 a communications medium

MONITORING TREATMENT COMPLIANCE USING SPEECH PATTERNS PASSIVELY CAPTURED FROM A PATIENT ENVIRONMENT If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)).

PRIORITY APPLICATIONS

None.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In an aspect, a system for monitoring compliance of a patient with a prescribed treatment regimen includes, but is not limited to, at least one receiving device for use at a monitoring location for receiving a speech data signal transmitted to the monitoring location from a patient location, the speech data signal containing speech data, the speech data including patient speech data representing spontaneous speech sensed from a patient with at least one audio sensor at the patient location, and the patient having a brain-related disorder and a prescribed treatment regimen for treating at least one aspect of the brain-related disorder; speech identification circuitry configured to identify the patient speech data corresponding to speech from the patient in the speech data, the patient speech data including data indicative of at least one patient speech pattern; compliance determination circuitry configured to determine compliance of the patient with the prescribed treatment regimen based on whether the patient speech data includes data indicative of the at least one patient speech pattern matching at least one characteristic speech pattern; and reporting circuitry configured to report a conclusion based on the determination of whether the patient has complied with the prescribed treatment regimen. In addition to the foregoing, other system aspects are described in the claims, drawings, and text forming a part of the disclosure set forth herein.

In an aspect, a method of monitoring compliance of a patient with a prescribed treatment regimen includes, but is not limited to, receiving a speech data signal with a receiving device at a monitoring location, the speech data signal transmitted to the monitoring location from a patient location, the speech data signal containing speech data, the speech data including patient speech data representing spontaneous speech sensed from a patient by at least one audio sensor at the patient location, and the patient having a brain-related disorder and a prescribed treatment regimen for treating at least one aspect of the brain-related disorder, identifying with speech identification circuitry patient speech data corresponding to speech from the patient in the speech data, the patient speech data including data indicative of at least one patient speech pattern, determining with compliance determination circuitry whether the patient has complied with the prescribed treatment regimen based on whether the patient speech data includes data indicative of the at least one patient speech pattern matching at least one characteristic speech pattern, and reporting with reporting circuitry a conclusion based on the determination of whether the patient has complied with the prescribed treatment regimen. In addition to the foregoing, other method aspects are described in the claims, drawings, and text forming a part of the disclosure set forth herein.

In an aspect, a computer program product includes, but is not limited to, a non-transitory machine-readable data storage medium bearing one or more instructions for one or more instructions for receiving a speech data signal with a receiving device at a monitoring location, the speech data signal transmitted to the monitoring location from a patient location, the speech data signal containing speech data, the speech data including patient speech data representing spontaneous speech sensed from a patient by at least one audio sensor at a patient location, and the patient having a brain-related disorder and a prescribed treatment regimen for treating at least one aspect of the brain-related disorder; one or more instructions for identifying with speech identification circuitry patient speech data corresponding to speech from the patient in the speech data, the patient speech data including data indicative of at least one patient speech pattern; one or more instructions for determining with compliance determination circuitry whether the patient has complied with the prescribed treatment regimen based on whether the patient speech data includes data indicative of the at least one patient speech pattern matching at least one characteristic speech pattern; and one or more instructions for reporting with reporting circuitry a conclusion based on the determination of whether the patient has complied with the prescribed treatment regimen. In addition to the foregoing, other aspects of a computer program product including one or more non-transitory machine-readable data storage media bearing one or more instructions are described in the claims, drawings, and text forming a part of the disclosure set forth herein.

In an aspect, a system includes, but is not limited to, a computing device and instructions that when executed on the computing device cause the computing device to receive a speech data signal with a receiving device at a monitoring location, the speech data signal transmitted to the monitoring location from a patient location, the speech data signal containing speech data, the speech data including patient speech data representing spontaneous speech sensed from a patient by at least one audio sensor at a patient location, and the patient having a brain-related disorder and a prescribed treatment regimen for treating at least one aspect of the brain-related disorder; identify with speech identification circuitry patient speech data corresponding to speech from the patient in the speech data, the patient speech data including data indicative of at least one patient speech pattern; determine with compliance determination circuitry whether the patient has complied with the prescribed treatment regimen based on whether the patient speech data includes data indicative of the at least one patient speech pattern matching at least one characteristic speech pattern; and report with reporting circuitry a conclusion based on the determination of whether the patient has complied with the prescribed treatment regimen. In addition to the foregoing, other aspects of a computing device are described in the claims, drawings, and text forming a part of the disclosure set forth herein.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 32 is a flow diagram of further aspects of the method of FIG. 22.

FIG. 33 is a block diagram of a computer program product including an instruction-bearing medium.

DETAILED DESCRIPTION

Figure 1:
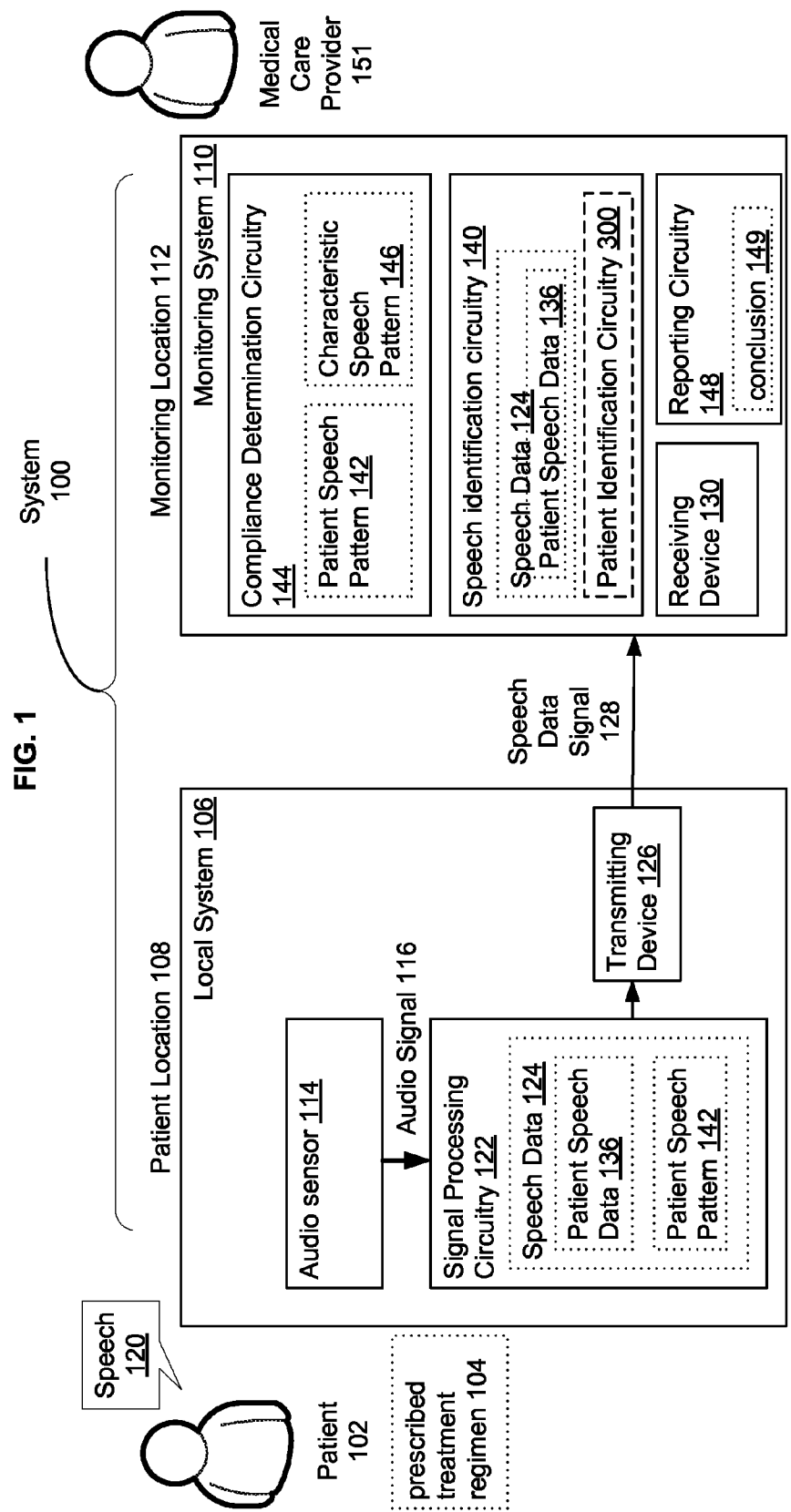
FIG. 1 is a block diagram of a system for monitoring compliance of a patient with a prescribed treatment regimen.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 illustrates a system 100 for monitoring compliance of a patient 102 with a prescribed treatment regimen 104. In an aspect, patient 102 has a brain-related disorder, and prescribed treatment regimen 104 is a treatment regimen prescribed to patient 102 for treating at least one aspect of the brain-related disorder. Brain-related disorders include, for example, mental disorders, psychological disorders, psychiatric disorder, traumatic disorders, lesion-related disorders, and/or neurological disorders, as discussed in greater detail herein below. Prescribed treatment regimen 104 may include a prescription for one or more therapeutic treatments, including medications, pharmaceuticals, nutraceuticals, therapeutic activities, diet, sleep, exercise, counseling, etc., to be used individually or in combination. In various aspects, prescribed treatment regimen 104 specifies type, quantity, and time course of any or all such therapeutic treatments. System 100 monitors compliance of patient 102 with a prescribed treatment regimen 104 by detecting and analyzing speech 120 from patient 102. In an aspect, speech 120 is processed by local system 106, and speech data signal 128 is transmitted to monitoring location 112, and a conclusion 149 (e.g., regarding patient's compliance or lack thereof) reported to medical care provider 151. Systems as described herein can be used, for example, to monitor patient compliance with a prescribed treatment regimen at the request of or with the cooperation and/or authorization of the patient, e.g., in the situation that the patient and/or the patient's caregiver wish to track the patient's compliance with the prescribed treatment regimen. In some cases, monitoring of patient compliance with a prescribed treatment regimen can be implemented at the request or requirement of a caregiver, insurance company, or other individual or entity, for example, as a condition of living in a group home, mental health care facility, or other institution. In some cases, monitoring of compliance can be implemented without knowledge and/or authorization of the patient, e.g., in situations in which the patient is not capable of making decisions for his or her self or to fulfill a legal requirement.

System 100 includes local system 106 at patient location 108, and monitoring system 110 at monitoring location 112. In various aspects, patient location 108 includes, but is not limited, to the patient's home, workplace, school, medical care facility, or group home, or the vicinity of a mobile or stationary device used by the patient, e.g., a cell phone or computer.

Local system 106 includes at least one audio sensor 114 for sensing at least one audio signal 116 including spontaneous speech 120 from patient 102 at patient location 108. Local system 106 also includes signal processing circuitry 122 for detecting spontaneous speech 120 in the at least one audio signal 116 and generating speech data 124 indicative of whether the patient has complied with the prescribed treatment regimen based upon the detected spontaneous speech 120. Spontaneous speech refers to speech that is produced independent of any prompt by system 100, and includes, for example, free-flowing or natural speech. Such speech can be considered "passively captured" from the patient environment in that capture of the spontaneous speech is not predicated on the delivery of a prompt to the patient from system 100. It should be noted, however, that, as used herein, spontaneous speech in some cases includes speech produced by the patient in response to prompts or queries by another person, e.g., in the course of interaction with one or more other person. In addition, speech produced by the patient that is not dependent on prior interaction with another person is also considered "spontaneous speech." In various aspects, speech includes coherent speech, incoherent speech, singing, shouting, whispering, crying, chanting, or other verbal or non-verbal vocalizations. Local system 106 also includes at least one transmitting device 126 for transmitting speech data signal 128 containing speech data 124, which includes indicative of whether patient 102 has complied with the prescribed treatment regimen from patient location 108 to receiving device 130 at a monitoring location 112. Local system 106 may include or be implemented on or in connection with a cell phone, personal computer, or stand-alone microprocessor-based device.

System 100 includes monitoring system 110, which is used at monitoring location 112 for monitoring compliance of patient 102 with prescribed treatment regimen 104. Monitoring system 110 allows medical care provider 151 to remotely monitor compliance of patient 102 with prescribed treatment regimen 104. Monitoring location 112 may be, for example, a hospital, clinic, data center, or doctor's office. Monitoring location 112 may be a short distance away from patient location 108 (e.g., in another room of the same building, or even within the same room as patient location 108) or it may be in a separate building, a few miles away, or many miles away. Monitoring system 110 includes at least one receiving device 130 for use at monitoring location 112 for receiving speech data signal 128 transmitted to monitoring location 112 from patient location 108. Speech data signal 128 contains speech data 124, which may include patient speech data 136. For example, patient speech data 136 represents spontaneous speech sensed from patient 102 with at least one audio sensor 114 at patient location 108. Monitoring system 110 includes speech identification circuitry 140 configured to identify patient speech data 136 corresponding to speech from the patient in speech data 124, where patient speech data 136 is indicative of at least one patient speech pattern 142. Monitoring system 110 also includes compliance determination circuitry 144, which is configured to determine compliance of patient 102 with prescribed treatment regimen 104 based on whether patient speech data 124 is indicative of at least one patient speech pattern 142 matching at least one characteristic speech pattern 146. Monitoring system 110 also includes reporting circuitry 148 configured to report a conclusion 149 based on the determination of whether patient 102 has complied with prescribed treatment regimen 104. In an aspect, conclusion 149 is reported to medical care provider 151 or other appropriate party.

Figure 2:
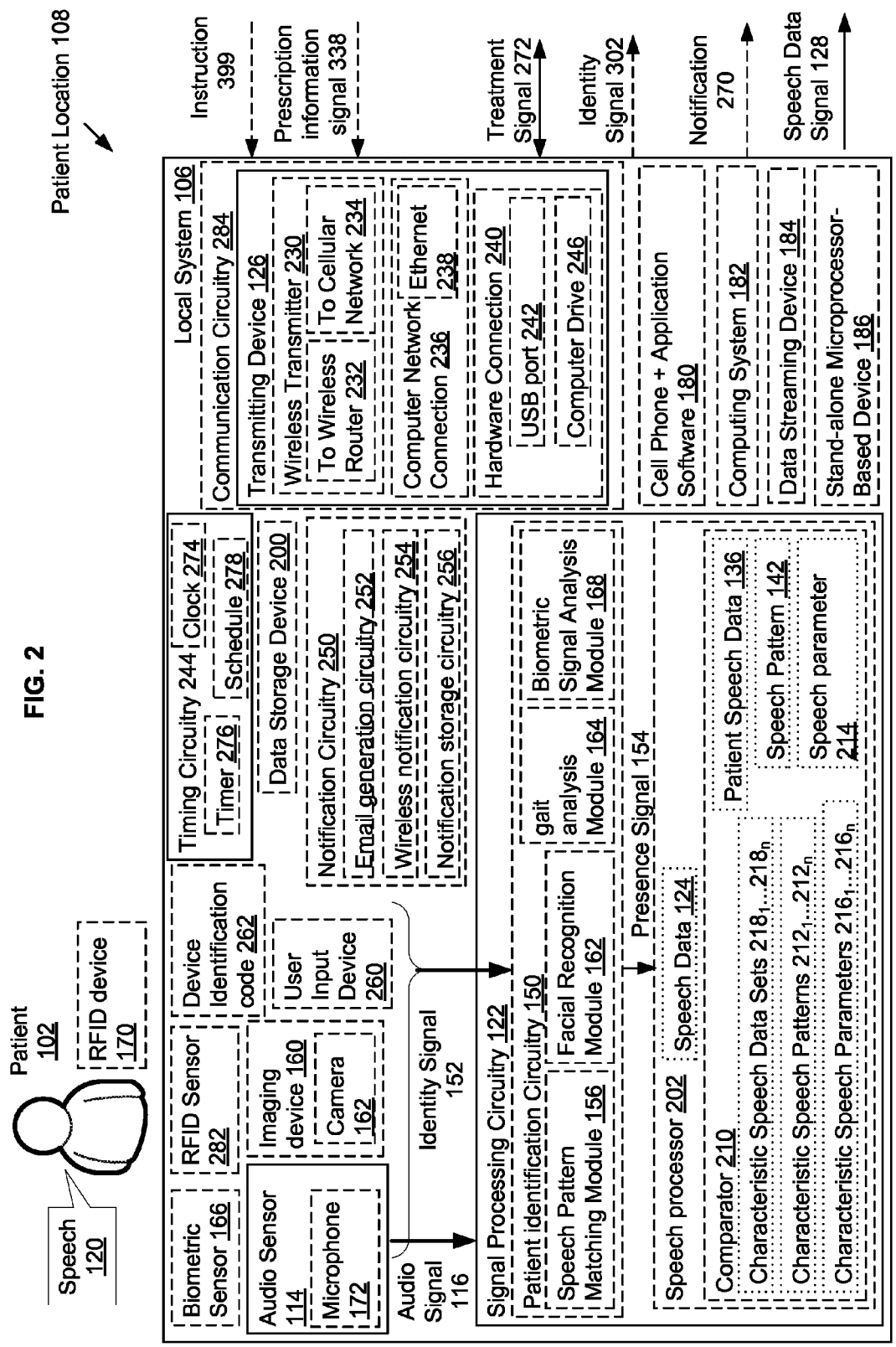
FIG. 2 is a block diagram of components of a system for monitoring compliance of a patient with a prescribed treatment regimen at a patient location.

FIG. 2 provides greater detail regarding local system 106 at patient location 108. Local system 106 can be constructed and implemented in a variety of embodiments in which different devices and/or device components provide the functionality described herein. For example, in various aspects, audio sensor 114, signal processing circuitry 122, and transmitting device 126 may be components of a cell phone configured with application software, as indicated at 180; a computing system or device 182; a data streaming device 184; or a stand-alone microprocessor-based device 186; examples of which are shown in FIGS. 4-7.

In an aspect audio sensor 114 includes microphone 172. Local system 106 may include one or multiple audio sensors 114, which may be of the same or different types, without limitation, and one or more transmitting device 126. Audio sensor 114 may include built-in components (e.g., of cell phone 180, or stand-alone microprocessor-based device 186) or separate components connected to, e.g., a computing system 182 or cell phone 180 via a wired or wireless connection. In an aspect, local system 106 includes one or more data storage device 200, which may be any of various types of data storage and/or memory devices. Local system 106 may include one or more power source (not shown), e.g., a battery, a plug for connecting to an electrical outlet or USB port, or any of various other types of power sources.

Local system 106 includes transmitting device 126, which in various aspects includes a wireless transmitter 230, which may be configured to transmit to a wireless router 232 or cellular network 234, for example. In an aspect, transmitting device 126 includes a computer network connection 236, e.g., an Ethernet connection 238, or a hardware connection 240, for example a USB port 242 or computer drive 246. Transmitting device 126 functions to transmit speech data signal 128, but may also be used to transmit notification 270 generated by notification circuitry 250, identity signal 302, and other data, instructions, or information, for example as discussed elsewhere herein. In some aspects, transmitting device 126 forms a part of communication circuitry 284, which provides for two-way communication between local system 106 and the monitoring system (e.g., monitoring system 110 as shown in FIG. 1), and one-way or two-way communication between local system 106 and other systems or devices located remotely from local system 106.

In an aspect, local system 106 includes notification circuitry 250 for generating a notification. A notification includes any messages or alerts provided to patient 102, medical care provider 151, or other interested parties (e.g., family of patient 102), including but not limited to messages regarding operation of local system 106 or patient compliance, for example. Notifications may take the form of standard messages, a number of which may be stored in data storage device 200. For example, a notification could be a message to patient 102 stating "Reminder: Take your medication" or a message to a medical care provider stating "Alert: Patient xxx speech pattern indicates non-compliance with treatment regimen." Generation of a notification includes retrieval of all or a portion of a message from data storage device 200. In the foregoing example, "xxx" would be replaced by a patient name or identification number, stored separately than the main text of the message and inserted into the message text prior to transmission of the notification to the medical care provider. In various aspects, notification circuitry 250 includes at least one of email generation circuitry 252 for generating an email notification, wireless notification circuitry 254 for generating a notification to be transmitted via a wireless transmitter (e.g., wireless transmitter 230), and notification storage circuitry 256 for storing a notification in a data storage device (e.g., data storage device 200). In some cases, notifications may be stored for later retrieval or transmittal to a monitoring location. Notification 270 generated by notification circuitry 250 can be transmitted by signal processing circuitry 122.

In an aspect, speech data signal 128 transmitted to monitoring system 110 contains processed data. In some cases a determination of whether patient 102 has complied with prescribed treatment regimen 104 is made by local system 106. In some cases speech data signal 128 transmitted to monitoring location 112 includes speech data that has not been subjected to significant processing, and speech processing and detection of patient compliance is performed at monitoring location 112. In an aspect, speech data is stored for later processing, e.g., in data storage device 200 in local system 106, or is subjected to processing but also stored for later transfer to monitoring location 112.

Signal processing circuitry 122 is used for detecting spontaneous speech 120 in the at least one audio signal 116 and generating speech data 124 including data indicative of whether the patient has complied with the prescribed treatment regimen based upon the detected spontaneous speech 120. As used herein, "speech data including data indicative of whether the patient has complied with the prescribed treatment regimen" means speech data that includes informative speech data, i.e., speech data from which it may be determined that the patient complied with the prescribed treatment regimen. "Speech data including data indicative of whether the patient has complied with the prescribed treatment regimen" may, in addition to informative speech data, include non-informative speech data, i.e., speech data that does not provide any information regarding, and from which it cannot be determined, whether the patient complied with the prescribed treatment regimen. As used herein, "speech data" may refer to any or all of a digitized audio signal containing one or more speech-containing portions and one or more non-speech-containing portions, a digitized audio signal from which non-speech-containing portions have been removed to leave one or more speech-containing portions, speech pattern data derived or computed from a digitized audio signal containing speech, or speech parameter data derived or computed from a digitized audio signal containing speech, for example. "Speech data" may include several types of data, e.g., one or more digitized audio signal, one or more speech pattern, and/or one or more speech parameter.

In an aspect, signal processing circuitry 122 includes speech processor 202. In an aspect, speech processor 202 is configured to process the at least one audio signal 116 to identify at least one portion of the at least one audio signal 116 containing spontaneous speech of the patient. In an aspect, speech processor 202 is configured to process at least one audio signal 116 to exclude at least one portion of at least one audio signal 116 that does not contain spontaneous speech of the patient. In an aspect, speech data 124 includes the at least one section of the at least one audio signal 116 containing spontaneous speech of the patient.

In an aspect, speech processor 202 is configured to process at least one audio signal 116 to determine at least one speech pattern 142 of the patient. In an aspect, speech data 124 includes the at least one speech pattern 142 of the patient.

A speech pattern can be defined as a consistent, characteristic form, style, or method of speech comprising a distribution or arrangement of repeated or corresponding parts composed of qualities, acts, or tendencies. In an embodiment a speech pattern can include one or more qualities of diction, elocution, inflection, and/or intonation. In an embodiment a speech pattern can include aspects of language at the lexical level, sentential level, or discourse level. In an embodiment, a speech pattern may conform to the Thought, Language, and Communication Scale and/or Thought and Language Index. Reviews describing speech patterns and linguistic levels and the tools used to study them include Covington M. A., et al. "Schizophrenia and the structure of language: The linguist's view," Schizophrenia Research 77: 85-98, 2005, and Kuperberg and Caplan (2003 Book Chapter: Language Dysfunction in Schizophrenia), which are both incorporated herein by reference.

In an embodiment a speech pattern includes a linguistic pattern determined at the lexical level. A speech pattern may include a frequency of, for example, pauses, words, or phrases. For example a speech pattern may include a frequency of pauses. A higher frequency of pauses or reduced verbal fluency can be indicative of alogia associated with a brain disorder, e.g., bipolar disorder, depression, or schizophrenia. For example, a speech pattern may include a frequency of dysfluencies ("uhs" and "ums"). A higher than average frequency of dysfluencies may indicate a slowed speech, the inability to think clearly, or a deliberate attempt to appear unaffected by illness, all of which have been associated with psychological pathologies. For example, a speech pattern may include a distribution of pauses and dysfluencies. A high frequency and particular distribution of pauses and dysfluencies may be indicative of anomia associated with schizophrenia or with an aphasia due to brain injury. For example, a speech pattern may include a frequency of neologisms and/or word approximations, or glossomania. Higher than average frequencies of neologisms and/or word approximations, or glossomania, have been associated with disorders such as schizophrenia, schizoaffective disorder, or mania. For example a speech pattern may include a frequency of word production. A frequency of word production lower than the norm may be indicative of a brain disorder such as schizophrenia. An excessive speed during speech, as in pressured speech, may be indicative of a brain disorder such as the mania of bipolar disorder, while reduced speed may be indicative of depression or a depressive episode. For example, a pattern may include a type: token ratio (i.e., number of different words (types) in relation to the total number of words spoken (tokens)). A type:token ratio that is generally lower than the norm can be indicative of schizophrenia. For example, a speech pattern may include a frequency of specific words. Quantitative word counts have been used as a tool in the identification and examination of abnormal psychological processes including major depression, paranoia, and somatization disorder. A high frequency of negative emotion words or death-related words may be indicative of depression. Psychologically relevant words can include those listed in one or more dictionaries of the Linguistic Inquiry and Word Count (LIWC) program (see Tausczik and Pennebaker, "The Psychological Meaning of Words: LIWC and Computerized Text Analysis Methods," Journal of Language and Social Psychology 29(1): 24-54, 2010, which is incorporated herein by reference). Words interpreted as carrying normative emotional qualities are found in dictionaries of two programs, *Affective Norms for English Words* (*ANEW*) *and Dictionary of Affect in Language* (*DAL*) (see Whissell C., "A comparison of two lists providing emotional norms for English words (ANEW and the DAL)," Psychol Rep., 102(2):597-600, 2008, which is incorporated herein by reference).

In an embodiment a speech pattern includes a linguistic pattern determined at the sentential level or discourse level. For example, a speech pattern can include a consistent grammatical style. A pattern comprising a style that is grammatically deviant from the norm might include the overuse of the past tense, indicating detachment from the subject being discussed. A pattern comprising a style that is grammatically deviant from the norm, e.g., as reflected by a higher percentage of simple sentences and, in compound sentences, fewer dependent clauses may be indicative of schizophrenia. For example, a speech pattern may include a ratio of syntactic complexity (number of clauses and proportion of relative:total clauses). An abnormal ratio may indicate a brain disorder. For example, a speech pattern may include a frequency of subordinate clauses. An increase in subordinate clauses has been observed in the speech of psychopaths (see, e.g., Hancock et al., "Hungry like the wolf: A word-pattern analysis of the language of psychopaths," Legal and Criminological Psychology, 2011; DOI: 10.1111/j.2044-8333.2011.02025.x, which is incorporated herein by reference). For example, a speech pattern may include a relatedness of lexical content such as semantic or sentential priming. A speech pattern of abnormal priming may indicate a brain disorder such as schizophrenia. For example, a speech pattern may include a frequency of one or more use of cohesive ties, e.g., as demonstrated by references, conjunctions, or lexical cohesion. A low frequency of reference ties has been observed in patients suffering from schizophrenia. For example, a speech pattern may include an hierarchical structure within a discourse, e.g., a systematic structure in which propositions branch out from a central proposition. A speech pattern lacking a systematic structure may be indicative of schizophrenia.

For example, a speech pattern including a linguistic pattern determined at the sentential level or discourse level may include a representation of content of thought (what the patient is talking about). For example, a speech pattern may include a representation of form of thought (the way ideas, sentences, and words are put together). A speech pattern containing representations of content or form of thought that differ from those expected (e.g., as determined from population patterns) may indicate a psychological disorder such as schizophrenia. Examples of representations of content or form of thought observed in schizophrenia include derailment, loss of goal, perseveration, and tangentiality. For example, a speech pattern may include aspects of linguistic pragmatics (e.g., cohesion or coherence). Abnormal patterns in pragmatics may be indicative of a brain disorder such as schizophrenia or mania. Examples of speech patterns and content of thought are discussed by Covington, et al., idem, and by Kuperberg and Caplan idem. A program for classifying parts of speech (e.g., noun, verb, adjective, etc.) based on the surrounding context and analysis of semantic content has been developed and is available under the Wmatrix interface (http://ucrel.lancs.ac.uk/wmatrix/) and has been used to analyze the speech of psychopaths (see Hancock, idem).

In an embodiment, a speech pattern includes an acoustic quality. In an embodiment a speech pattern includes volume. For example, excessive or reduced volume may be indicative of a symptom of a brain disorder. In an embodiment a speech pattern includes prosody (the rhythm, stress, and intonation of speech). For example, aprosody or flattened intonation can be indicative of schizophrenia. In an embodiment a speech pattern includes a voice quality of phonation. In an embodiment a speech pattern includes pitch or timbre. For example, abnormalities in pitch have been observed in schizophrenics. For example, a strained quality, choking voice, or creaking voice (laryngealisation) may be indicative of a psychological disorder. Voice qualities and volume in linguistics are discussed by Covington, idem.

For example, the at least one speech pattern 142 may be represented in speech data 124 in numerical or categorical form. For example, a speech pattern represented in numerical form may include one or more numerical values representing one or more speech parameters. Particular speech parameters represented in a speech pattern may be selected for the purpose of evaluating/monitoring particular brain-related disorders. For example, in an aspect a speech pattern for evaluating/monitoring depression includes values representing the following parameters: speech volume, frequency of word production, frequency of pauses, and frequency of negative value words. In another aspect, a speech pattern for evaluating/monitoring schizophrenia includes values representing frequency of word production, frequency of pauses, frequency of disfluencies, type:token ratio, and speech volume. A speech parameter or pattern may be represented in speech data 124 in categorical form; for example, frequency of word production may be categorized as low, medium, or high rather than represented by a specific numerical value.

In an aspect, signal processing circuitry 122 includes comparator 210 for comparing at least one speech pattern 142 of patient 102 with at least one characteristic speech pattern 212 to determine whether the patient has complied with the prescribed treatment regimen. In an aspect, comparator 210 is configured to compare at least one speech pattern 142 of the patient with a plurality of characteristic speech patterns $212_1$ . . . $212_n$ to determine whether the patient has complied with the prescribed treatment regimen. For example, in an aspect, the result of such a comparison is either "patient has complied" or "patient has not complied." In an aspect, signal processing circuitry 122 is configured to determine that patient 102 has failed to comply with the prescribed treatment regimen. In an aspect, signal processing circuitry 122 is configured to determine that patient 102 has complied with prescribed treatment regimen 104. Determination of compliance may be accomplished by a thresholding, windowing, or distance computation of one or multiple parameters relative to characteristic threshold or range values for the parameter. For example, for a given parameter, a patient parameter value higher than a characteristic threshold value may indicate compliance of the patient with the prescribed treatment regimen, while a patient parameter value equal to or lower than the threshold value may indicate non-compliance. As another example, a patient parameter value that lies within a range of characteristic values for the parameter may indicate compliance, while a patient parameter value outside the range of characteristic values indicates non-compliance. Comparator 210 may utilize various types of distance computations to determine whether patient parameter values are within a threshold distance or distance range from characteristic values. Distance computations based on one or more parameters or data values are known (including, but not limited to, least-squares calculations). In an aspect, signal processing circuitry 122 is configured to determine whether the patient has complied with the prescribed treatment regimen based upon a determination of whether the speech corresponds to at least one of a plurality of characteristic speech patterns. For example, the plurality of characteristic speech patterns can include multiple characteristic speech patterns, each corresponding to a patient speech pattern obtained at a different treatment regimen, for example different doses of a drug. By identifying which characteristic speech pattern the patient speech pattern matches or is closest to, the drug dose taken by the patient can be determined. For example, the patient may have taken the drug, but at a lesser dose or less often than was prescribed. Accordingly, the patient's speech pattern matches the characteristic speech pattern associated with the lesser dose of drug, indicating partial, but not full, compliance of the patient with the prescribed treatment regimen.

In an aspect, speech processor 202 is configured to process at least one audio signal 116 to determine at least one speech parameter 214 indicative of whether the patient has complied with the prescribed treatment regimen. Speech parameters include, but are not limited to, measures of prosody, rhythm, stress, intonation, variance, intensity/volume, pitch, length of phonemic syllabic segments, and length of rising segments, for example. In an aspect, speech data 124 includes at least one speech parameter 214, which may include, for example, one or more of prosody, rhythm, stress, intonation, variance, intensity/volume, pitch, length of phonemic syllabic segments, and length of rising segments. In an aspect, signal processing circuitry 122 includes comparator 210 for comparing at least one speech parameter 214 of the patient with at least one characteristic speech parameter 216 to determine whether the patient has complied with the prescribed treatment regimen. In an aspect, comparator 210 is configured to compare at least one speech parameter 214 of the patient with a plurality of characteristic speech parameters $216_1 \ldots 216_n$ to determine whether the patient has complied with the prescribed treatment regimen. For example, in an aspect, the result of such a comparison is either "patient has complied" or "patient has not complied." In an aspect, comparator 210 is configured to compare at least one speech parameter 214 of the patient with a plurality of characteristic speech parameters $216_1 \ldots 216_n$ to determine a level of compliance of the patient with the prescribed treatment regimen. Determination of compliance, non-compliance, or level of compliance may be performed with comparator 210 using thresholding, windowing, or distance measurements, for example, as described herein above. Similarly, determination of compliance or non-compliance of patient 102 with a prescribed treatment regimen maybe be accomplished with the use of comparator 210 for various types of speech data by comparing patient speech data 136 with one or more characteristic speech data set $218_1 \ldots 218_n$, using approaches as described herein above.

In some aspects, signal processing circuitry 122 separates patient speech data 136 originating from patient 102 from speech originating from other individuals and/or from other sounds present in audio signal 116. In an aspect, signal processing circuitry 122 includes patient identification circuitry 150, which is configured to determine the presence of the patient from at least one identity signal 152 sensed at patient location 108. Signal processing circuitry 122 is configured to detect spontaneous speech 120 from patient 102 based at least in part on the determination of the presence of the patient by the patient identification circuitry 150, as indicated by presence signal 154. Identifying speech 120 originating from patient 102 may be of significance, for example, if more than one individual is present, or expected to be present, at patient location 108, such that audio signal 116 may contain speech from individuals other than, or in addition to, patient 102. In various aspects, determining the identity and/or presence of patient 102 may aid in distinguishing speech from patient 102 from speech from other people or non-speech sounds from any other sources, and may assure that conclusions based on analysis patient speech data are reflective of the compliance of patient 102 with the prescribed treatment regimen.

Various types of identity signal 152 can provide information regarding the presence and identity of patient 102. In an aspect, identity signal 152 includes at least a portion of audio signal 116, wherein patient identification circuitry 150 is configured to analyze audio signal 116 to determine the presence of patient 102 by identifying at least a portion of audio signal 116 that resembles known speech of the patient (e.g., with speech pattern matching module 156), and wherein signal processing circuitry 122 is configured to detect spontaneous speech from patient 102 by identifying speech data 124 corresponding to presence of the patient detected from the audio signal, to obtain patient speech data 136. For example, a continuous speech system may be used for identifying the speaker, as described in Chandra, E. and Sunitha, C., "A review on Speech and Speaker Authentication System using Voice Signal feature selection and extraction," IEEE International Advance Computing Conference, 2009. IACC 2009, Page(s): 1341-1346, 2009 (DOI: 10.1109/IADCC.2009.4809211), which is incorporated herein by reference. In an aspect, patient identification circuitry 150 is configured to analyze speech data signal 128 to determine the presence of the patient based on frequency analysis of the speech data signal. Magnitude or phase spectral analysis may be used, as described in McCowan, I.; Dean, D.; McLaren, M.; Vogt, R.; and Sridharan, S.; "The Delta-Phase Spectrum With Application to Voice Activity Detection and Speaker Recognition," IEEE Transactions on Audio, Speech, and Language Processing, 2011, Volume: 19, Issue: 7, Page(s): 2026-2038 (DOI: 10.1109/TASL.2011.2109379), which is incorporated herein by reference.

In another aspect, identity signal 152 includes an image signal received from an imaging device 160 at patient location 108, wherein the patient identification circuitry 150 is configured to analyze the image signal to determine the presence of the patient and to generate presence signal 154, and wherein signal processing circuitry 122 is configured to detect spontaneous speech from the patient by identifying speech data corresponding to presence of the patient detected from the image signal, as indicated by presence signal 154, to obtain patient speech data 136. Imaging device 160 may include a camera 162 or other type of imaging device known to those of skill in the art. In an aspect, the patient identification circuitry 150 is configured to analyze the image signal to determine the presence of the patient through facial recognition, with facial recognition module 162, e.g., using approaches as described in Wheeler, Frederick W.; Weiss, R. L.; and Tu, Peter H., "Face recognition at a distance system for surveillance applications," Fourth IEEE International Conference on Biometrics: Theory Applications and Systems (BTAS), 2010 Page(s): 1-8 (DOI: 10.1109/BTAS.2010.5634523), and Moi Hoon Yap; Ugail, H.; Zwiggelaar, R.; Rajoub, B.; Doherty, V.; Appleyard, S.; and Hurdy, G., "A Short Review of Methods for Face Detection and Multifractal Analysis," International Conference on CyberWorlds, 2009. CW '09., Page(s): 231-236 (DOI: 10.1109/CW.2009.47), both of which are incorporated herein by reference. In an aspect, patient identification circuitry 150 is configured to analyze the image signal to determine the presence of the patient through gait analysis, with gait analysis module 164. Identification of the patient based on gait analysis can be performed for example by methods as described in U.S. Pat. No. 7,330,566, issued Feb. 12, 2008 to Cutler, and Gaba, I. and Kaur P., "Biometric Identification on The Basis of BPNN Classifier with Other Novel Techniques Used For Gait Analysis," Intl. J. of Recent Technology and Engineering (IJRTE) ISSN: 2277-3878, Vol. 2, issue 4, September 2013, pp. 137-142, both of which are incorporated herein by reference.

In an aspect, identity signal 152 includes a biometric signal from at least one biometric sensor 166 at patient location 108, wherein the patient identification circuitry 150 is configured analyze the biometric signal to determine the presence of patient 102, and wherein signal processing circuitry 122 is configured to detect spontaneous speech from the patient by identifying speech data corresponding to presence of the patient as determined from the biometric signal, with biometric signal analysis module 168. Biometric identification can include face and gait recognition, as described elsewhere herein, and recognition based on a variety of other physiological or behavioral characteristics, such as fingerprints, voice, iris, retina, hand geometry, handwriting, keystroke pattern, e.g., as described in Kataria, A. N.; Adhyaru, D. M.; Sharma, A. K.; and Zaveri, T. H., "A survey of automated biometric authentication techniques" Nirma University International Conference on Engineering (NUiCONE), 2013, Page(s): 1-6 (DOI: 10.1109/NUiCONE.2013.6780190), which is incorporated herein by reference. U.S. Pat. No. 8,229,178 issued Jul. 24, 2012 to Zhang et al., which is incorporated herein by reference, describes a method for acquiring a palm vein image with visible and infrared light and extracting features from the image for authentication of individual identity. Biometric identification can be based on imaging of the retina or iris, as described in U.S. Pat. No. 5,572,596 issued to Wildes et al. on Nov. 5, 1996 and U.S. Pat. No. 4,641,349 issued to Flom et al. on Feb. 3, 1987, each of which is incorporated herein by reference. Combinations of several types of identity signals can also be used (e.g., speech and video, as described in Aleksic, P. S. and Katsaggelos, A. K. "Audio-Visual Biometrics," Proceedings of the IEEE Volume: 94, Issue: 11, Page(s): 2025-2044, 2006 (DOI: 10.1109/JPROC.2006.886017), which is incorporated herein by reference).

In an aspect, identity signal 152 includes at least one authentication factor, for example, a security token, a password, a digital signature, or a cryptographic key, entered by patient 102 via user input device 260. User input device 260 can include various types of user input devices or controls as are well known to those of ordinary skill in the art, including but not limited to keyboards, touchpads, touchscreen, mouse, joystick, microphone or other voice input, buttons, or switches. One or more user input device 260 in local system 106 can be used to receive various types of user inputs relating to operation of local system 106, not limited to entry of an authentication factor.

In another aspect, identity signal 152 includes a device identification code 262, which identifies a device or component of local system 106. Device identification code 262 may be, for example, a cell phone identification code, such as an electronic serial number, a mobile identification number, or a system identification code. In various aspects, device identification code 262 identifies a cell phone 180, a computing system 182, or a stand-alone microprocessor-based device 186, or a component thereof. Device identification code 262 can serve to identify patient 102 providing the identified device, for example a personal computer or cell phone, is consistently used only by patient 102.

In an aspect, identity signal 152 includes a radio frequency identification (RFID) signal, e.g., from an RFID device 170, which may be carried, worn by, or otherwise associated with patient 102 and sensed by RFID sensor 282. RFID device 170 can be a passive RFID in a tag or chip associated with the patient, and RFID sensor 282 can be a sensed with an active RFID reader may be used.

In an aspect, presence signal 154 is provided as an input to signal processing circuitry 122. Presence of patient 102 may be indicated by a value of presence signal 154. For example, in some aspects, presence signal 154 is a binary signal; e.g., presence signal 154 has a high value if the patient is present or a low value if the patient is not present (or vice versa). In an aspect, patient speech data 124 is acquired from audio signal 116 only when the value of presence signal 154 indicates that patient 102 is present. Alternatively, in some aspects presence signal 154 is a continuous valued signal that indicates the probability that the patient is present. For example, presence signal 154 has a value of 100 if there is 100 percent probability that the patient is present, a value of zero if there is zero percent probability that the patient is present, or an intermediate value if there is an intermediate probability that the patient is present. It will be appreciated that in some contexts, the determination of whether the patient is present or absent will be relatively straightforward, in which case a binary presence signal may be appropriate, whereas in others (e.g., in cases where the presence of the patient must be distinguished from the presence of other individuals) there is some likelihood of error in identifying the presence of the patient (with the likelihood of error potentially dependent upon the number and identity of the other individuals present), such that an indication of the probability that the patient is present may be more appropriate.

Figure 3:
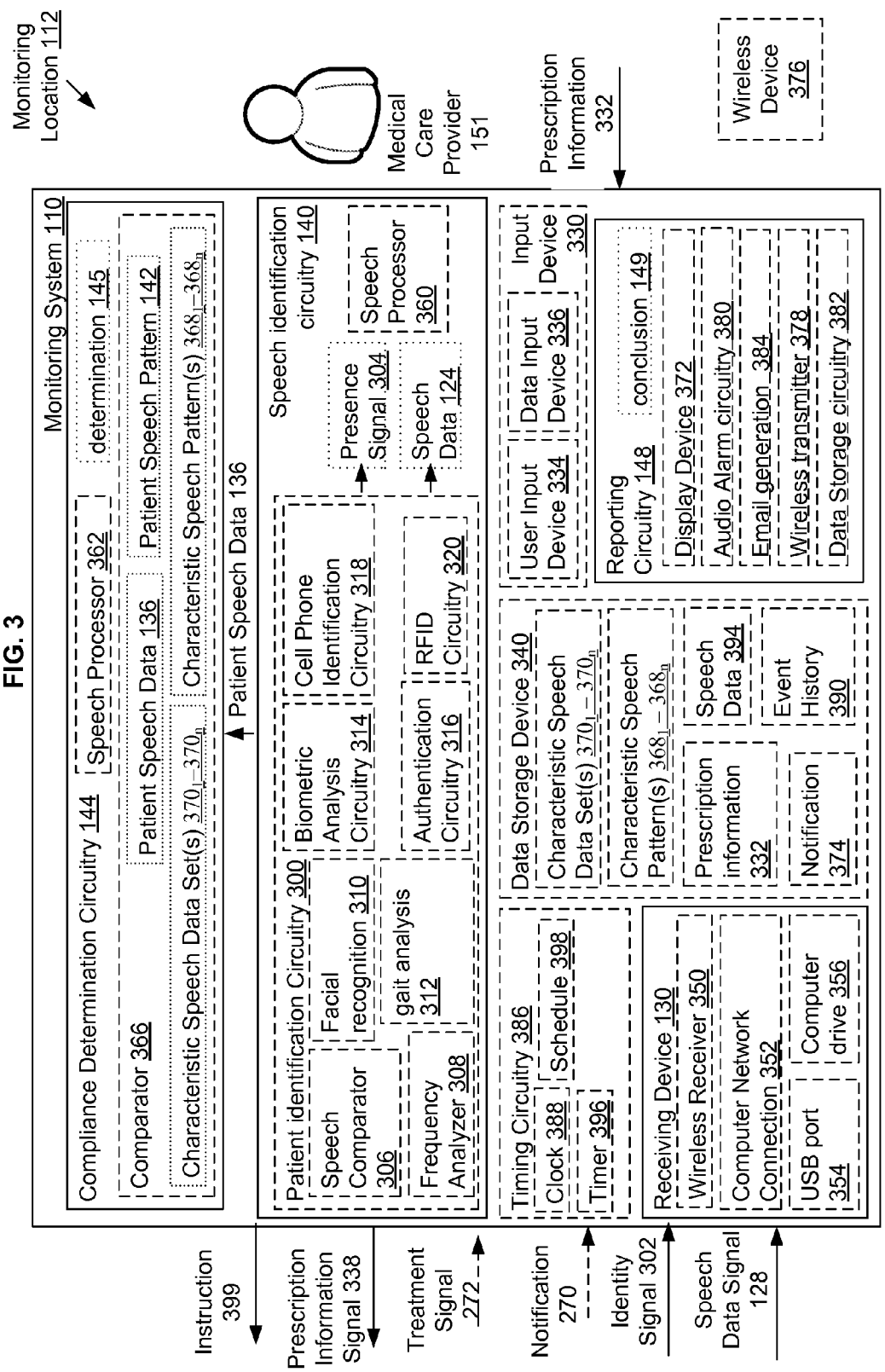
FIG. 3 is a block diagram of components a system for monitoring compliance of a patient with a prescribed treatment regimen at a monitoring location.

FIG. 3 provides greater detail regarding monitoring system 110 at monitoring location 112. In an aspect, speech identification circuitry 140 in monitoring system 110 includes patient identification circuitry 300 configured to determine a presence of the patient from at least one identity signal 302 received at monitoring location 112 from the patient location, wherein speech identification circuitry 140 is configured to identify patient speech data 136 corresponding to speech from the patient in the speech data 124 based at least in part on the determination of the presence of the patient by patient identification circuitry 300.

Presence of the patient is indicated by a value of presence signal 304. In some aspects, presence signal 304 is a binary signal; e.g., presence signal 304 has a high value if the patient is present or a low value if patient is not present (or vice versa). Alternatively, presence signal 304 is a continuous valued signal that indicates the probability that the patient is present. For example, presence signal 304 has a value of 100 if there is 100 percent probability that the patient is present, a value of zero if there is zero percent probability that the patient is present, or an intermediate value if there is an intermediate probability that the patient is present. As discussed herein above, in some contexts, the determination of whether the patient is present or absent will be relatively straightforward, and a binary presence signal may be appropriate, whereas in others (e.g., in cases where the presence of the patient must be distinguished from the presence of other individuals) there is some likelihood of error in identifying the presence of the patient (with the likelihood of error potentially dependent upon the number and identity of the other individuals present), such that an indication of the probability that the patient is present may be more appropriate.

In an aspect, identity signal 302 includes at least a portion of speech data signal 128, and patient identification circuitry 300 is configured to analyze speech data signal 128 to determine the presence of the patient based on speech data signal 128, by identifying at least a portion of speech data signal 128 that resembles a known speech data signal of the patient, with speech comparator 306. Accordingly, speech identification circuitry 140 is configured to identify patient speech data 136 by identifying speech data 124 corresponding to presence of the patient detected from the speech data signal 128. For example, a continuous speech system may be used for identifying the speaker, as described in Chandra, E. and Sunitha, C., "A review on Speech and Speaker Authentication System using Voice Signal feature selection and extraction," IEEE International Advance Computing Conference, 2009. IACC 2009, Page(s): 1341-1346, 2009 (DOI: 10.1109/IADCC.2009.4809211), which is incorporated herein by reference. In an aspect, patient identification circuitry 300 is configured to analyze speech data signal 128 to determine the presence of the patient based on frequency analysis of the speech data signal, with frequency analyzer 308. Magnitude or phase spectral analysis may be used, as described in McCowan, I.; Dean, D.; McLaren, M.; Vogt, R.; and Sridharan, S.; "The Delta-Phase Spectrum With Application to Voice Activity Detection and Speaker Recognition," IEEE Transactions on Audio, Speech, and Language Processing, 2011, Volume: 19, Issue: 7, Page(s): 2026-2038 (DOI: 10.1109/TASL.2011.2109379), which is incorporated herein by reference.

In an aspect, identity signal 302 includes an image signal received from an imaging device at the patient location (e.g., imaging device 160 as shown in FIG. 2), wherein patient identification circuitry 300 is configured to analyze the image signal to determine the presence of the patient, and wherein speech identification circuitry 140 is configured to identify patient speech data 136 by identifying speech data 124 corresponding to presence of the patient detected from the image signal. For example, patient identification circuitry 300 may be configured to analyze the image signal to determine the presence of the patient through facial recognition, with facial recognition circuitry 310, for example using approaches as described in Wheeler, Frederick W.; Weiss, R. L.; and Tu, Peter H., "Face recognition at a distance system for surveillance applications," Fourth IEEE International Conference on Biometrics: Theory Applications and Systems (BTAS), 2010 Page(s): 1-8 (DOI: 10.1109/BTAS.2010.5634523), and Moi Hoon Yap; Ugail, H.; Zwiggelaar, R.; Rajoub, B.; Doherty, V.; Appleyard, S.; and Hurdy, G., "A Short Review of Methods for Face Detection and Multifractal Analysis," International Conference on CyberWorlds, 2009. CW '09., Page(s): 231-236 (DOI: 10.1109/CW.2009.47), both of which are incorporated herein by reference. Alternatively, or in addition, patient identification circuitry 300 may be configured to analyze the image signal to determine the presence of the patient through gait analysis, with gait analysis circuitry 312. Identification of the patient based on gait analysis can be performed, for example by methods as described in U.S. Pat. No. 7,330,566, issued Feb. 12, 2008 to Cutler, and Gaba, I. and Kaur P., "Biometric Identification on The Basis of BPNN Classifier with Other Novel Techniques Used For Gait Analysis," Intl. J. of Recent Technology and Engineering (IJRTE) ISSN: 2277-3878, Vol. 2, issue 4, September 2013, pp. 137-142, both of which are incorporated herein by reference.

In an aspect, the identity signal includes a biometric signal from at least one biometric sensor 166 at the patient location 108 (as shown in FIG. 2), wherein patient identification circuitry 300 in FIG. 3 is configured to analyze the biometric signal to determine the presence of the patient, with the use of biometric analysis circuitry 314, and wherein speech identification circuitry 140 is configured to identify patient speech data 136 by identifying speech data 124 corresponding to presence of the patient detected from the biometric signal. Biometric signal analysis can be performed as described elsewhere herein.

In an aspect, identity signal 302 includes at least one authentication factor, which may be, for example, a security token, a password, a digital signature, or a cryptographic key. In an aspect, an authentication factor is entered by the patient via a user input device, e.g., user input device 260 in FIG. 2. User input device 260 can include various types of user input devices or controls as are well known to those of ordinary skill in the art, including but not limited to a keyboard, touchpad, touchscreen, mouse, joystick, or microphone or other voice input.

In an aspect, patient identification circuitry 300 includes authentication circuitry 316 for determining the identity of the patient based upon the authentication factor. In some aspects, identity signal 302 includes a cell phone identification code, which may be, for example, an electronic serial number, a mobile identification number, or a system identification code, and patient identification circuitry 300 include cell phone identification circuitry 318. Combinations of several types of identity signals can also be used (e.g., speech and video, as described in Aleksic, P. S. and Katsaggelos, A. K. "Audio-Visual Biometrics," Proceedings of the IEEE Volume: 94, Issue: 11, Page(s): 2025-2044, 2006 (DOI: 10.1109/JPROC.2006.886017), which is incorporated herein by reference).

It will be appreciated that identity signal 302 may conveniently be a cell phone identification code when local system 106 is embodied as a cell phone configured with application software, as indicated at 180 in FIG. 2. In connection therewith, patient identification circuitry 300 includes cell phone identification circuitry 318. In another aspect, identity signal 302 includes an RFID signal, e.g., from RFID device 170 associated with patient 102 at patient location 108, as depicted and described in connection with FIG. 2, and patient identification circuitry 300 includes RFID circuitry 320.

In an aspect, monitoring system 110 includes input device 330 for receiving prescription information 332 indicative of the treatment regimen prescribed to the patient. Input device 330 may be a user input device 334 (e.g., a keyboard, touchpad, touchscreen, mouse, joystick, microphone or other voice input, etc.) adapted for receiving prescription information from, e.g., medical care provider 151, or data input device 336 adapted to receive data from another device (e.g., a computer system, a networked system, a cell phone, a barcode reader, a flash drive, a disk drive, etc. via a wired or wireless connection as is well known in the relevant arts).

In an aspect, monitoring system 110 includes at least one data storage device 340 for storing prescription information indicative of the treatment regimen prescribed to the patient. Data stored in data storage device 340 may include, but is not limited to speech data 124, prescription information 332 (including details of the prescribed treatment regimen), stored messages regarding device status, device settings, instructions, or conclusions, for example. Data storage device 340 is a data storage device or system that forms a part of monitoring system 110, or is accessible by monitoring system 110, e.g., on a server and/or cloud-based data storage system. In an aspect, data storage device 340 includes one or more database containing electronic medical records, for example.

In various aspects, the at least one receiving device 130, which receives speech data signal 128 transmitted to monitoring location 112 from patient location 108, includes a wireless receiver 350, a computer network connection 352, a USB port 354, or a computer drive 356. Transmission of data or information to receiving device 130 thus encompasses wireless or wired transmission, and also device-based transmission involving transfer of a data from local system 106 at patient location 108, via a data storage device (e.g., a flash drive or DVD), to a data reading device (USB port 354 or computer drive 356) in monitoring system 110 that reads data from the data storage device. Monitoring system 110 in some aspects includes more than one receiving device, and multiple receiving devices may be of the same or different types. In some aspects, receiving device 130 receives various types of data and/or information from local system 106 at patient location 108, not limited to speech data signal 128. Furthermore, in some aspects receiving device 130 receives data or information from devices and systems other than local system 106. For example, in some aspects, receiving device 130 may also serve as data input device 336.

In an aspect, at least one of speech identification circuitry 140 and compliance determination circuitry 144 includes a speech processor, (see, e.g., speech processor 360 in speech identification circuitry 140 and speech processor 362 in compliance determination circuitry 144.) In an aspect a single speech processor may be shared by speech identification and compliance determination circuitry.

In an aspect, compliance determination circuitry 144 includes speech processor 362 for analyzing the patient speech data 136 to determine the at least one patient speech pattern 142 and a comparator 366 for comparing the at least one patient speech pattern 142 with one or multiple characteristic speech patterns $368_1$-$368_n$. One or more characteristic speech patterns $368_1$-$368_n$ may be stored in data storage device 340. In some aspects, operation of comparator 366 may be substantially similar to that of comparator 210; however, it will be appreciated that the same speech processing functions need not be performed at both patient location 108 and monitoring location 112. Thus, in some aspects system 100 includes either comparator 210 in local system 106 or comparator 366 in monitoring system 110, but not both. In other aspects, system 100 includes some degree of redundancy, such that local system 106 includes comparator 210 and monitoring system 110 includes comparator 366.

Various aspects of system functionality can be distributed between local system 106 and monitoring system 110. With regard to processing of speech signals, if the majority of speech processing takes place in monitoring system 110, speech data transmitted in speech data signal 128 may be minimally processed. On the other hand, if the majority of speech processing is performed in local system 106, speech data signal 128 may contain processed speech data (e.g., speech patterns and/or parameters). However, even if speech processing is performed in local system 106, both processed and unprocessed speech data (e.g., raw speech data as well as speech parameters and or speech patterns) may be included in speech data signal 128.

In some aspects, patient speech data 136 may be compared directly with characteristic speech data sets, rather than being processed first by speech processor 362 to determine patient speech pattern 142, such that the comparison is performed between patient speech pattern 142 and characteristic speech patterns $368_1$-$368_n$, as described above. In an aspect, comparator 366 in compliance determination circuitry 144 compares patient speech data 136 with one or multiple characteristic speech data sets $370_1$-$370_n$ indicative of the characteristic speech pattern, where each said characteristic speech data set is indicative of a characteristic speech pattern.

In the above scenarios, the result of the comparison performed by comparator 366 is a determination that the patient speech data (or patient speech pattern derived therefrom) either does, or does not, match one or more characteristic speech data sets or speech patterns. As discussed above, if there is a match, conclusion 149 is generated regarding whether the patient has complied with the prescribed treatment regimen. In practice, the comparison performed by comparator 366 (which may include thresholding, windowing, distance computation, for example, as discussed herein above) will result in production of a signal by compliance determination circuitry that indicates at least whether the patient has complied with the prescribed treatment regimen, and alternatively, or in addition, a level of compliance with the prescribed treatment regimen.

In an aspect, the compliance determination circuitry 144 is configured to determine that the patient has failed to comply with the prescribed treatment regimen. In some cases, medical care provider 151 (or another party concerned with the patient's health and well-being, such as a parent, family member, caretaker, healthcare provider) is notified only if the patient has failed to comply with the prescribed treatment regimen. Notification can be provided by reporting conclusion 149 with reporting circuitry 148. Alternatively, or in addition, in some aspects, compliance determination circuitry 144 is configured to determine that the patient has complied with the prescribed treatment regimen, e.g. by generating determination 145. In some aspects, monitoring system 110 reports conclusion 149 with reporting circuitry 148 when the patient is in compliance with the prescribed treatment regimen, as indicated by determination 145. It will be appreciated that in various aspects, compliance determination circuitry can be configured to determine both compliance and non-compliance, and additionally, or alternatively, level of compliance (either at specific levels or simply partial compliance), as indicated by a value of determination 145. Compliance or lack thereof can be represented by appropriate text or numerical value in a displayed report or email e.g., reported by reporting circuitry 148, or represented by a binary value in data stored by data storage circuitry 382. Alternatively, or in addition, level of compliance can be represented by a continuous value (e.g., percent compliance) or a text descriptor selected from a number of text descriptors corresponding to different levels of compliance (e.g., non-compliance, low compliance, intermediate compliance, near-full compliance, full compliance). Reporting circuitry 148 provides for formatting determination 145 appropriately (e.g., by including appropriate messages to accompany the value of the determination) and for deciding whether and how to report the conclusion, based upon user preferences. For example, who is notified (medical care provider versus family member) or how notification is provided (stored in an event record, via email, or via a text message to a cell phone) may depend on the patient's level of compliance and the specifics of the patient. That is reporting circuitry 148 can generate different levels of notifications depending on how serious a problem non-compliance is likely to be for the patient.

In various aspects, reporting circuitry 148 is used to report a conclusion 149 to medical care provider 151 or another party. In an aspect, reporting circuitry 148 includes display device 372. Reporting circuitry 148 may include circuitry for generating a notification. For example, a notification may be displayed on display device 372. Generating a notification may include retrieving a stored notification 374 from data storage device 340, e.g., selected from among one or more notifications stored in data storage device 340, as discussed above in connection with notification circuitry 250 in local system 106. Notifications may take the form of text or numerical codes, for example.

In another aspect, reporting circuitry 148 includes circuitry (e.g., wireless transmitter 378) for transmitting a notification to a wireless device 376. Wireless device 376 may be, for example, a pager, cell phone, or other wireless device used by a medical care provider or family member interested in tracking the status of the patient.

In another aspect, reporting circuitry 148 includes audio alarm circuitry 380 for generating an audio alarm, e.g., a tone or voice alert be delivered via a speaker, or activating a bell, buzzer, beeper, or the like to inform medical care provider 151 of the status of the patient.

In another aspect, reporting circuitry 148 includes data storage circuitry 382 for storing a notification in a data storage device, e.g., in event history 390. For example, data storage circuitry 382 may provide for storage of a notification in event history 390 in conjunction with information regarding the time at which the notification was generated, obtained, for example from timing circuitry 386. In an aspect, timing circuitry 386 includes a clock 388 and/or timer 396. Event history 390 may be a part of the subject's electronic medical records, and may be stored locally in monitoring system 110, or elsewhere.

Systems and system components as illustrated generally in FIGS. 1-3 may be better understood by reference to the examples shown in FIG. 4-7.

Figure 4:
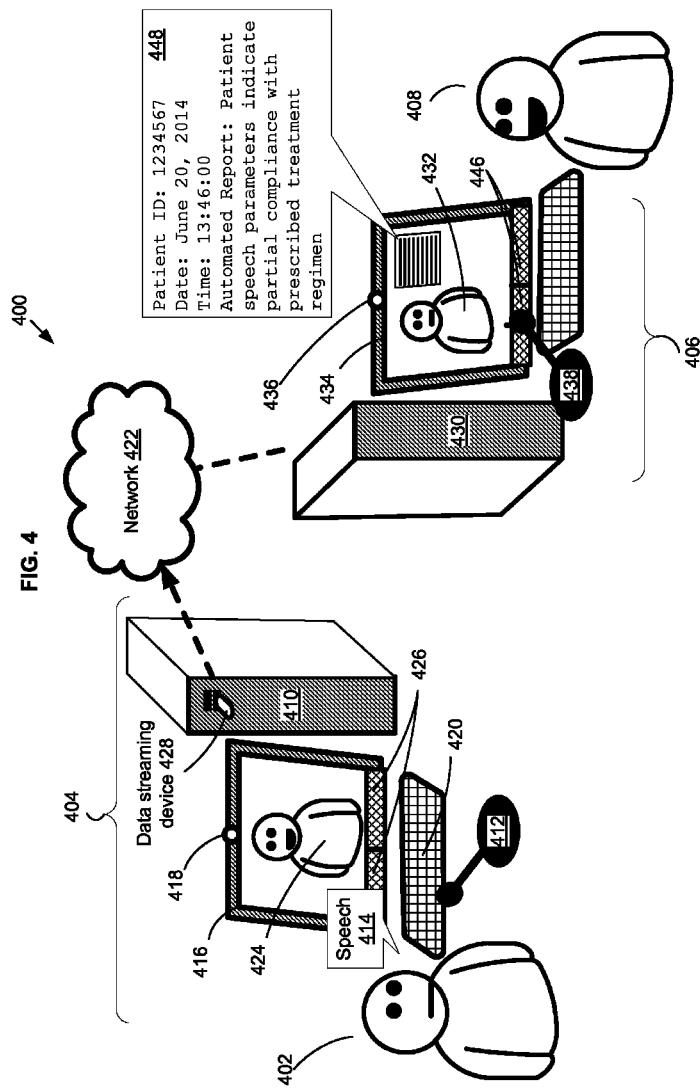
FIG. 4 illustrates an embodiment of a system for monitoring compliance of a patient with a prescribed treatment regimen.

FIG. 4 depicts an embodiment of a system 400 for monitoring compliance of a patient 402 with a prescribed treatment regimen, implemented in connection with the patient's personal computer 410. In an aspect, system 400 is used for monitoring compliance of patient 402 while patient 402 participates in a video consultation with medical care provider 408. In another aspect, system 400 can in addition (or alternatively) be used to monitor compliance of patient 402 during routing activities with data streaming device 428, which is powered by a USB port of computer 410.

System 400 includes system 404 at a patient location and monitoring system 406 used at a monitoring location by a medical care provider 408. System 404 includes a personal computer system including computer 410, microphone 412 for detecting patient speech 414, display 416, camera 418 (which is shown here as being built into display 416, but could also be packaged separately), and keyboard 420.

In the example of FIG. 4, in a first monitoring mode, patient 402 participates in a video consultation with medical care provider 408, with patient voice data being captured by microphone 412, patient image data being captured by camera 418, and both voice and image data being transmitted to computer 430 of monitoring system 406 via network 422. An image 432 of patient 402 is displayed on display 434 for viewing by medical care provider 408. Camera 436 captures an image 424 of medical care provider 408, which is transmitted to system 404 via network 422, where it is displayed on display 416. Microphone 438 captures voice data from medical care provider 408, which is also sent to system 404 and may be delivered to patient 402 via speakers 426. Similar, patient voice data can be presented to medical care provider 408 via speakers 446. In addition to patient image 432, a report 448 containing a conclusion regarding compliance of patient 402 with a prescribed treatment regimen is displayed on display 434. In the example of FIG. 4, report 448 includes a listing of a patient ID number, a date, a time, and a statement regarding patient compliance, e.g., "Patient speech parameters indicate partial compliance with prescribed treatment regimen." Patient identity is determined by entry of an authentication factor (e.g., login and password) by patient 402 when logging in for video conference.

In a second monitoring mode, which is used as the patient is working on computer 410 or in the vicinity, but is not necessarily engaged in a video conference with medical care provider 408, data streaming device 428 captures speech from patient 402 with a built-in microphone and provides for transmission of speech data to network 422. Patient identity is determined by voice recognition. Patient speech data is transmitted from data streaming device 428 to monitoring system 406 via network 422, for processing and reporting to medical care provider 408.

Figure 5:
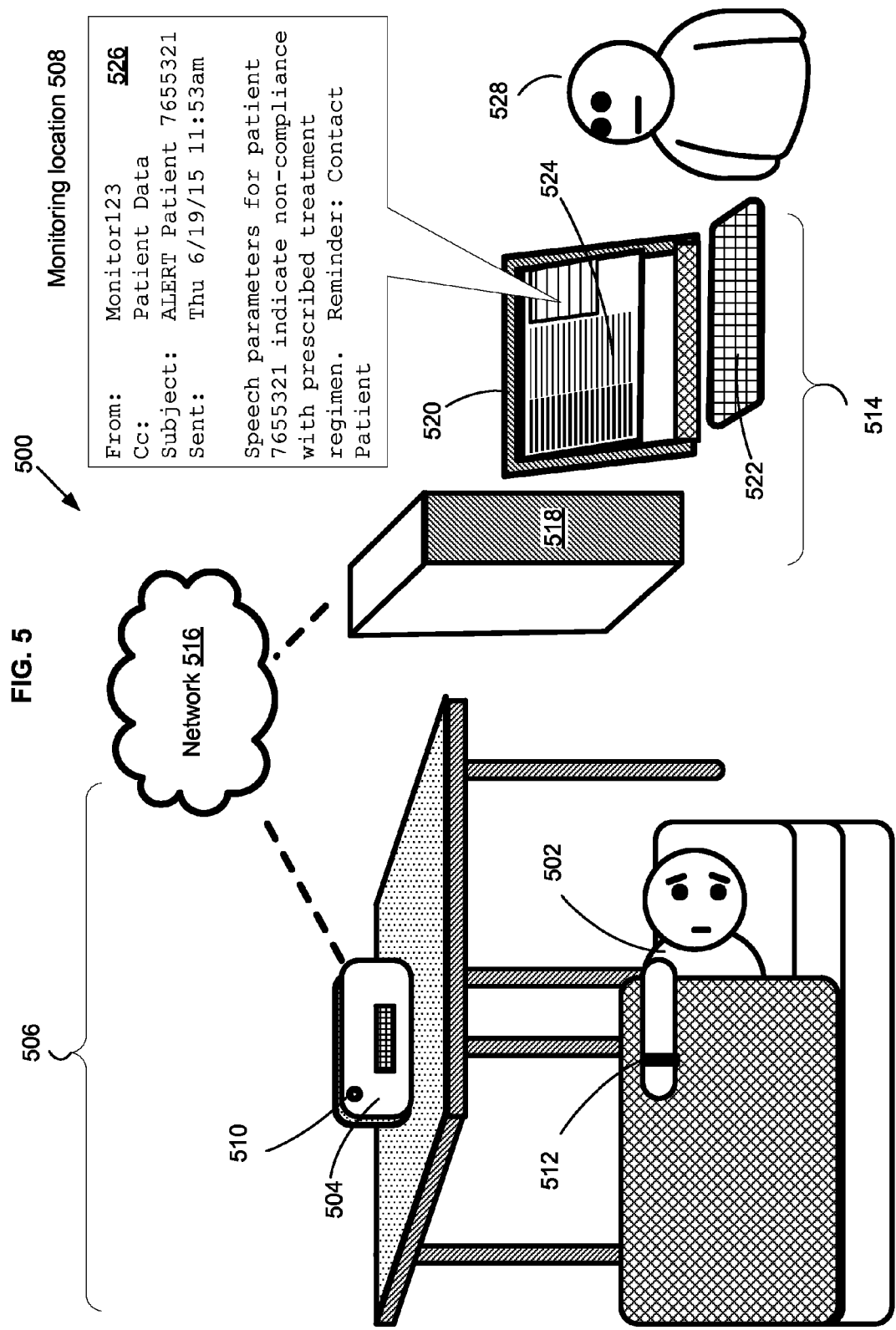
FIG. 5 illustrates another embodiment of a system for monitoring compliance of a patient with a prescribed treatment regimen.

In another example, FIG. 5 depicts a system 500 for monitoring compliance of a patient 502 with a prescribed treatment regimen that includes a stand-alone microprocessor-based device 504 at patient location 506. In an aspect, stand-alone device 504 is configured for easy operation, with minimal user controls. Stand-alone device 504 includes dedicated hardware, firmware and/or software designed to perform the functions described herein. Device 504 is a stand-alone microprocessor-based device in that computing capability at patient location 506 is provided by a dedicated special purpose device and the system does not utilize the computing capability of, e.g., a personal computer or cell phone at the patient location; however, stand-alone device 504 may operate in combination with other system components at the patient location as well as at monitoring location 508. Stand-alone device 504 includes a microphone 510 for sensing patient speech, as well as background sounds. In the example of FIG. 5, patient 502 suffers from depression in which the patient is less active and/or talkative than usual during an episode of the disorder. The content of the patient's speech may also change before or during an episode. Both quantity and content of patient speech may be indicative of the patient's mental state, and hence of the patient's compliance with a prescribed treatment regimen. If patient 502 is present, and microphone 510 detects an audio signal that contains little or no speech or sounds of physical activity of the patient at a time of day when speech or activity would be expected, device 504 generates a report indicating non-compliance of patient 502 with the prescribed treatment regimen. Presence of the patient in the vicinity of device 504, as well as the identity of the patient, can be detected by sensing the presence of an RFID armband 512 worn by patient 502 with an RFID sensor in device 504. Device 504 includes a clock/timing device for tracking the time of day. If non-compliance of the patient with the prescribed treatment regimen is detected, device 504 sends information to computing system 514 at monitoring location 508, via network 516. Computing system 514 includes computer 518, display 520, and keyboard 522. Computer 518 presents information 524, including report 526 concerning patient 502 on display 520, for viewing by medical care provider 528.

Figure 6:
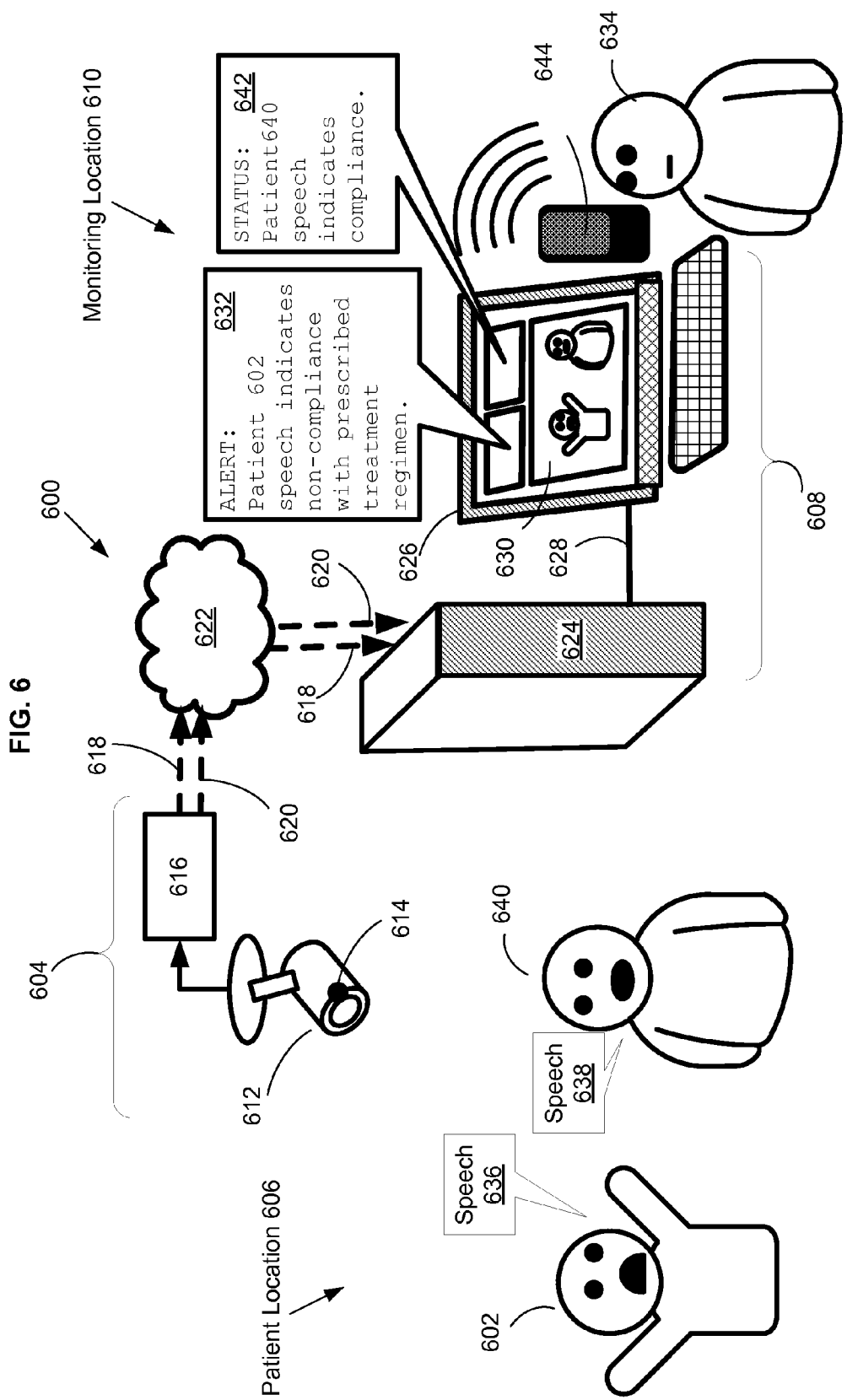
FIG. 6 illustrates another embodiment of a system for monitoring compliance of a patient with a prescribed treatment regimen.

FIG. 6 depicts an example of a system 600 for monitoring patient compliance that is suitable for monitoring a patient 602 in a group setting, for example a group home. System 600 includes a local system 604 in patient location 606, and monitoring system 608 in monitoring location 610. Local system 604 includes imaging device 612, which in this example is a video camera, and microphone 614 connected to circuitry 616. Circuitry 616 transmits a speech data signal 618 containing a speech signal from microphone 614 and identity signal 620 containing a video signal from imaging device 612 to network 622 and from there to monitoring system 608. Circuitry 616 includes conventional closed-circuit TV circuitry that processes speech 636 (e.g., by amplification and filtering) before transmitting it to monitoring system 608. Monitoring system 608 includes computer 624 connected to display 626 by data link 628. Monitoring system 608 can be located in a separate room of a group home from local system 604, connected to local system 604 by a LAN or WAN, for example. Video data contained in identity signal 620 is used to generate image 630, which is displayed on display 626, along with report 632, for viewing by medical care provider 634 (or alternatively, a counselor, or group home staff member, for example). Report 632 is generated by software running on computer 624 based on analysis of speech data signal 618. Speech 636 from patient 602 is separated from speech 638 from second patient 640 based on analysis of identity signal 618. In the present example, analysis of identity signal 618 includes one or both of facial recognition or gait analysis, using methods as discussed herein above. Speech 636 from patient 602 is analyzed to determine whether patient 602 has complied with the prescribed treatment regimen. In the example of FIG. 6, patient 602 exhibits an agitated physical activity pattern (detectable in image 630) and agitated speech pattern (detectable in speech 636), indicating that patient 602 has failed to comply with a prescribed treatment regimen. Accordingly, report 632 states "ALERT: Patient 602 speech indicates non-compliance with prescribed treatment regimen." In addition, an audio alarm (a beep or buzzing sound) is generated on speaker 644 to attract the attention of medical care provider 634. Medical care provider 634 observes the behavior of patient 602 on display 626 in addition to listening to the accompanying audio signal presented on speaker 644. In addition, compliance of patient 640 with a prescribed treatment regimen is also monitored: speech of patient 640 can be detected, separated from the speech of patient 602, analyzed, and compliance reported in the same manner. For example, in FIG. 6, report 642 indicates the status of patient 640: "STATUS: Patient 640 speech indicates compliance."

Figure 7:
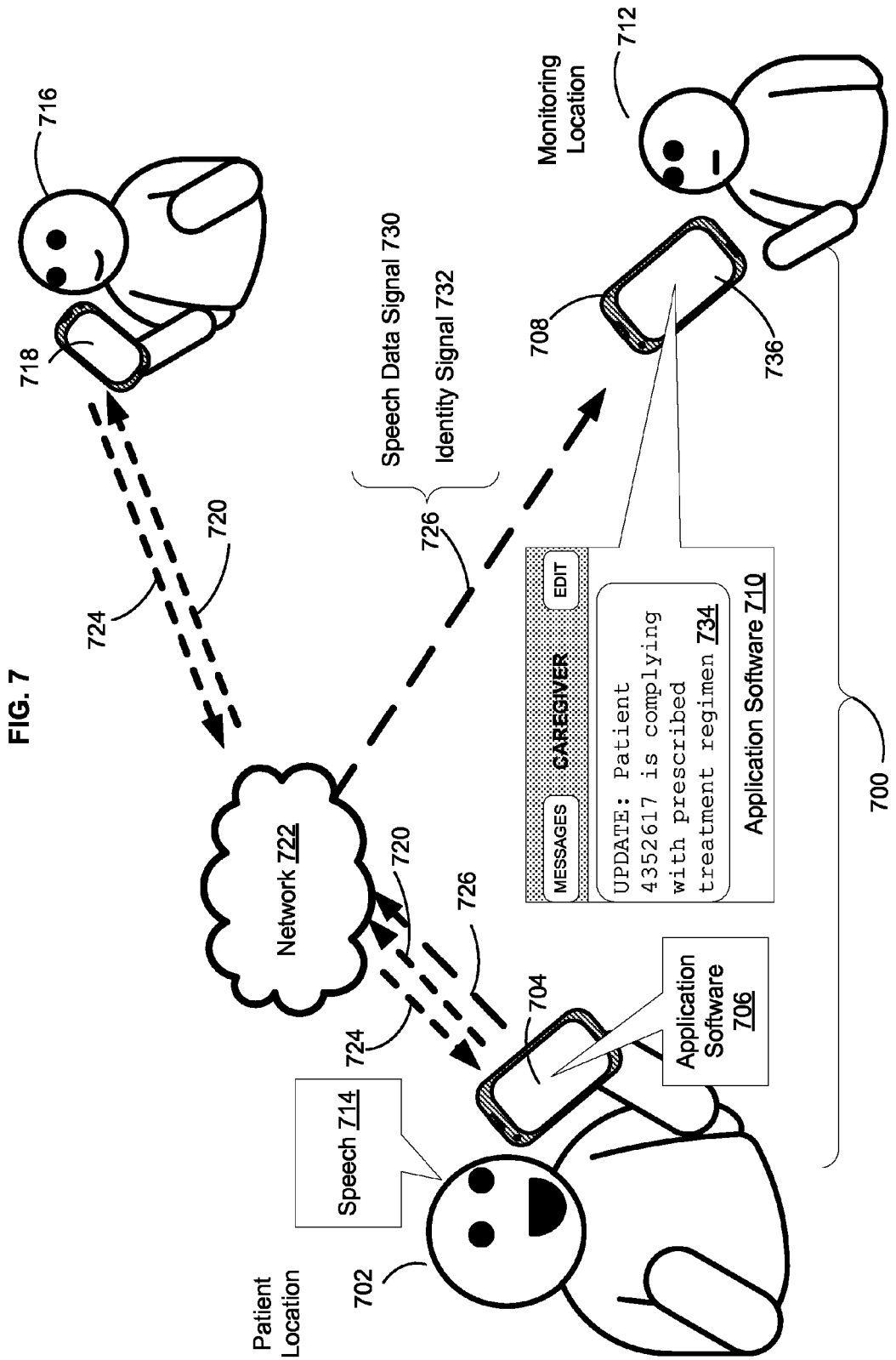
FIG. 7 illustrates another embodiment of a system for monitoring compliance of a patient with a prescribed treatment regimen.

FIG. 7 depicts an example of a system 700 for monitoring compliance of a patient 702 with a treatment regimen. System 700 includes cell phone 704, which is a cell phone used by patient 702, configured with application software 706, and cell phone 708, configured with application software 710, and used by medical care provider 712. System 700 is used to monitor compliance of patient 702 with a prescribed treatment regimen by analyzing speech 714 of patient 702 during the course of routine use of cell phone 704 by patient 702, for example to communicate with person 716 (e.g., a friend) using a cell phone 718. During communication with person 716, a conventional cellular communication signal 720 containing voice data from patient 702 is transmitted to cellular network 722 and from there to cell phone 718. Similarly, cellular communication signal 724 containing voice data from person 716 is transmitted from cell phone 718 to cell phone 704 via cellular network 722. A second cellular signal 726 is transmitted via cellular network 722 to cell phone 708. Second cellular signal 726 contains speech data signal 730 and identity signal 732, which are processed by application software 710 on cell phone 708 to generate report 734. In an aspect, speech data signal 730 contains speech parameters that characterize the speech of patient 702, but not the speech itself, therefore maintaining privacy of patient 702's communications. Furthermore, speech data signal 730 does not contain speech from person 716. Processing of speech data signal 730 occurs on cell phone 704, through the use of application software 706, to perform signal processing functions as described elsewhere herein. As depicted in FIG. 7, report 734 is presented to medical care provider 712 in the form of a text message displayed on screen 736 of cell phone 708.

Figure 8:
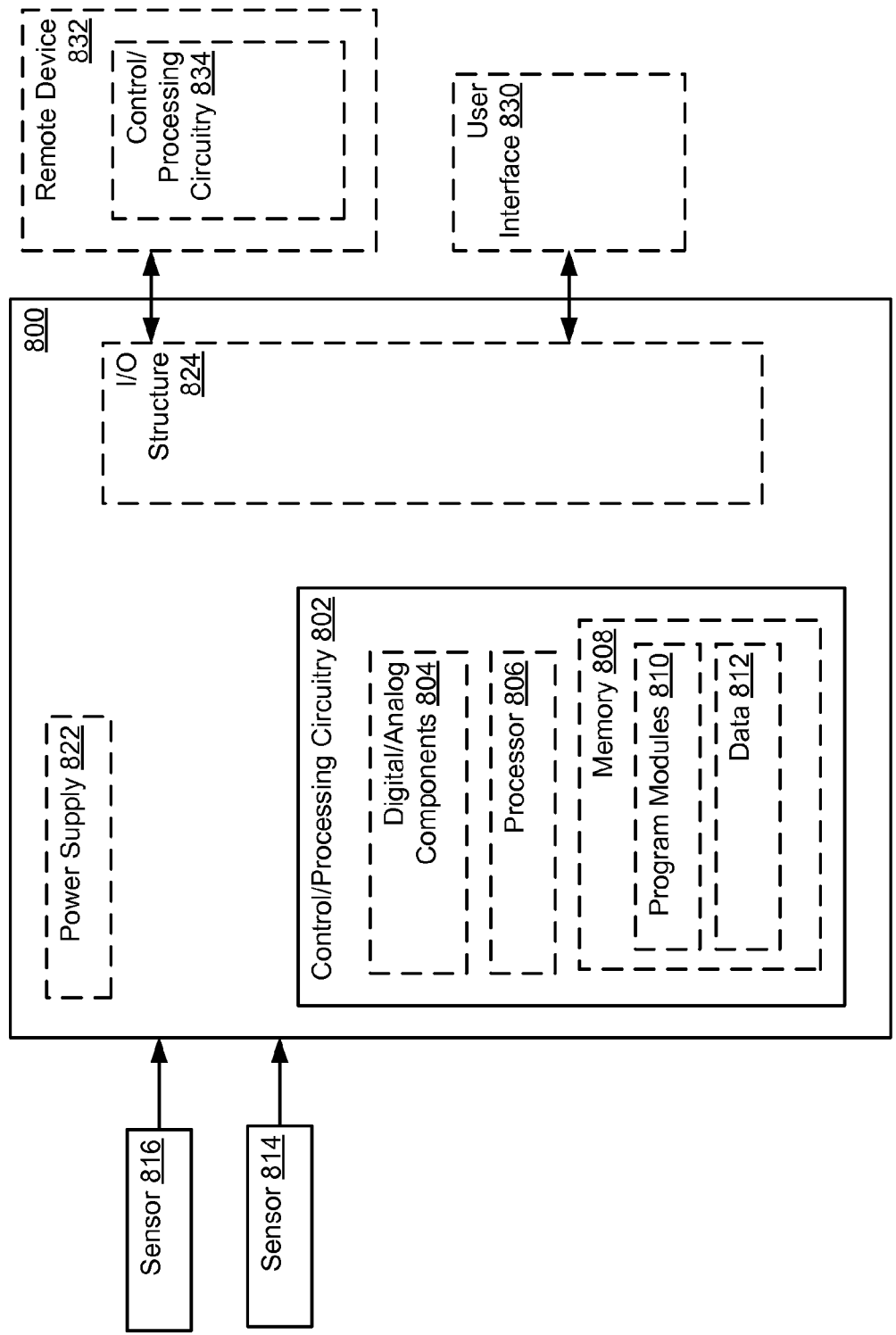
FIG. 8 is a generalized system block diagram.

FIG. 8 illustrates a generalized form of circuitry-based systems as depicted in FIGS. 1-7. Although specific embodiments are described herein, those skilled in the art will appreciate that methods and systems as described herein can be implemented in various ways. Reference is made herein to various circuitry subsystems (e.g., signal processing circuitry 122, compliance determination circuitry 144, and speech identification circuitry 140 in FIGS. 1-3) which may be considered to be control/processing circuitry. As an example of control/processing circuitry 802, local system 105 includes control circuitry for controlling at least one of the at least one audio sensor 114, the signal processing circuitry 122, and the at least one transmitting device 126. Control circuitry of local system 105 in various aspects control other system components and functions, e.g., communication circuitry 284, speech processor 202, notification circuitry 250, as well as data storage, communication, and input/output functions. As an example of control/processing circuitry 832, monitoring system 110 includes control circuitry for controlling at least one of the at least one receiving device 130, the speech identification circuitry 140, the compliance determination circuitry 144, and the reporting circuitry 148, and other system components.

As shown generically in FIG. 8, control/processing circuitry 802 includes any or all of digital and/or analog components 804, one or more processor 806 (e.g., a microprocessor), and memory 808, which may store one or more program module 810 and/or data 812. Systems as described herein may receive signals from various sensors (e.g., sensors 814 and 816 depicted in FIG. 8). System 800 may include other components as known to those skilled in the art, e.g., one or more power supply 822, and I/O structure 824. I/O structure 824 permits communication with various types of user interface devices (represented by user interface 830) and various types of remote device 832, which may have control/processing capability conferred by control/processing circuitry 834.

In a general sense, those skilled in the art will recognize that the various embodiments described herein can be implemented, individually and/or collectively, by various types of electrical circuitry having a wide range of electrical components such as hardware, software, firmware, and/or virtually any combination thereof. Electrical circuitry (including signal processing circuitry 122, speech identification circuitry 140, and compliance determination circuitry 144 in FIG. 1, for example) includes electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device, which may include various types of memory (e.g., random access, flash, read only, etc.), electrical circuitry forming a communications device (e.g., transmitting device 126 and receiving device 130) (e.g., a modem, communications switch, optical-electrical equipment, etc.), and/or any non-electrical analog thereto, such as optical or other analogs (e.g., graphene based circuitry). In a general sense, those skilled in the art will recognize that the various aspects described herein which can be implemented, individually and/or collectively, by a wide range of hardware, software, firmware, and/or any combination thereof can be viewed as being composed of various types of "electrical circuitry."

Those skilled in the art will recognize that at least a portion of the devices and/or processes described herein can be integrated into a data processing system. Those having skill in the art will recognize that a data processing system generally includes one or more of a system unit housing, a video display, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

As discussed in connection with FIG. 1, transmitting device 126 in local system 106 and receiving device 130 in monitoring system 110 are configured to provide a communication link between the two locations. In various aspects, transmitting device 126 and receiving device 130 provide a wireless communication link. A wireless communication link may also be established between monitoring system 110 and wireless device 376, as shown in FIG. 3. In various aspects, a wireless communication link includes at least one of a radio frequency, wireless network, cellular network, satellite, WiFi, BlueTooth, Wide Area Network, Local Area Network, or Body Area Network communication link. Various types of communication links are suitable for providing communication between two remote locations. Communication between locations remote from each other may take place over telecommunications networks, for example public or private Wide Area Network (WAN). In general, communication between remote locations is not considered to be suitably handled by technologies geared towards physically localized networks, e.g., Local Area Network (LAN) technologies operation at Layer ½ (such as the forms of Ethernet or WiFi). However, it will be appreciated that portions (but not the entirety) of communication networks used in remote communications may include technologies suitable for use in physically localized network, such as Ethernet or WiFi. In an aspect, system components are considered "remote" from each other if they are not within the same room, building, or campus. In an aspect, a remote system may include components separated by a few miles or more. Conversely, system components may be considered "local" to each other if they are located within the same room, building, or campus.

Figure 9:
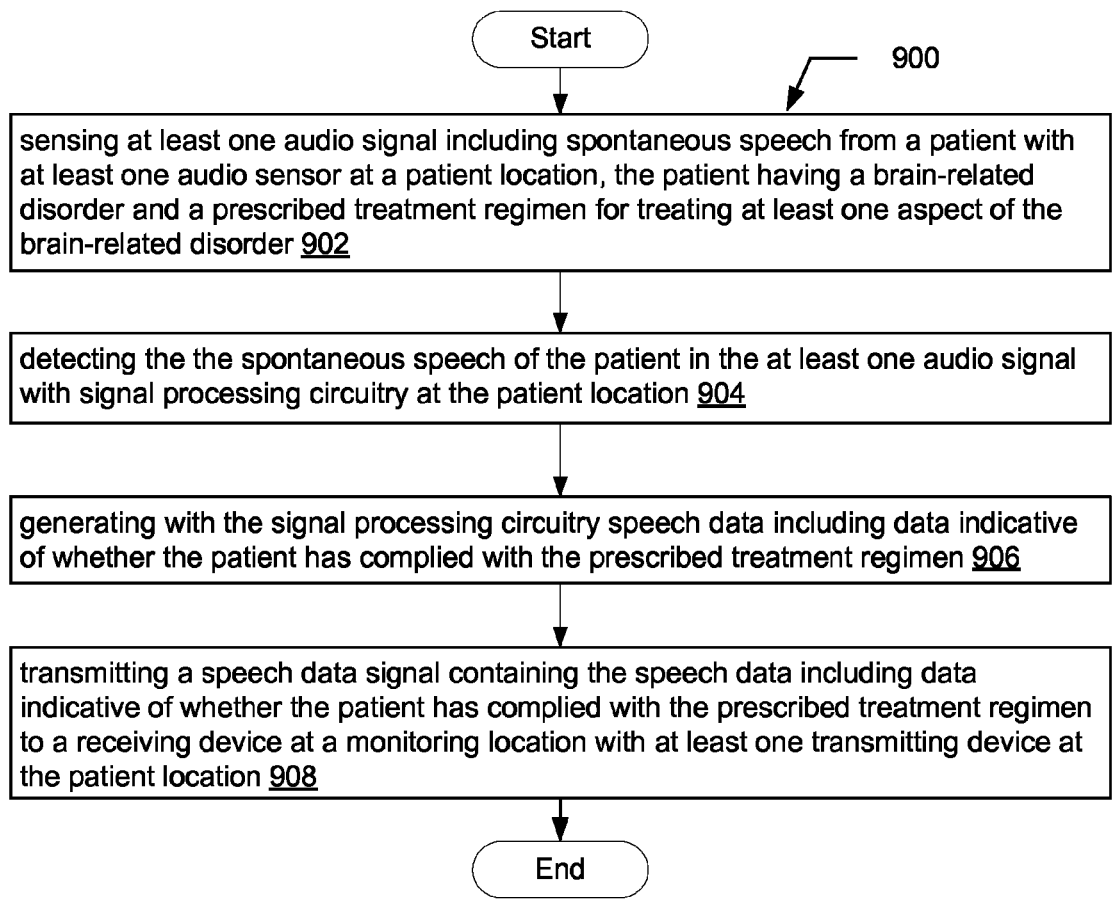
FIG. 9 is a flow diagram of a method of monitoring compliance of patient with a prescribed treatment regimen.

FIG. 9 is a flow diagram of a method 900 relating to monitoring of a patient at a patient location to determine compliance of the patient with a prescribed treatment regimen. Method 900 includes sensing at least one audio signal including spontaneous speech from a patient with at least one audio sensor at a patient location, the patient having a brain-related disorder and a prescribed treatment regimen for treating at least one aspect of the brain-related disorder, as indicated at 902; detecting spontaneous speech of the patient in the at least one audio signal with signal processing circuitry at the patient location, as indicated at 904; generating with the signal processing circuitry speech data including data indicative of whether the patient has complied with the prescribed treatment regimen, as indicated at 906; and transmitting a speech data signal containing the speech data including data indicative of whether the patient has complied with the prescribed treatment regimen to a receiving device at a monitoring location with at least one transmitting device at the patient location, as indicated at 908. Generation of a speech data signal containing speech data including data indicative of whether the patient has complied with the prescribed treatment regimen is carried out with a system as depicted in FIG. 2

FIGS. 10-18 depict variations and expansions of method 900 as shown in FIG. 9. In the methods depicted in FIGS. 10-18, steps 902-908 are as described generally in connection with FIG. 9. Here and elsewhere, method steps outlined with dashed lines represent steps that are included in some, but not all method aspects, and combinations of steps other than those specifically depicted in the figures are possible as would be known by those having ordinary skill in the relevant art.

Figure 10:
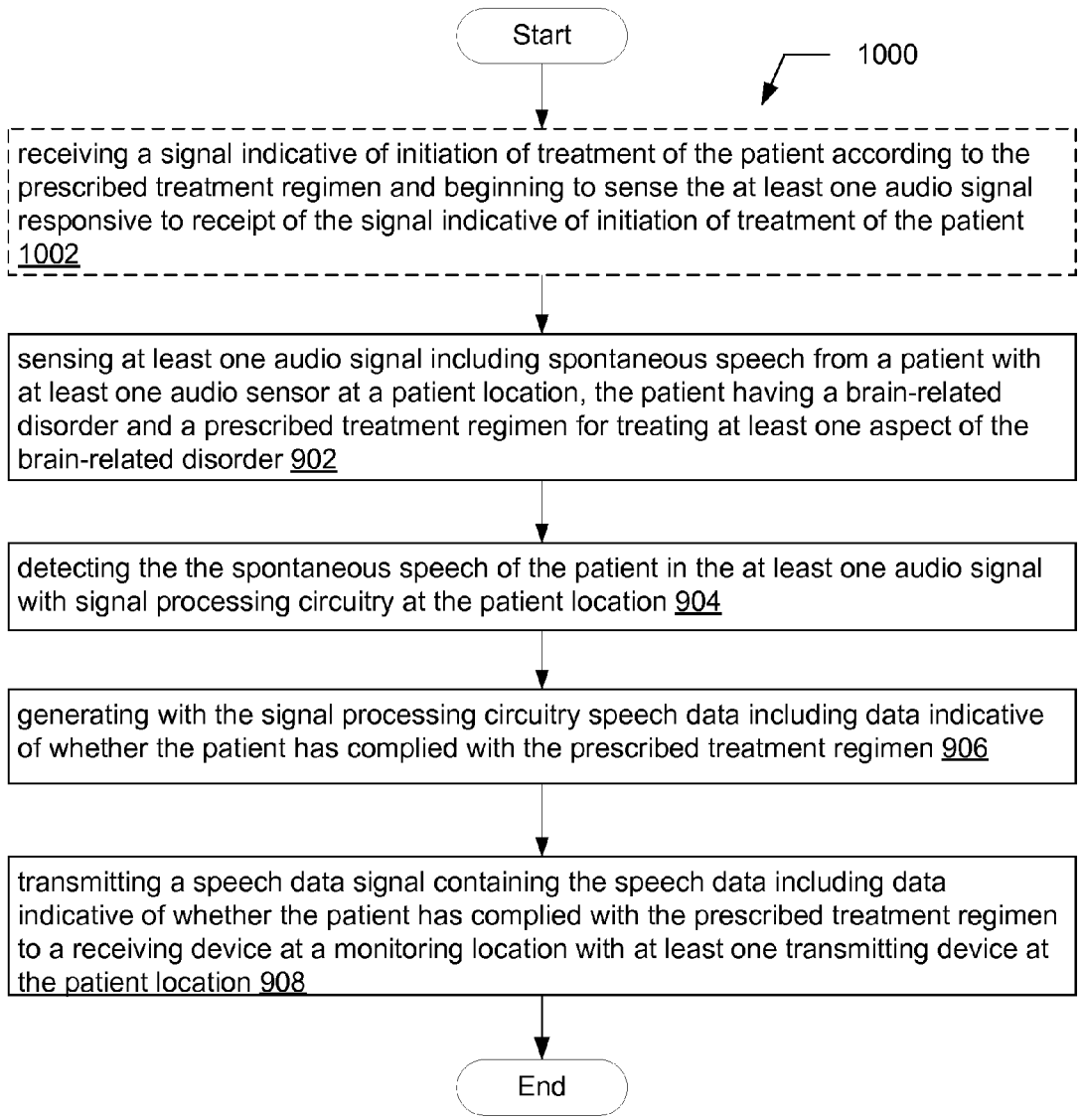
FIG. 10 is a flow diagram of further aspects of the method of FIG. 9.

FIG. 10 depicts method 1000, which includes steps 902-908 as described above, and also includes receiving a signal indicative of initiation of treatment of the patient according to the prescribed treatment regimen and beginning to sense the at least one audio signal responsive to receipt of the signal indicative of initiation of treatment of the patient, as indicated at 1002. As shown in FIG. 2, in an aspect a treatment signal 272 is transmitted to local system 106 from monitoring system 110, in response to an input indicating initiation of treatment from medical care provider 151, provided via a user input device (e.g., a keyboard or keypad), for example. In some aspects, patient 102 may provide an input via a user input device (e.g., a keyboard or keypad) to indicate that treatment has been initiated (e.g., that the patient took a dose of medication).

Figure 11:
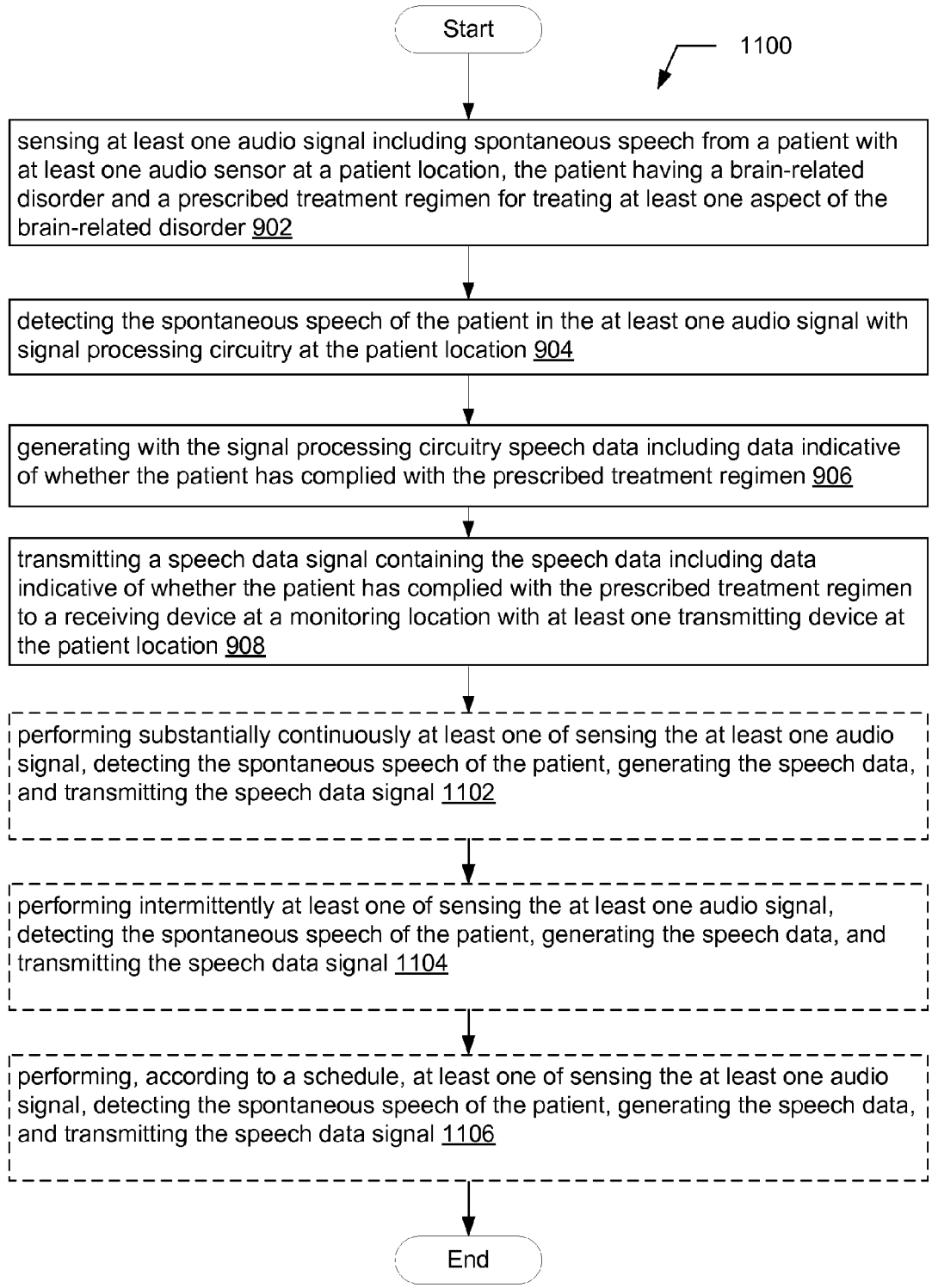
FIG. 11 is a flow diagram of further aspects of the method of FIG. 9.

FIG. 11 depicts a further method 1100, which includes performing substantially continuously at least one of sensing the at least one audio signal, detecting the spontaneous speech of the patient, generating the speech data, and transmitting the speech data signal, as indicated at 1102. Continuous monitoring may be appropriate, for example, in situations where the patient's condition is unstable and likely to change abruptly or dramatically, such that prompt detection and correction is desirable. In an aspect, method 1100 includes performing intermittently at least one of sensing the at least one audio signal, detecting the spontaneous speech of the patient, generating the speech data, and transmitting the speech data signal, as indicated at 1104. Intermittent sensing may be appropriate for patients whose condition is sufficiently stable that continuous monitoring is not required. Intermittent sensing may be event driven (for example, sensing can be performed when the patient uses a phone for communication, or when the patient uses a personal computer). In another aspect, method 1100 includes performing, according to a schedule, at least one of sensing the at least one audio signal, detecting the spontaneous speech of the patient, generating the speech data, and transmitting the speech data signal, as indicated at 1106. Sensing can be performed according to a schedule, under control of timing circuitry 244 in local system 106, as shown in FIG. 2. Timing circuitry 244 includes clock 274 and/or timer 276 and controls sensing according to stored schedule 278, for example by sending an interrupt to initiate sensing at the time or times specified by schedule 278, based on time from clock 274/timer 276. Similarly, timing may be controlled by timing circuitry 386 in monitoring system 110, according to schedule 398, based on time from clock 388 and/or timer 396.

Figure 12:
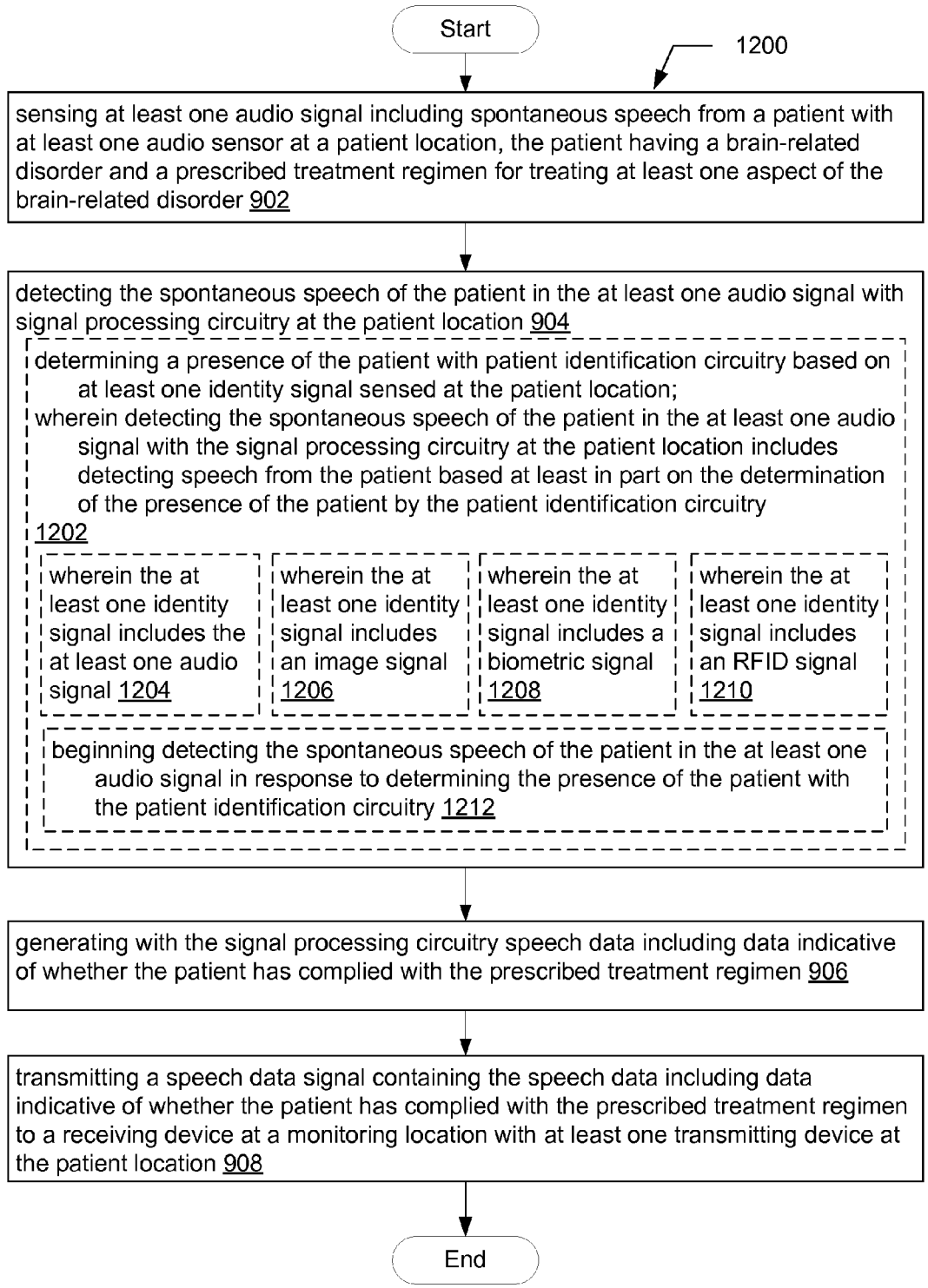
FIG. 12 is a flow diagram of further aspects of the method of FIG. 9.

As shown in FIG. 12, in another aspect, method 1200 includes determining a presence of the patient with patient identification circuitry based on at least one identity signal sensed at the patient location, wherein detecting spontaneous speech of the patient in the at least one audio signal with the signal processing circuitry at the patient location includes detecting speech from the patient based at least in part on the determination of the presence of the patient by the patient identification circuitry, as indicated at 1202. The identity signal may include, for example, the audio signal, as indicated at 1204; an image signal, as indicated at 1206; a biometric signal, as indicated at 1208; or an RFID signal, as indicated at 1210. In an aspect, method 1200 includes beginning detecting the spontaneous speech of the patient in the at least one audio signal in response to determining the presence of the patient with the patient identification circuitry, as indicated at 1212. For example, in the embodiment of FIG. 6, in an aspect, detection of spontaneous speech from patient 602 is initiated in response to determining the presence of patient 602 based on recognition of patient 602 in image 630, using one or both of gait or facial recognition techniques.

Figure 13:
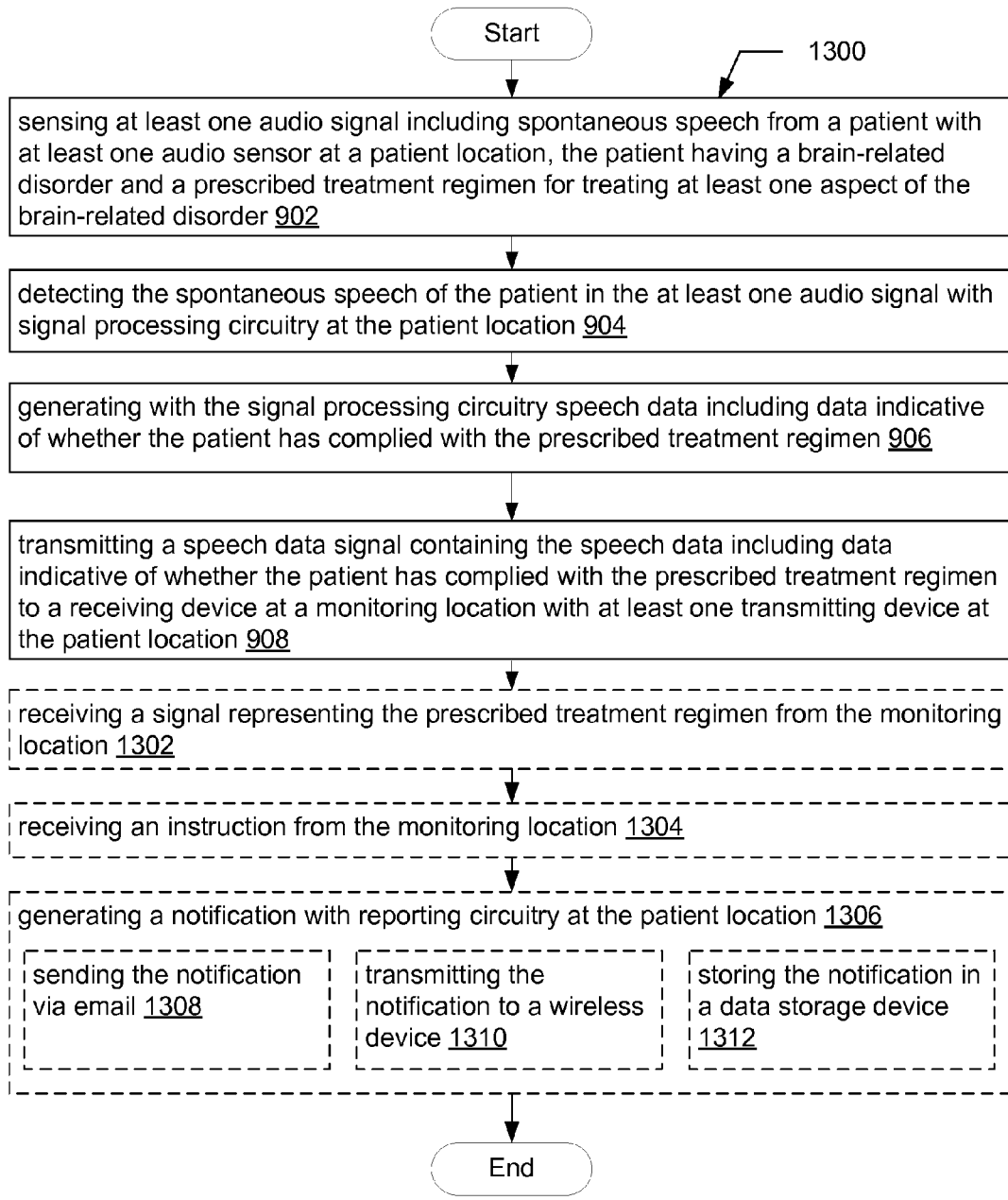
FIG. 13 is a flow diagram of further aspects of the method of FIG. 9.

As shown in FIG. 13, in various aspects a method 1300 includes receiving a signal representing the prescribed treatment regimen from the monitoring location, as indicated at 1302 (e.g., prescription information signal 338 in FIGS. 2 and 3); receiving an instruction from the monitoring location, as indicated at 1304 (e.g., instruction 399 in FIGS. 2 and 3); and generating a notification with notification circuitry at the patient location, as indicated at 1306; and may also include one or more of sending the notification via email, as indicated at 1308; transmitting the notification to a wireless device, as indicated at 1310; and storing the notification in a data storage device, as indicated at 1312 (see, e.g., discussion of notification generation by notification circuitry 250 in FIG. 2).

Figure 14:
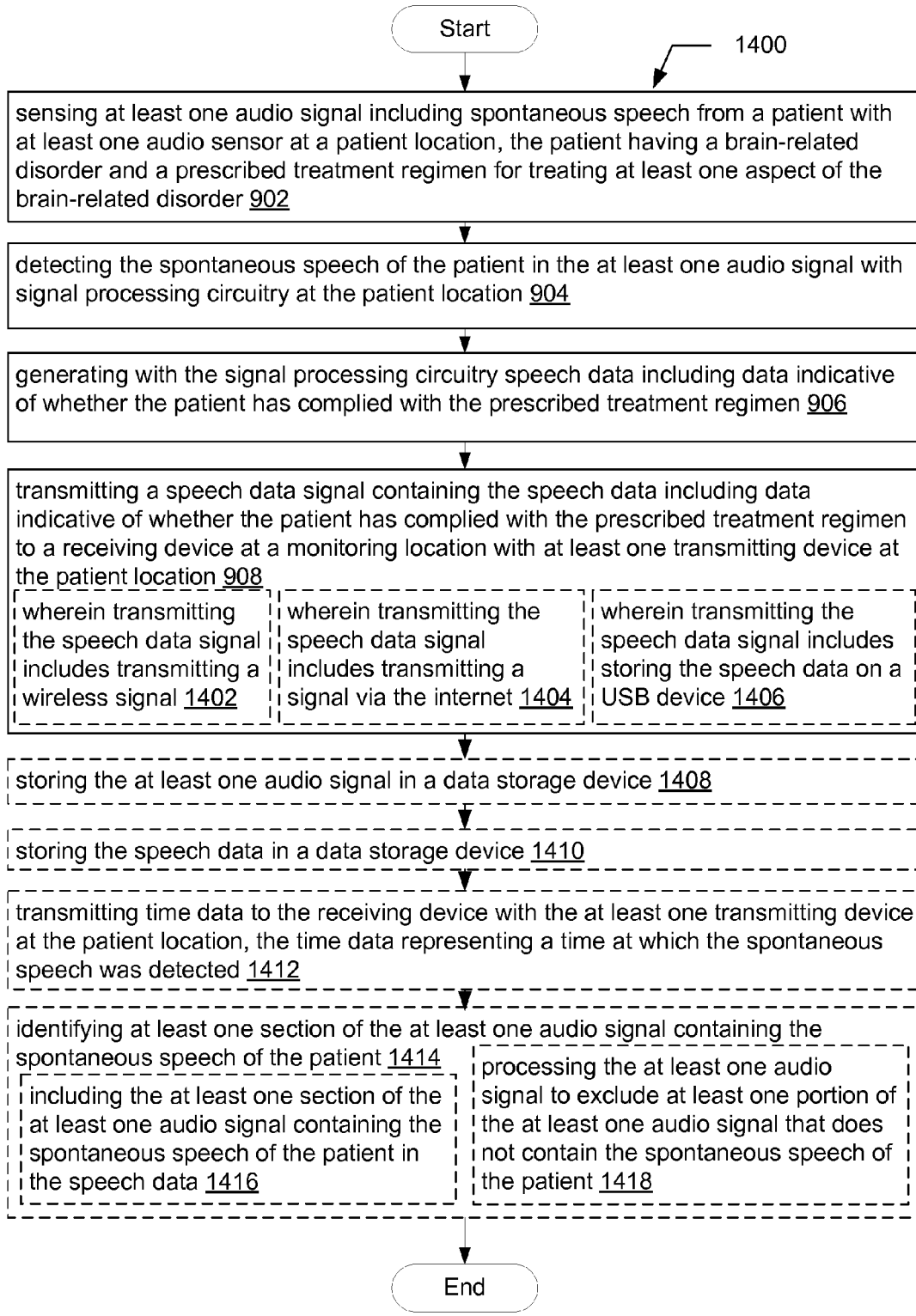
FIG. 14 is a flow diagram of further aspects of the method of FIG. 9.

As shown in FIG. 14, in various aspects of a method 1400, transmitting the speech data signal includes transmitting a wireless signal, as indicated at 1402; transmitting a signal via the internet, as indicated at 1404; or storing the speech data on a USB device, as indicated at 1406. See, e.g., transmitting device 126, as depicted and described in connection with FIG. 2. Method 1400 may include storing the at least one audio signal in a data storage device, as indicated at 1408; storing the speech data in a data storage device, as indicated at 1410 (e.g., data storage device 200 in FIG. 2); or transmitting time data to the receiving device with the at least one transmitting device at the patient location, the time data representing a time at which the spontaneous speech was detected, as indicated at 1412. Method 1400 may include identifying at least one section of the at least one audio signal containing spontaneous speech of the patient, as indicated at 1414. Method 1400 may then also include one or both of including the at least one section of the at least one audio signal containing spontaneous speech of the patient in the speech data, as indicated at 1416, and processing the at least one audio signal to exclude at least one portion of the at least one audio signal that does not contain the spontaneous speech of the patient, as indicated at 1418.

Figure 15:
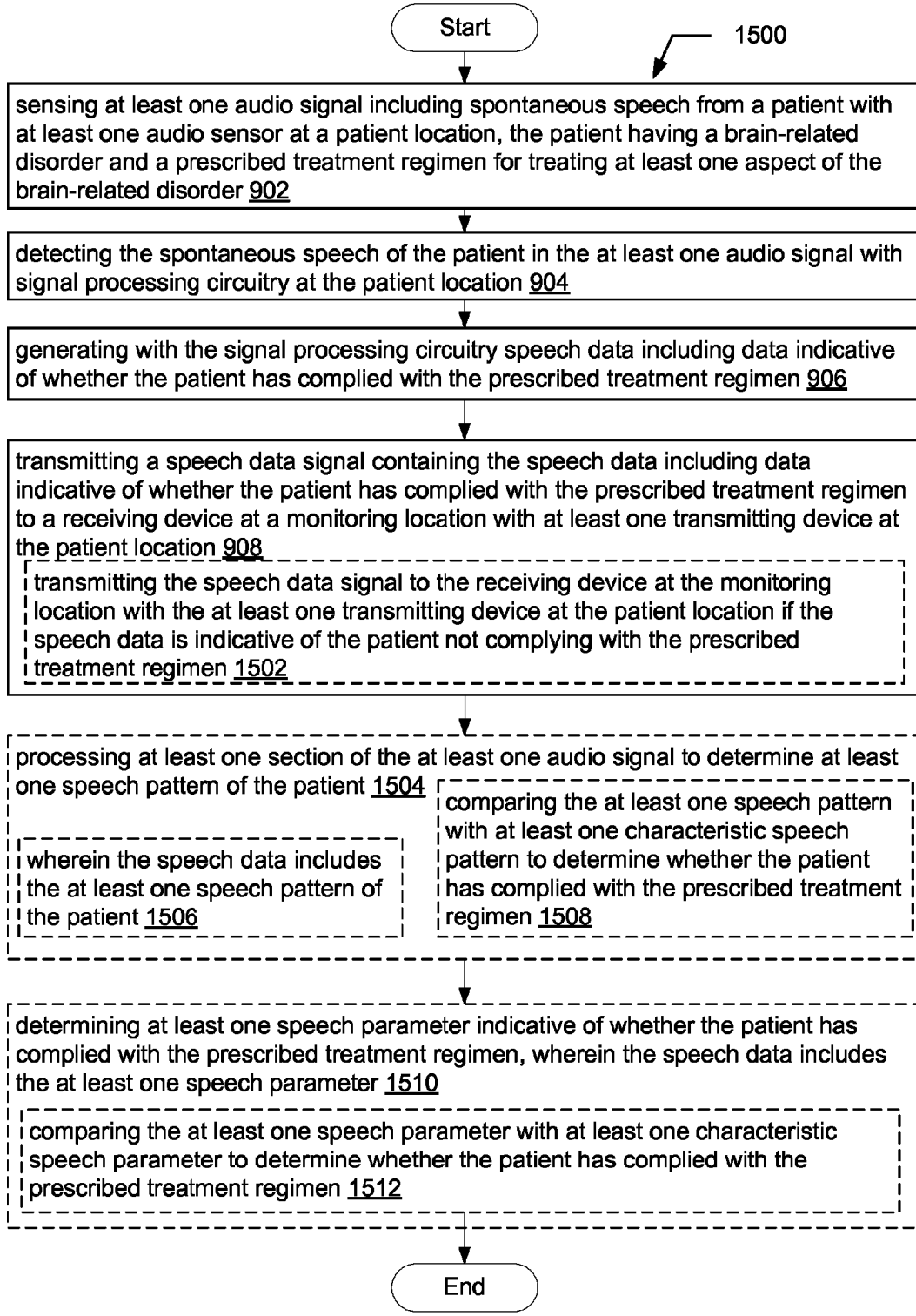
FIG. 15 is a flow diagram of further aspects of the method of FIG. 9.

FIG. 15 depicts a method 1500, which in an aspect includes transmitting the speech data signal to the receiving device at the monitoring location with the at least one transmitting device at the patient location if the speech data is indicative of the patient not complying with the prescribed treatment regimen, as indicated at 1502. Such a notification allows a medical care provider to take action to correct or respond to the patient's lack of compliance when such notification is received, without the need for the medical care provider to monitor the patient's status continuously. In addition, in an aspect, method 1500 includes processing at least one section of the at least one audio signal to determine at least one speech pattern of the patient, as indicated at 1504. The speech data may then include the at least one speech pattern of the patient, as indicated at 1506. In addition, method 1500 may also include comparing the at least one speech pattern with at least one characteristic speech pattern to determine whether the patient has complied with the prescribed treatment regimen, as indicated at 1508.

In another aspect, method 1500 includes determining at least one speech parameter indicative of whether the patient has complied with the prescribed treatment regimen, wherein the speech data includes the at least one speech parameter, as indicated at 1510, and may then also include comparing the at least one speech parameter with at least one characteristic speech parameter to determine whether the patient has complied with the prescribed treatment regimen, as indicated at 1512.

Figure 16:
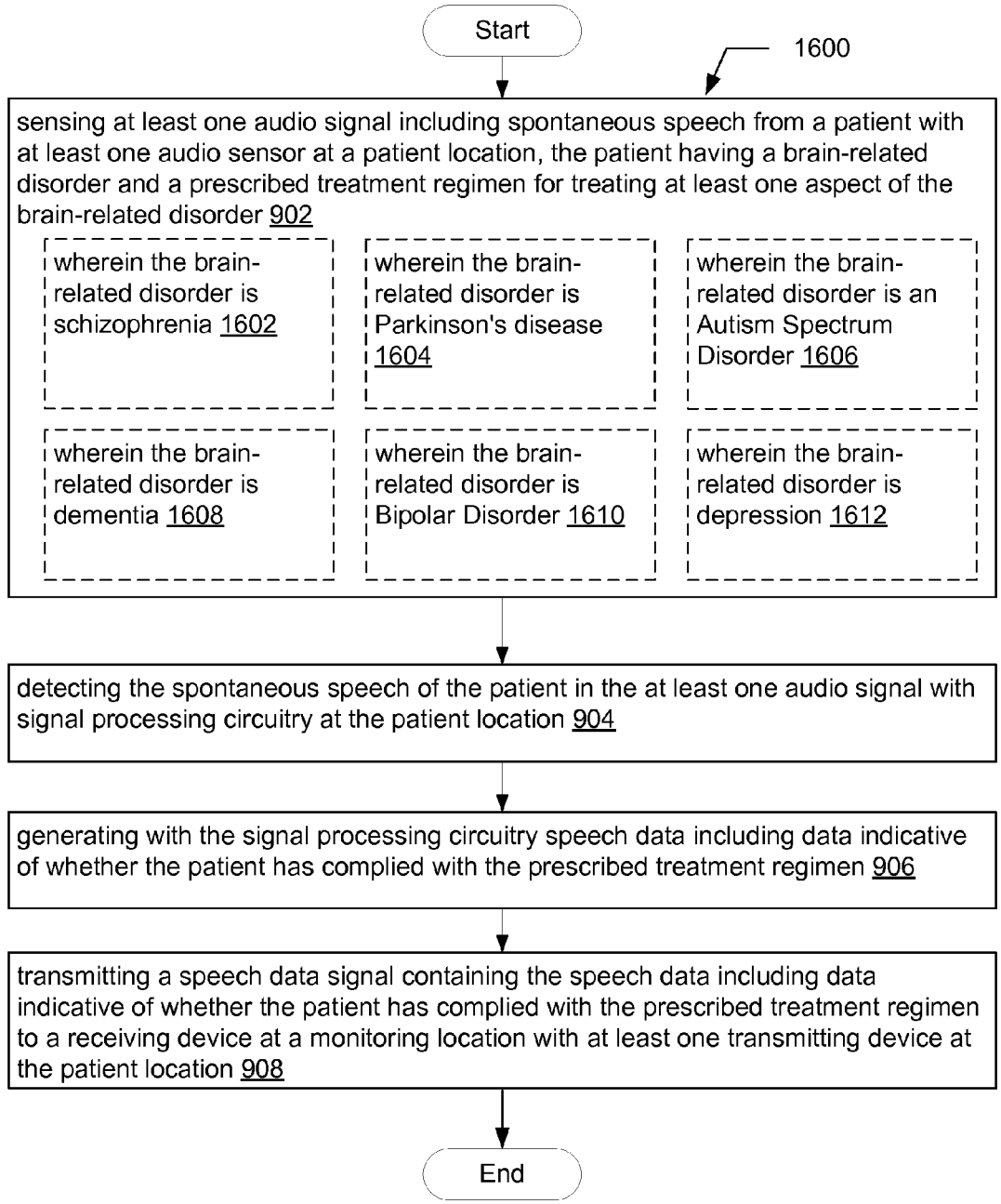
FIG. 16 is a flow diagram of further aspects of the method of FIG. 9.

As shown in FIG. 16, various aspects of a method 1600, the brain-related disorder is schizophrenia, as indicated at 1602; Parkinson's disease, as indicated at 1604; an Autism Spectrum Disorder, as indicated at 1606; dementia, as indicated at 1608; Bipolar Disorder, as indicated at 1610; or depression, as indicated at 1612.

In an aspect a brain-related disorder is a mental disorder, psychological disorder, or psychiatric disorder. A mental disorder, psychological disorder, or psychiatric disorder can include, for example, a psychological pathology, psychopathology, psychosocial pathology, social pathology, or psychobiology disorder. A mental disorder, psychological disorder, or psychiatric disorder can be any disorder categorized in any Diagnostic and Statistical Manual (DSM) or International Statistical Classification of Diseases (ICD) Classification of Mental and Behavioural Disorders text, and may be, for example and without limitation, a neurodevelopmental disorder (e.g., autism spectrum disorder or attention-deficit/hyperactivity disorder), a psychotic disorder (e.g., schizophrenia), a mood disorder, a bipolar disorder, a depressive disorder, an anxiety disorder, an obsessive-compulsive disorder, a trauma- or stressor-related disorder, a dissociative disorder, a somatic symptom disorder, an eating disorder, an impulse-control disorder, a substance-related or addictive disorder, a personality disorder (e.g., narcissistic personality disorder or antisocial personality disorder), a neurocognitive disorder, a major or mild neurocognitive disorder (e.g., one due to Alzheimer's disease, traumatic brain injury, HIV infection, prion disease, Parkinson's disease, Huntington's disease, or substance/medication). A mental disorder, psychological disorder, or psychiatric disorder can be any disorder described by the NIH National Institute of Mental Health (NIMH) Research Domain Criteria Project and may include a biological disorder involving brain circuits that implicate specific domains of cognition, emotion, or behavior. In an aspect, a brain-related disorder includes a serious mental illness or serious emotional disturbance.

In various aspects, a brain-related disorder includes a serious mental illness or serious emotional disturbance, a mental disorder, psychological disorder, or psychiatric disorder.

In an aspect a brain disorder is a traumatic disorder, such as a traumatic brain injury. Traumatic brain injury-induced disorders may present with dysfunction in cognition, communication, behavior, depression, anxiety, personality changes, aggression, acting out, or social inappropriateness. See, e.g., Jeffrey Nicholl and W. Curt LaFrance, Jr., "Neuropsychiatric Sequelae of Traumatic Brain Injury," Semin Neurol. 2009, 29(3):247-255.

In an aspect a brain-related disorder is a lesion-related disorder. A brain lesion can include, for example and without limitation, a tumor, an aneurysm, ischemic damage (e.g., from stroke), an abscess, a malformation, inflammation, or any damage due to trauma, disease, or infection. An example of a lesion-related disorder is a disorder associated with a right-hemisphere lesion.

In an aspect a brain disorder is a neurological disorder. A neurological disorder may be, for example and without limitation, Alzheimer's disease, a brain tumor, a developmental disorder, epilepsy, a neurogenetic disorder, Parkinson's disease, Huntington's disease, a neurodegenerative disorder, stroke, traumatic brain injury or a neurological consequence of AIDS. Neurological disorders are described on the website of the National Institutes of Health (NIH) National Institute of Neurological Disorders and Stroke (NINDS)

Figure 17:
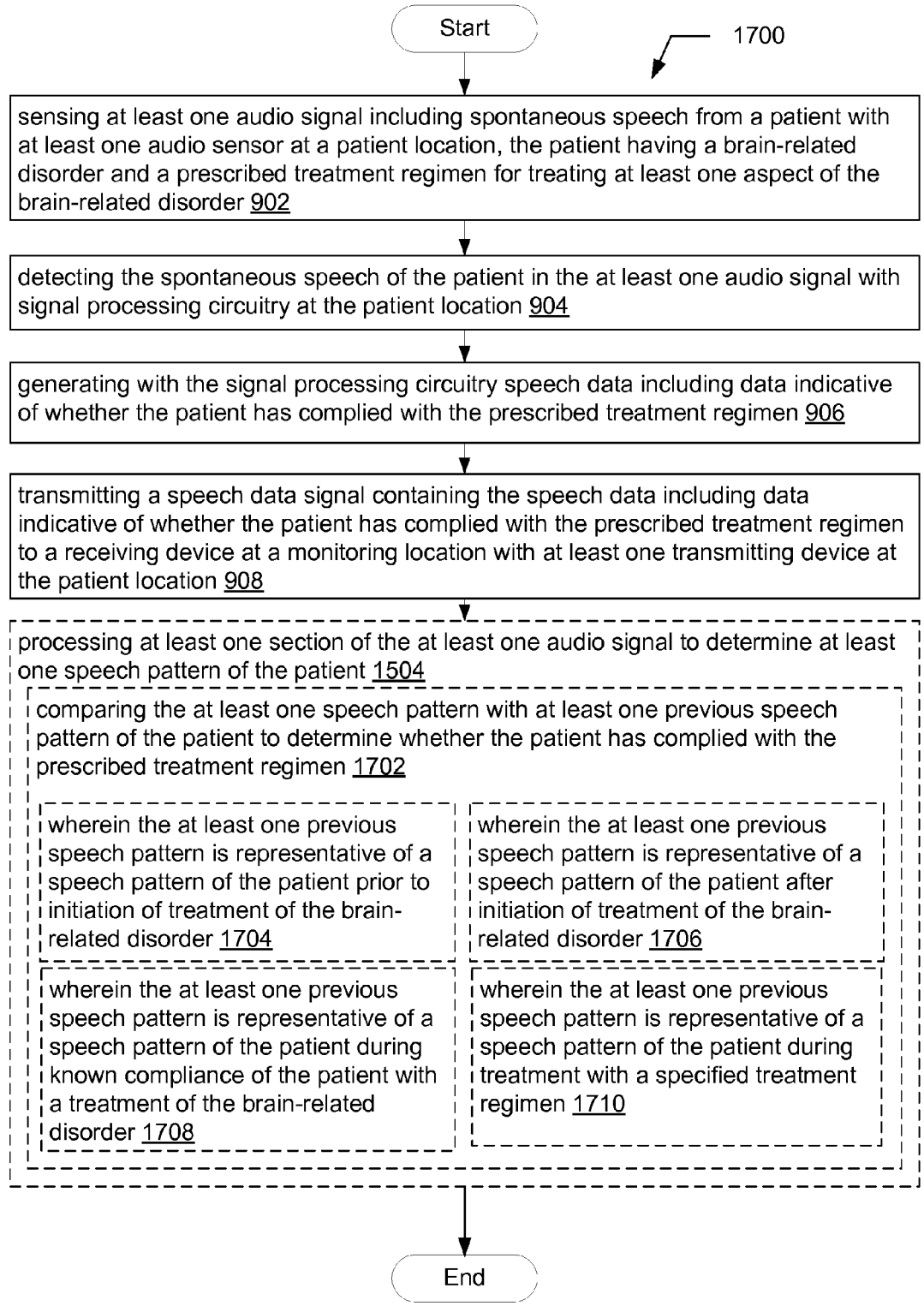
FIG. 17 is a flow diagram of further aspects of the method of FIG. 9.

FIG. 17 shows a method 1700 that includes processing at least one section of the at least one audio signal to determine at least one speech pattern of the patient, as indicated at 1504, and in addition, comparing the at least one speech pattern with at least one previous speech pattern of the patient to determine whether the patient has complied with the prescribed treatment regimen, as indicated at 1702. For example, in various aspects, the at least one previous speech pattern is representative of a speech pattern of the patient prior to initiation of treatment of the brain-related disorder, as indicated at 1704; a speech pattern of the patient after initiation of treatment of the brain-related disorder, as indicated at 1706; a speech pattern of the patient during known compliance of the patient with a treatment of the brain-related disorder, as indicated at 1708; or a speech pattern of the patient during treatment with a specified treatment regimen, as indicated at 1710.

Figure 18:
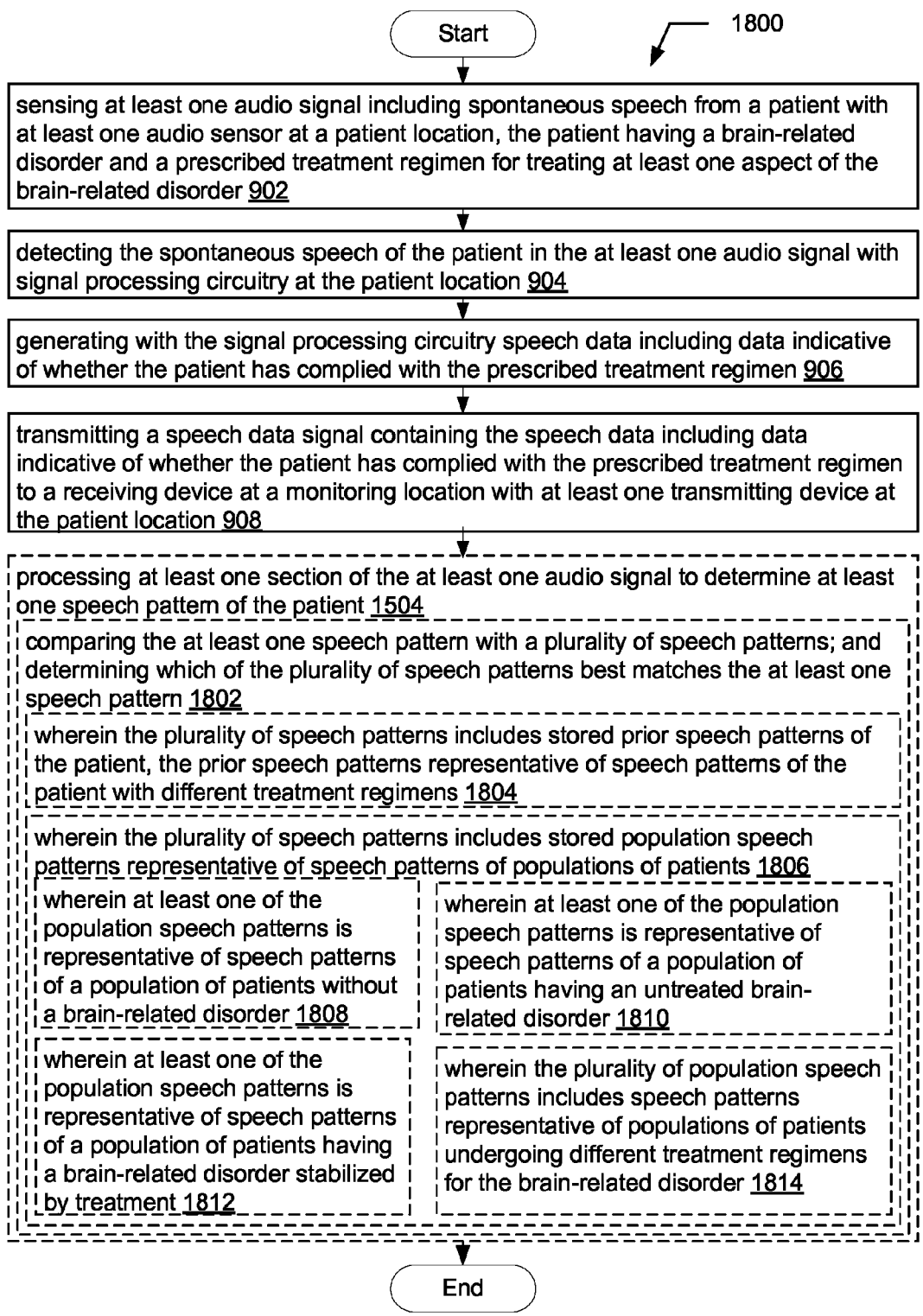
FIG. 18 is a flow diagram of further aspects of the method of FIG. 9.

As shown in FIG. 18, in an aspect, a method 1800 includes processing at least one section of the at least one audio signal to determine at least one speech pattern of the patient, as indicated at 1504, and in addition, comparing the at least one speech pattern with a plurality of speech patterns and determining which of the plurality of speech patterns best matches the at least one speech pattern, as indicated at 1802. In an aspect, the plurality of speech patterns includes stored prior speech patterns of the patient, the prior speech patterns representative of speech patterns of the patient with different treatment regimens, as indicated at 1804. In another aspect, the plurality of speech patterns includes stored population speech patterns representative of speech patterns of populations of patients, as indicated at 1806. In various aspects, at least one of the population speech patterns is representative of speech patterns of a population of patients without a brain-related disorder, as indicated at 1808; a population of patients having an untreated brain-related disorder, as indicated at 1810; or a population of patients having a brain-related disorder stabilized by treatment, as indicated at 1812. In an aspect, the plurality of population speech patterns includes speech patterns representative of populations of patients undergoing different treatment regimens for a brain-related disorder, as indicated at 1814.

In various embodiments, methods as described herein may be performed according to instructions implementable in hardware, software, and/or firmware. Such instructions may be stored in non-transitory machine-readable data storage media, for example. Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware in one or more machines, compositions of matter, and articles of manufacture. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically oriented hardware, software, and or firmware.

In some implementations described herein, logic and similar implementations may include software or other control structures. Electrical circuitry, for example, may have one or more paths of electrical current constructed and arranged to implement various functions as described herein. In some implementations, one or more media may be configured to bear a device-detectable implementation when such media hold or transmit device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components.

Implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled//implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

This detailed description sets forth various embodiments of devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In an embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to non-transitory machine-readable data storage media such as a recordable type medium such as a floppy disk, a hard disk drive, a Compact Disc (CD), a Digital Video Disk (DVD), a digital tape, a computer memory, etc. A signal bearing medium may also include transmission type medium such as a digital and/or an analog communication medium (e.g., a fiber optic cable, a waveguide, a wired communications link, a wireless communication link (e.g., transmitter, receiver, transmission logic, reception logic, etc.) and so forth).

Figure 19:
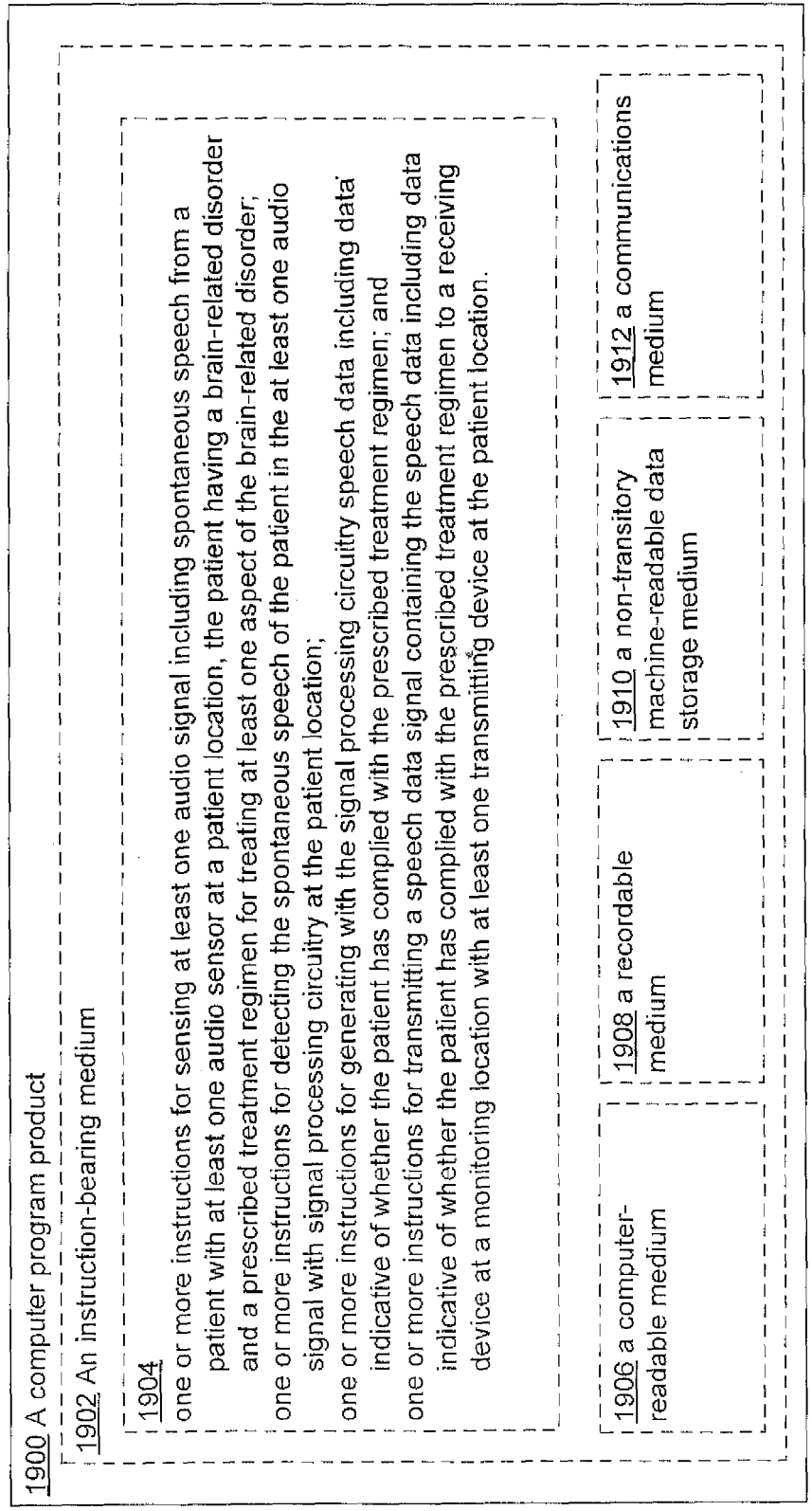
FIG. 19 is a block diagram of a computer program product including an instruction-bearing medium.

FIG. 19 is a block diagram of a computer program product 1900 for implementing a method as described in connection with FIG. 9. Computer program product 1900 includes an instruction-bearing medium 1902 bearing: one or more instructions for sensing at least one audio signal including spontaneous speech from a patient with at least one audio sensor at a patient location, the patient having a brain-related disorder and a prescribed treatment regimen for treating at least one aspect of the brain-related disorder; one or more instructions for detecting spontaneous speech of the patient in the at least one audio signal with signal processing circuitry at the patient location; one or more instructions for generating with the signal processing circuitry speech data including data indicative of whether the patient has complied with the prescribed treatment regimen; and one or more instructions for transmitting a speech data signal containing the speech data including data indicative of whether the patient has complied with the prescribed treatment regimen to a receiving device at a monitoring location with at least one transmitting device at the patient location, as indicated at 1904. Instruction-bearing medium 1902 may be, for example, a computer-readable medium 1906, a recordable medium 1908, a non-transitory machine-readable data storage medium 1910, or a communications medium 1912, examples of which are described herein above.

Figure 20:
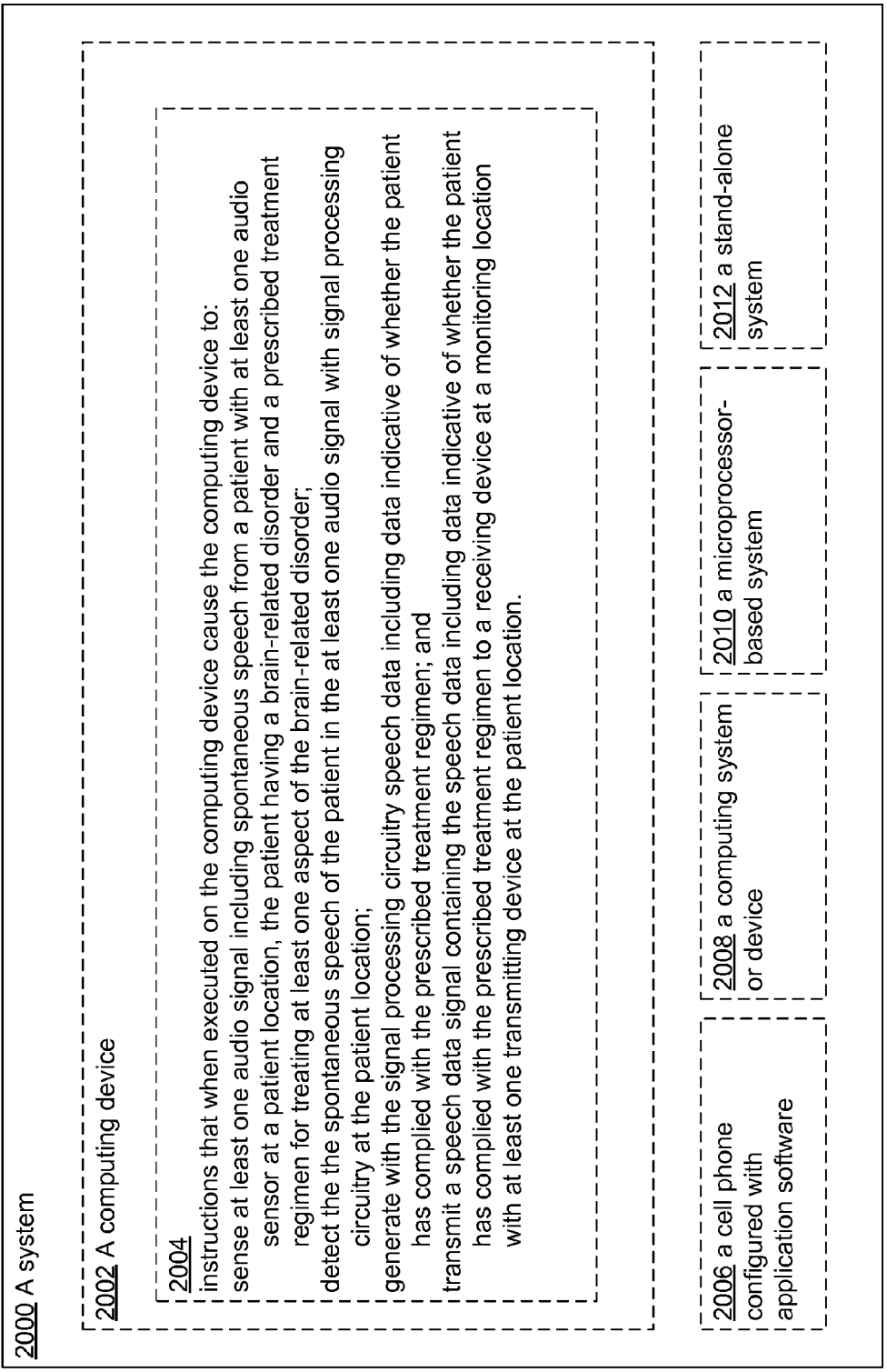
FIG. 20 is a block diagram of a system including a computing device.

FIG. 20 is a block diagram of a system 2000 for implementing a method as described in connection with FIG. 9. System 2000 includes a computing device 2002 and instructions that when executed on the computing device cause the computing device to sense at least one audio signal including spontaneous speech from a patient with at least one audio sensor at a patient location, the patient having a brain-related disorder and a prescribed treatment regimen for treating at least one aspect of the brain-related disorder; detect spontaneous speech of the patient in the at least one audio signal with signal processing circuitry at the patient location; generate with the signal processing circuitry speech data including data indicative of whether the patient has complied with the prescribed treatment regimen; and transmit a speech data signal containing the speech data including data indicative of whether the patient has complied with the prescribed treatment regimen to a receiving device at a monitoring location with at least one transmitting device at the patient location, as indicated at 2004. System 2000 may be, for example, a cell phone configured with application software 2006, a computing system or device 2008, a microprocessor-based system 2010, and/or a stand-alone system 2012.

Figure 21:
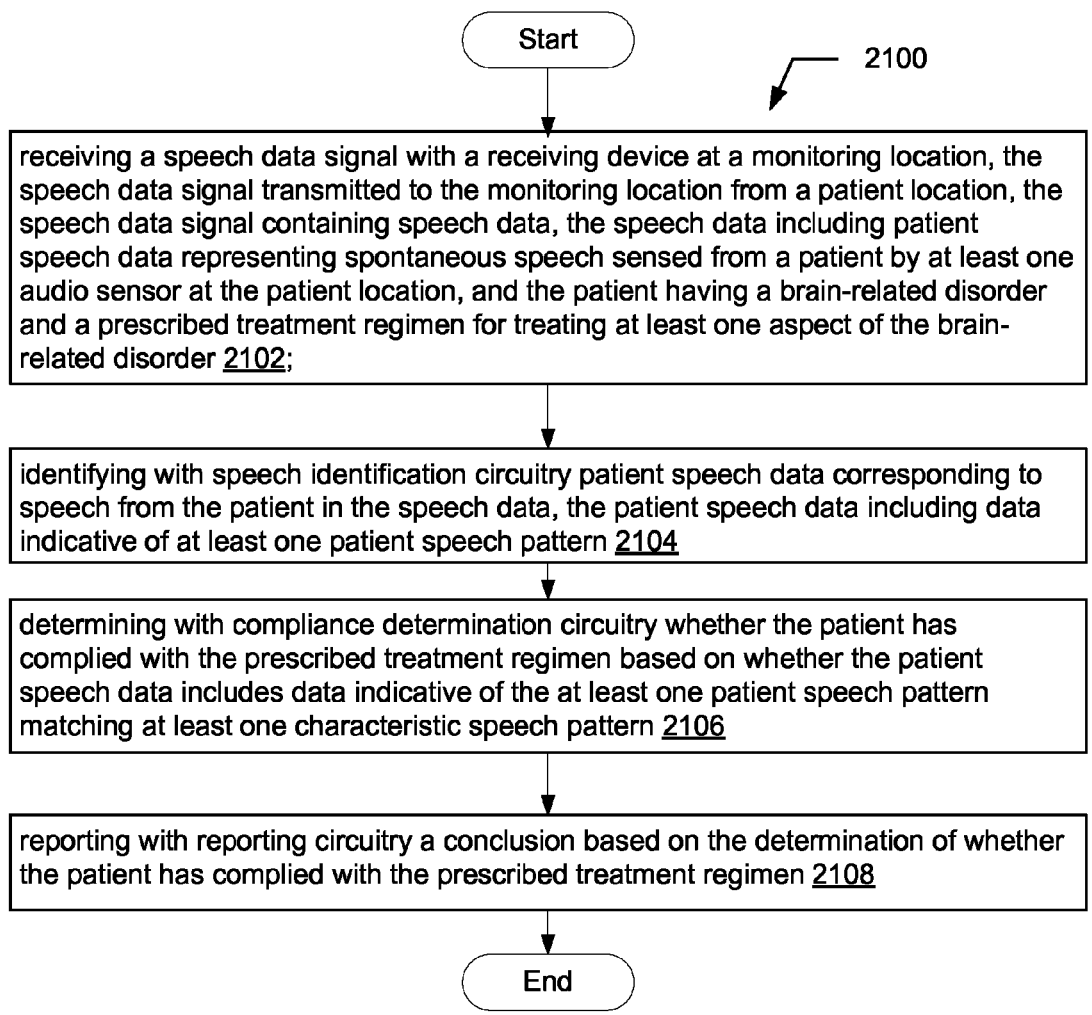
FIG. 21 is a flow diagram of a method of monitoring compliance of patient with a prescribed treatment regimen.

FIG. 21 is a flow diagram of a method 2100 of monitoring compliance of a patient with a prescribed treatment regimen, including method aspects occurring at or associated with a monitoring location, e.g., monitoring location 112 in FIG. 1. Method 2100 includes receiving a speech data signal with a receiving device at a monitoring location, the speech data signal transmitted to the monitoring location from a patient location, the speech data signal containing speech data, the speech data including patient speech data representing spontaneous speech sensed from a patient by at least one audio sensor at a patient location, and the patient having a brain-related disorder and a prescribed treatment regimen for treating at least one aspect of the brain-related disorder, as indicated at 2102; identifying with speech identification circuitry patient speech data corresponding to speech from the patient in the speech data, the patient speech data including data indicative of at least one patient speech pattern, as indicated at 2104; determining with compliance determination circuitry whether the patient has complied with the prescribed treatment regimen based on whether the patient speech data includes data indicative of the at least one patient speech pattern matching at least one characteristic speech pattern, as indicated at 2106; and reporting with reporting circuitry a conclusion based on the determination of whether the patient has complied with the prescribed treatment regimen, as indicated at 2108.

FIGS. 22-32 depict variations and expansions of method 2100 as shown in FIG. 21. In the methods depicted in FIGS. 22-32, steps 2102-2108 are as described generally in connection with FIG. 21. Here and elsewhere, method steps outlined with dashed lines represent steps that are included in some, but not all method aspects, and combinations of steps other than those specifically depicted in the figures are possible as would be known by those having ordinary skill in the relevant art.

Figure 22:
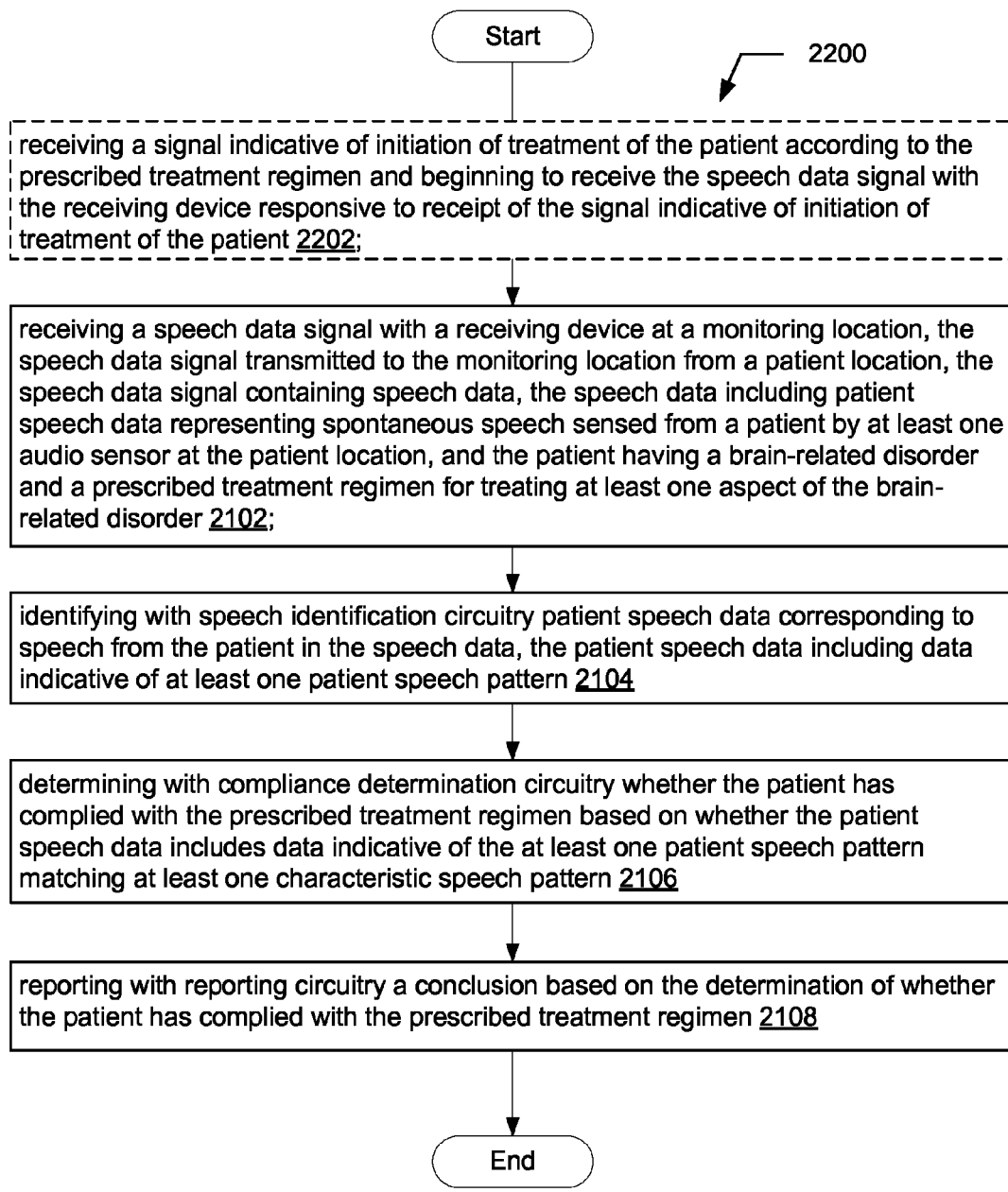
FIG. 22 is a flow diagram of further aspects of the method of FIG. 22.

As shown in FIG. 22, a method 2200 includes receiving a signal indicative of initiation of treatment of the patient according to the treatment regimen and beginning to receive the speech data signal with the receiving device responsive to receipt of the signal indicative of initiation of treatment of the patient, as indicated at 2202.

Figure 23:
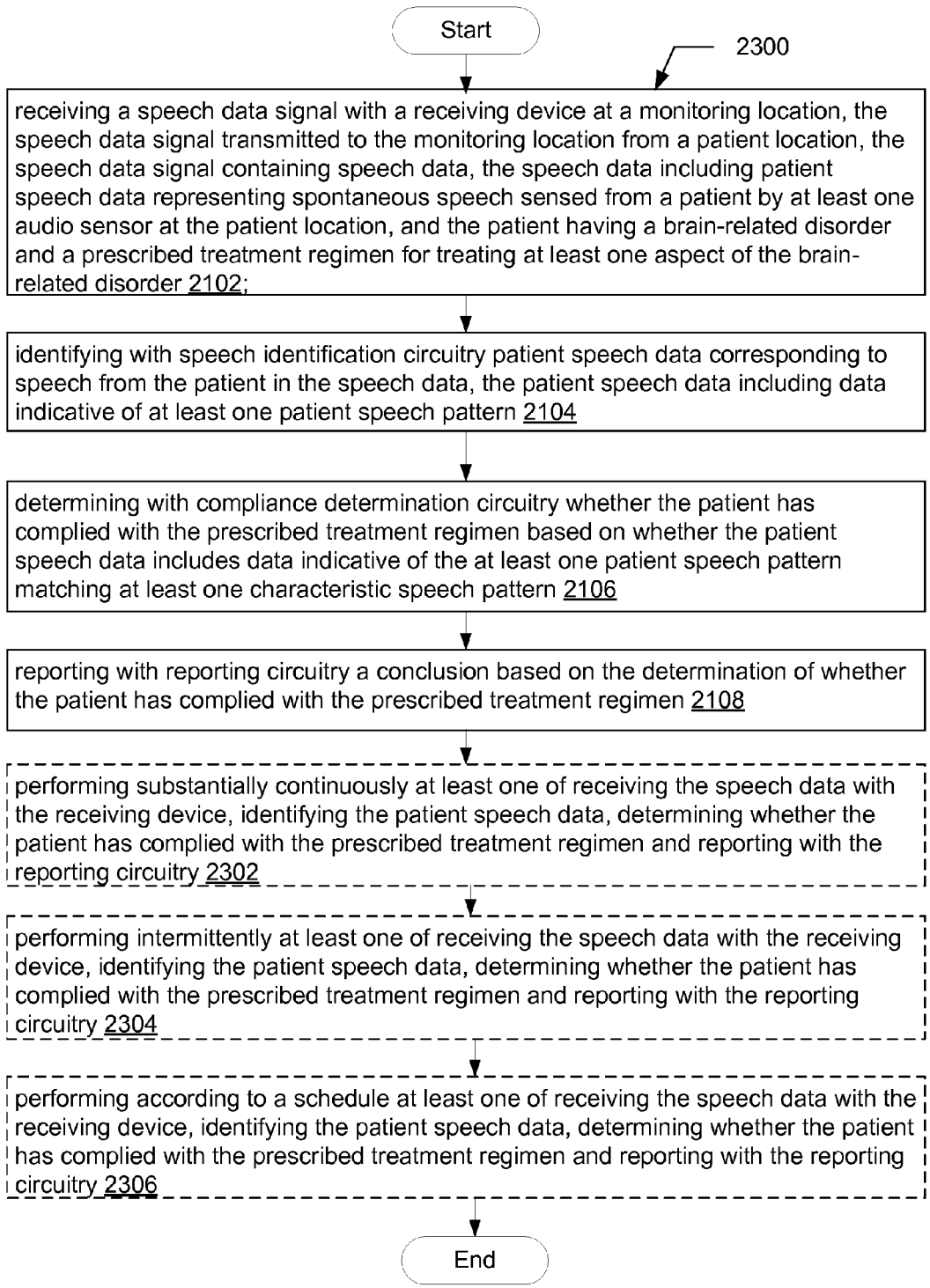
FIG. 23 is a flow diagram of further aspects of the method of FIG. 22.

As shown in FIG. 23, in an aspect, a method 2300 includes performing substantially continuously at least one of receiving the speech data with the receiving device, identifying the patient speech data, determining whether the patient has complied with the prescribed treatment regimen and reporting with the reporting circuitry, as indicated at 2302. In another aspect, method 2300 includes performing intermittently at least one of receiving the speech data with the receiving device, identifying the patient speech data, determining whether the patient has complied with the prescribed treatment regimen and reporting with the reporting circuitry, as indicated at 2304. In another aspect, method 2300 includes performing according to a schedule at least one of receiving the speech data with the receiving device, identifying the patient speech data, determining whether the patient has complied with the prescribed treatment regimen and reporting with the reporting circuitry, as indicated at 2306.

Figure 24:
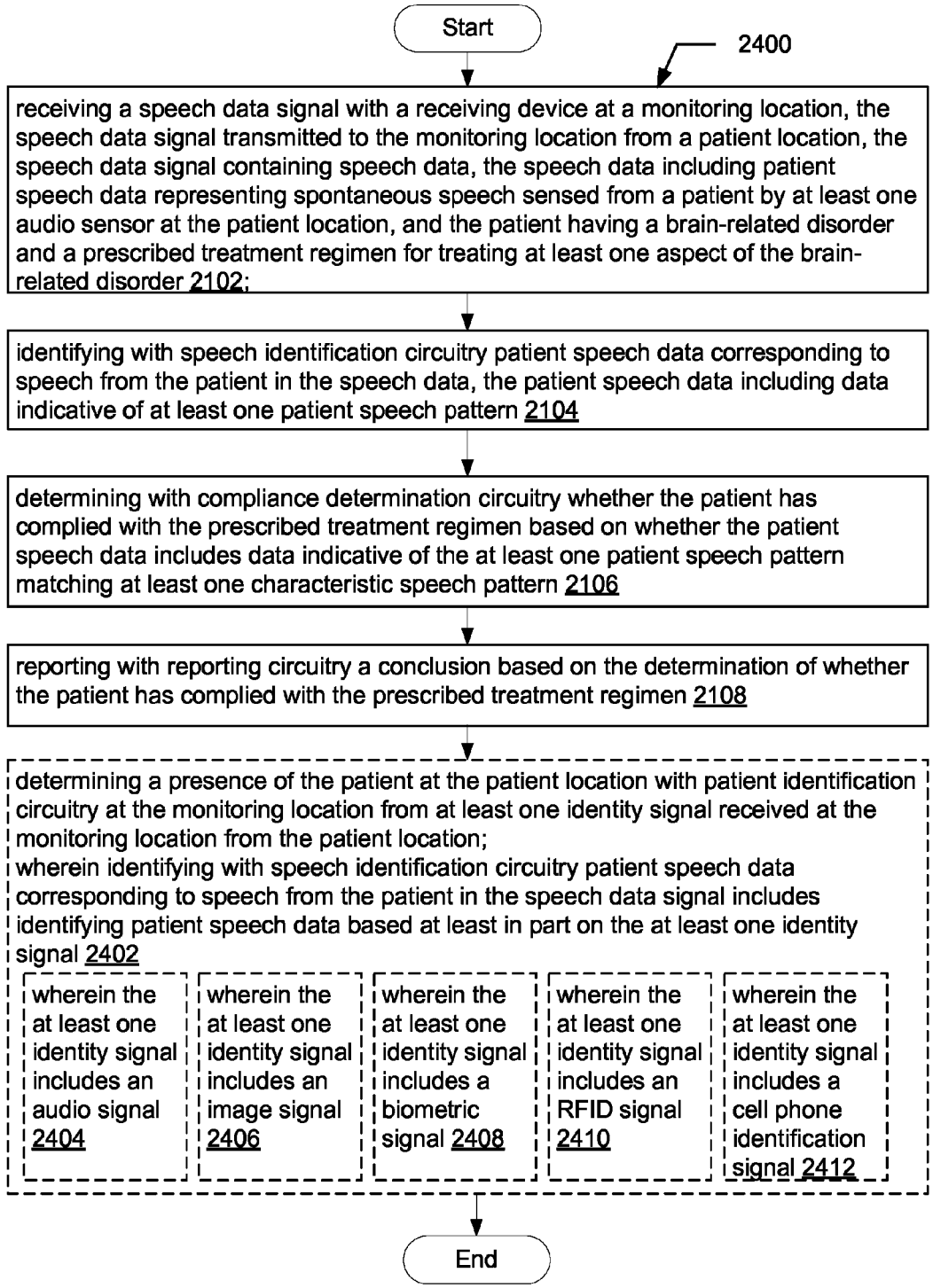
FIG. 24 is a flow diagram of further aspects of the method of FIG. 22.

FIG. 24 depicts a method 2400, which includes determining a presence of the patient at the patient location with patient identification circuitry at the monitoring location from at least one identity signal received at the monitoring location from the patient location, wherein identifying with speech identification circuitry patient speech data corresponding to speech from the patient in the speech data signal includes identifying patient speech data based at least in part on the identity signal, as indicated at 2402. In various aspects, the identity signal includes a voice signal, as indicated at 2404; an image signal, as indicated at 2406; a biometric signal, as indicated at 2408; an RFID signal, as indicated at 2410; or a cell phone identification signal, as indicated at 2412.

Figure 25:
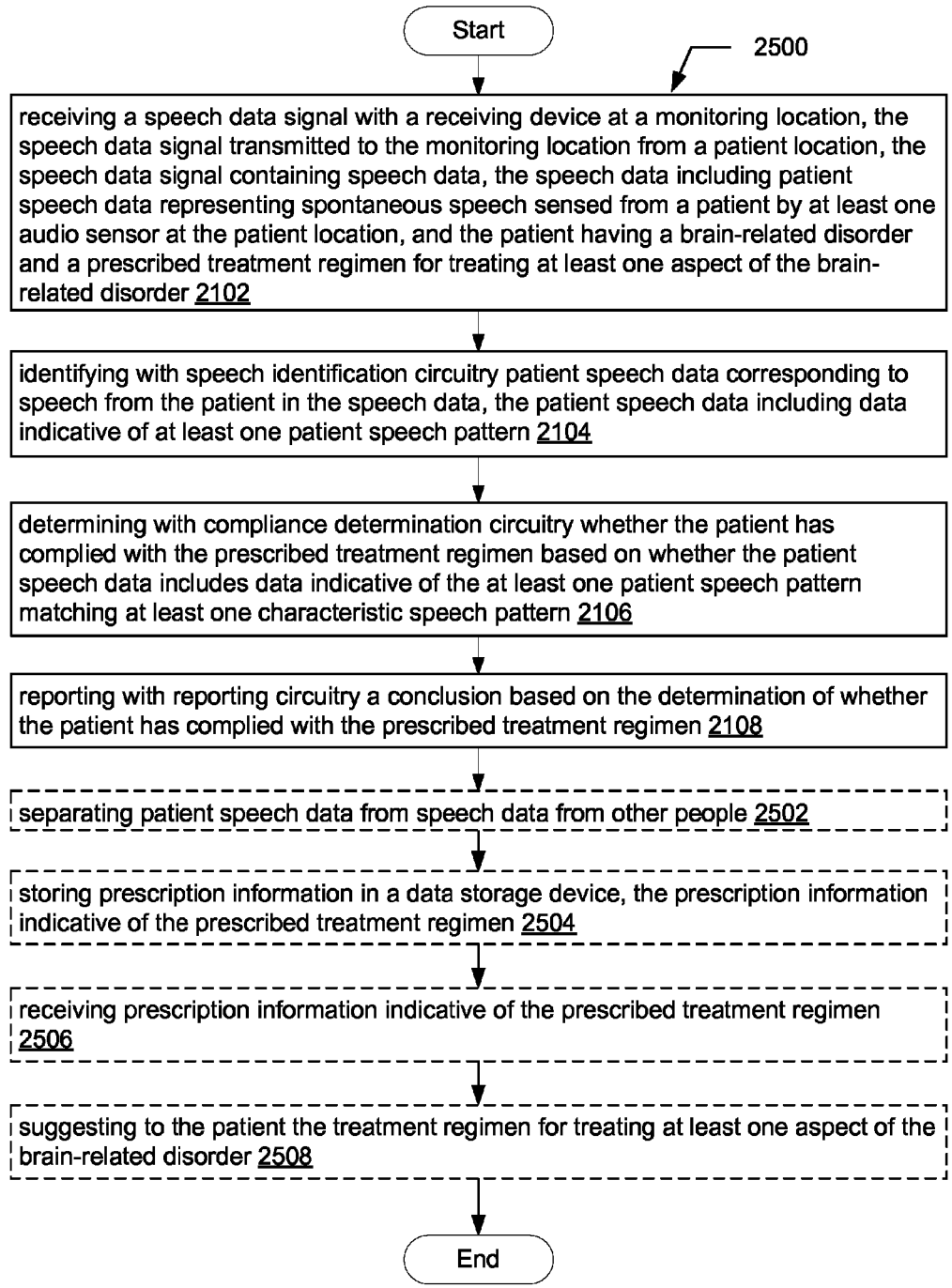
FIG. 25 is a flow diagram of further aspects of the method of FIG. 22.

FIG. 25 depicts method 2500, which includes one or more of separating patient speech data from speech data from other people, as indicated at 2502; storing prescription information in a data storage device, the prescription information indicative of the prescribed treatment regimen, as indicated at 2504; receiving prescription information indicative of the prescribed treatment regimen, as indicated at 2506; and suggesting to the patient the treatment regimen for treating at least one aspect of the brain-related disorder, as indicated at 2508.

Figure 26:
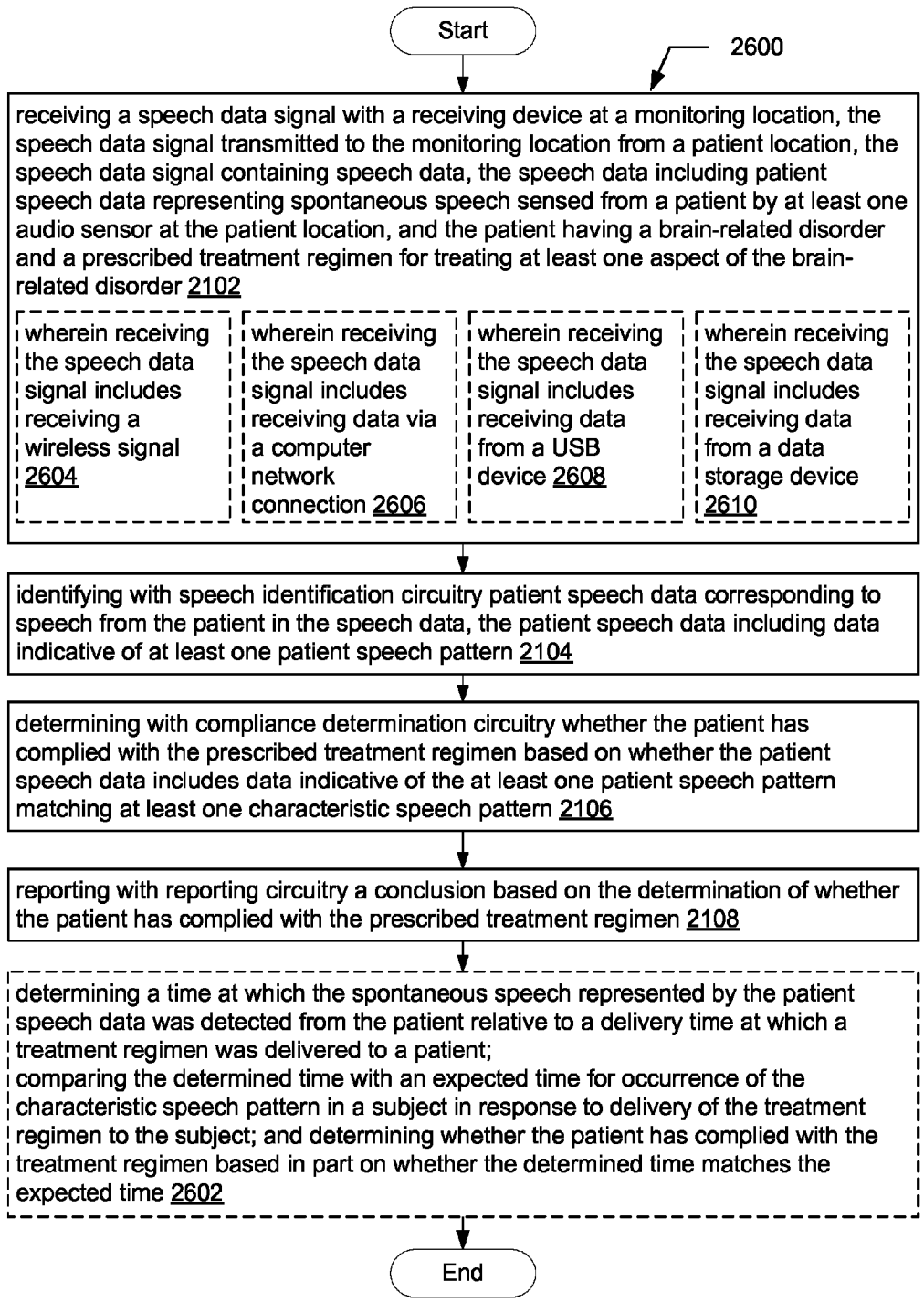
FIG. 26 is a flow diagram of further aspects of the method of FIG. 22.

FIG. 26 depicts a method 2600, relating to determining patient compliance based on whether the time course of the patient's response to a treatment regimen matches an expected time course. In an aspect, method 2600 includes determining a time at which the spontaneous speech represented by the patient speech data was detected from the patient relative to a delivery time at which a treatment regimen was delivered to a patient, comparing the determined time with an expected time for occurrence of the characteristic speech pattern in a subject in response to delivery of the treatment regimen to the subject, and determining whether the patient has complied with the prescribed treatment regimen based in part on whether the determined time matches the expected time, as indicated at 2602. In various aspects, receiving the speech data signal includes receiving a wireless signal, as indicated at 2604; receiving data via a computer network connection, as indicated at 2606; receiving data from a USB device, as indicated at 2608; and/or receiving data from a data storage device, as indicated at 2610.

Figure 27:
FIG. 27 is a flow diagram of further aspects of the method of FIG. 22.

FIG. 27 depicts method 2700 including steps 2102-2108 as shown in FIG. 21, and including additional steps relating to comparison of a patient's speech patterns with multiple characteristic speech patterns. In one aspect, at least one of identifying with speech identification circuitry patient speech data corresponding to speech from the patient in the speech data and determining with compliance determination circuitry whether the patient has complied with the prescribed treatment regimen includes analyzing the speech data with a speech processor, as indicated at 2702. In another aspect, at least one of identifying with speech identification circuitry patient speech data corresponding to speech from the patient in the speech data and determining with compliance determination circuitry whether the patient has complied with the prescribed treatment regimen includes analyzing the patient speech data to determine the patient speech pattern from the patient speech data, and comparing the patient speech pattern with the at least one characteristic speech pattern, as indicated at 2704.

In an aspect, comparing the patient speech pattern with the at least one characteristic speech pattern includes comparing the patient speech pattern with a plurality of characteristic speech patterns, as indicated at 2706. In addition, method 2700 may include determining which of the plurality of characteristic speech patterns best matches the patient speech pattern, as indicated at 2708. In connection therewith, an aspect, method 2700 also includes determining a level of compliance of the patient with the prescribed treatment regimen based on which of the plurality of characteristic speech patterns best matches the patient speech pattern, wherein the plurality of characteristic speech patterns includes a plurality of previous speech patterns of the patient each representative of a speech pattern of the patient at a different level of compliance of the patient with prescribed treatment regimen, and wherein the characteristic speech pattern that best matches the patient speech pattern indicates the level of compliance of the patient with the prescribed treatment regimen, as indicated at 2710. Method 2700 may also include determining a level of compliance of the patient with the prescribed treatment regimen based on which of the plurality of characteristic speech patterns best matches the patient speech pattern, wherein the plurality of characteristic speech patterns includes a plurality of population speech patterns, each population speech pattern representative of a typical speech pattern for a population of patients at a different level of compliance with the prescribed treatment regimen, and wherein the characteristic speech pattern that best matches the patient speech pattern indicates the level of compliance of the patient with the prescribed treatment regimen, as indicated at 2712.

Figure 28:
FIG. 28 is a flow diagram of further aspects of the method of FIG. 22.

FIG. 28 depicts method 2800 including steps 2102-2108 as shown in FIG. 21. In an aspect of method 2800, at least one of identifying with speech identification circuitry patient speech data in the speech data and determining with compliance determination circuitry whether the patient has complied with the prescribed treatment regimen includes comparing the patient speech data with characteristic speech data indicative of the characteristic speech pattern, as indicated at 2802. In an aspect, comparing the speech data with the characteristic speech data indicative of the characteristic speech pattern includes comparing the patient speech data with a plurality of characteristic speech data sets, each said characteristic speech data set indicative of a characteristic speech pattern, indicated at 2804. In connection therewith, in an aspect, method 2800 also includes determining which of the plurality of characteristic speech data sets best matches the patient speech data, as indicated at 2806. In an aspect, each said characteristic speech data set corresponds to a stored speech pattern representative of the patient undergoing a distinct treatment regimen, as indicated at 2808, or to a stored speech pattern representative of a population of patients undergoing a distinct treatment regimen, as indicated at 2810. In an aspect, method 2800 includes identifying a treatment regimen associated with the characteristic speech data set that best matches the patient speech data, as indicated at 2812.

Figure 29:
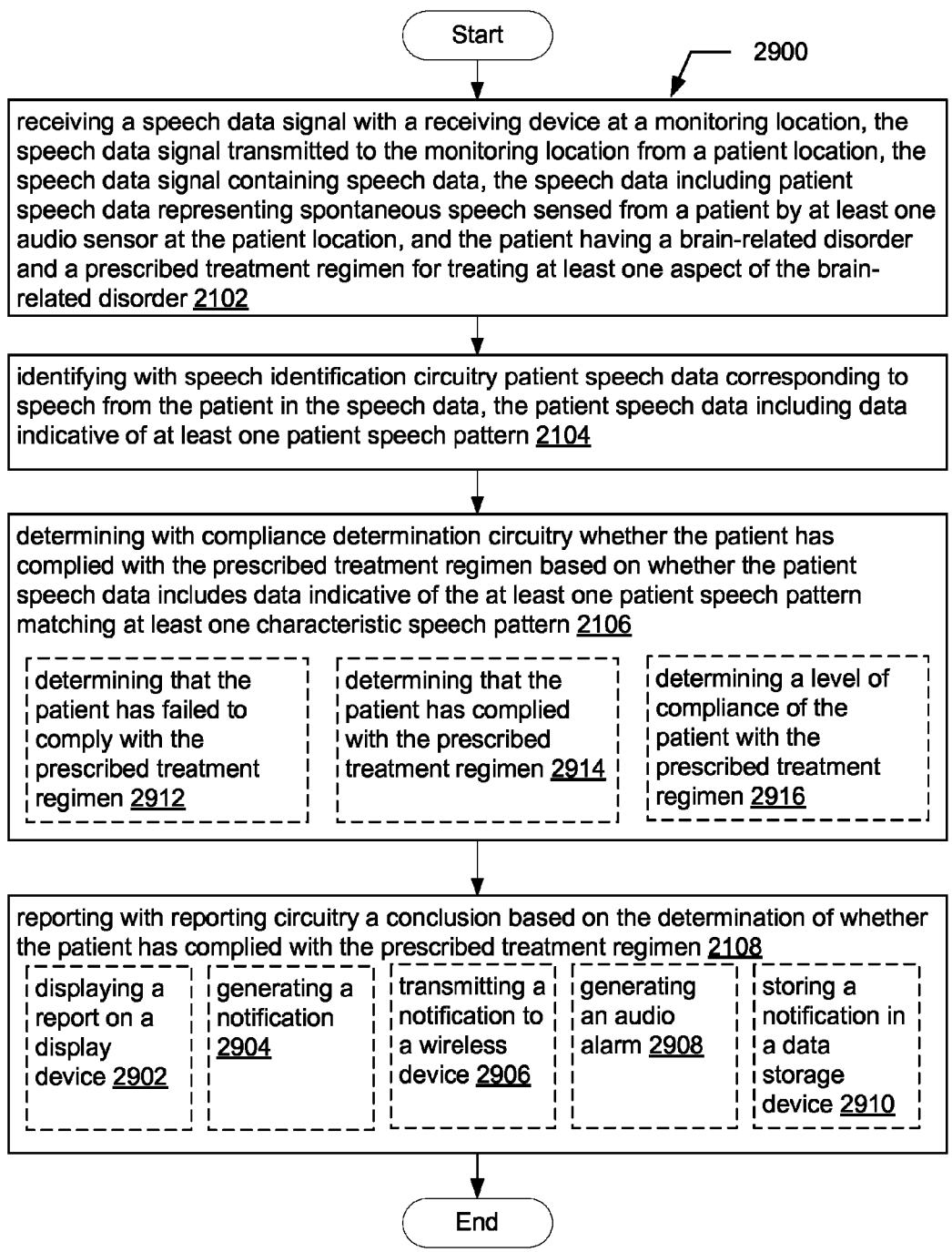
FIG. 29 is a flow diagram of further aspects of the method of FIG. 22.

FIG. 29 depicts method 2900, in which, in various aspects, reporting with reporting circuitry a conclusion based on the determination of whether the patient has complied with the prescribed treatment regimen includes displaying a report on a display device, as indicated at 2902; generating a notification, as indicated at 2904; transmitting a notification to a wireless device, as indicated at 2906; generating an audio alarm, as indicated at 2908; or storing a notification in a data storage device, as indicated at 2910. Generating an audio alarm may involve generating a beeping or chiming sound, for example, or generating a voice alarm (e.g., a warning or notification) from recorded or synthesized speech, e.g., to deliver a verbal warning to the medical care provider at the monitoring location.

In other aspects, determining with compliance determination circuitry whether the patient has complied with the prescribed treatment regimen includes determining that the patient has failed to comply with the prescribed treatment regimen, as indicated at 2912; determining that the patient has complied with the prescribed treatment regimen, as indicated at 2914; and/or determining a level of compliance of the patient with the prescribed treatment regimen, as indicated at 2916. Approaches for determining compliance, lack of compliance, or level of compliance are discussed herein above.

Figure 30:
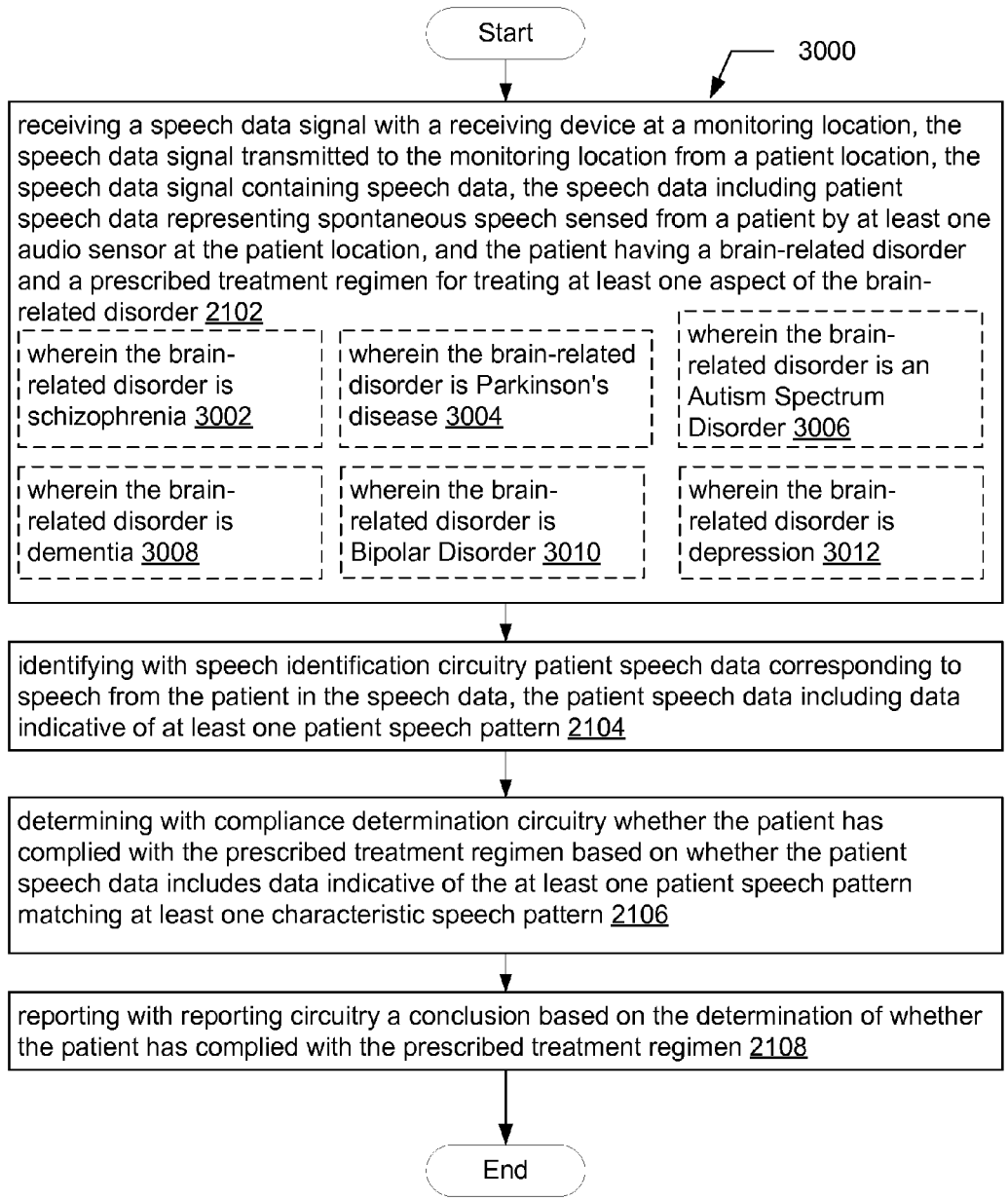
FIG. 30 is a flow diagram of further aspects of the method of FIG. 22.

FIG. 30 depicts method 3000, wherein the brain-related disorder is schizophrenia, as indicated at 3002; Parkinson's disease, as indicated at 3004; an Autism Spectrum Disorder, as indicated at 3006; dementia, as indicated at 3008; Bipolar Disorder, as indicated at 3010; or depression, as indicated at 3012. Other brain-related disorders, as discussed herein, may be monitored.

Figure 31:
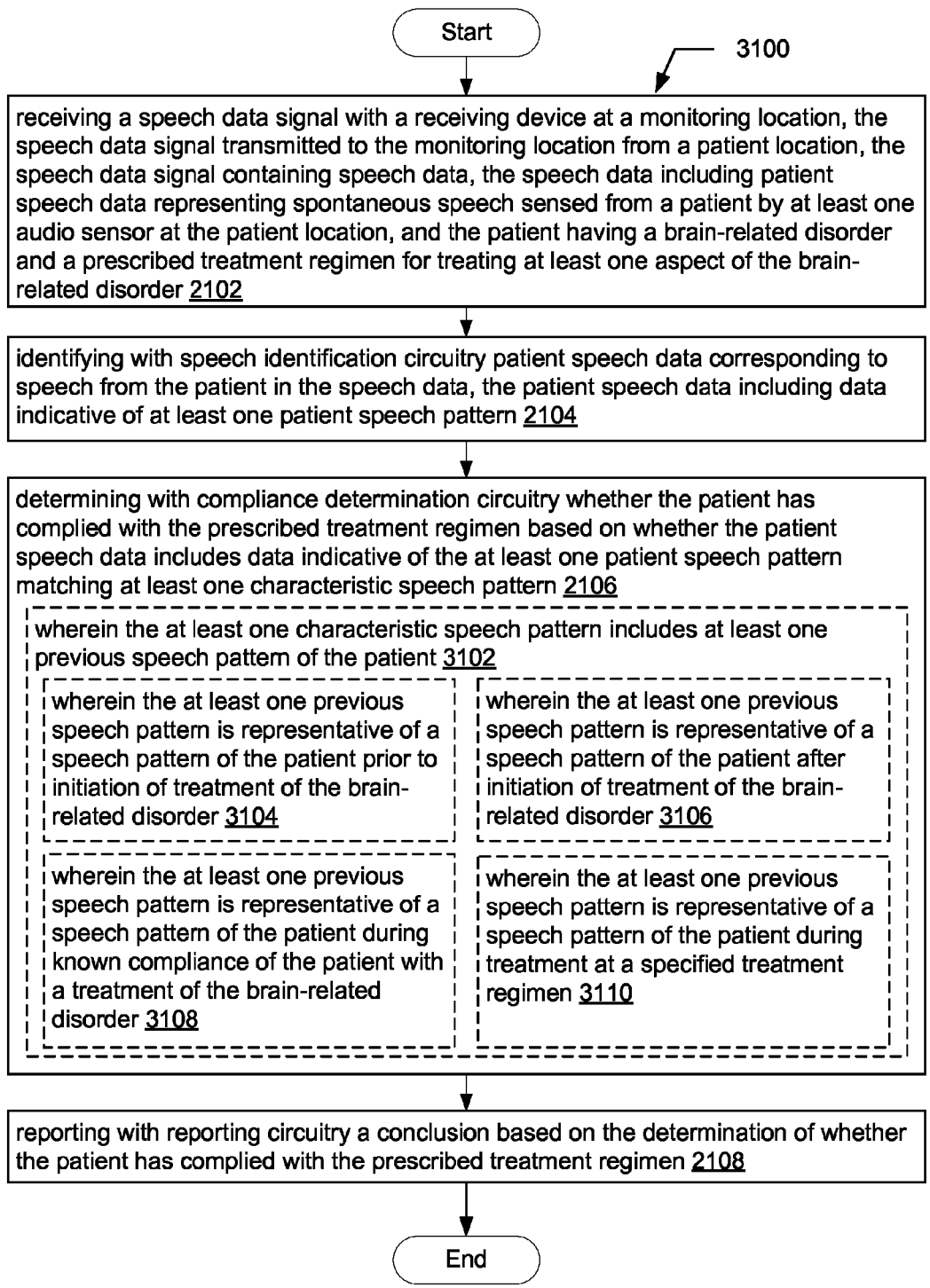
FIG. 31 is a flow diagram of further aspects of the method of FIG. 22.

As shown in FIG. 31, in an aspect of method 3100, the at least one characteristic speech pattern includes at least one previous speech pattern of the patient, as indicated at 3102. For example, in various aspects, the at least one previous speech pattern is representative of a speech pattern of the patient prior to initiation of treatment of the brain-related disorder, as indicated at 3104; a speech pattern of the patient after initiation of treatment of the brain-related disorder, as indicated at 3106; a speech pattern of the patient during known compliance of the patient with a treatment of the brain-related disorder, as indicated at 3108; or a speech pattern of the patient during treatment at a specified treatment regimen, as indicated at 3110. Comparison of a patient speech pattern to one or more characteristic speech patterns is discussed herein above.

As shown in FIG. 32, in an aspect of a method 3200, the at least one characteristic speech pattern includes at least one population speech pattern representative of a typical speech pattern of a population of patients, as indicated at 3202. For example, the at least one population speech pattern is representative of speech patterns of a population without the brain-related disorder, as indicated at 3204; speech patterns of an untreated population with the brain-related disorder, as indicated at 3206; or speech patterns of a population having the brain-related disorder stabilized by a treatment regimen, as indicated at 3208.

FIG. 33 depicts a computer program product 3300, for implementing the method of FIG. 22. Computer program product 3300 includes an instruction-bearing medium 3302 bearing one or more instructions for receiving a speech data signal with a receiving device at a monitoring location, the speech data signal transmitted to the monitoring location from a patient location, the speech data signal containing speech data, the speech data including patient speech data representing spontaneous speech sensed from a patient by at least one audio sensor at a patient location, and the patient having a brain-related disorder and a prescribed treatment regimen for treating at least one aspect of the brain-related disorder, one or more instructions identifying with speech identification circuitry patient speech data corresponding to speech from the patient in the speech data, the patient speech data including data indicative of at least one patient speech pattern, one or more instructions for determining with compliance determination circuitry whether the patient has complied with the prescribed treatment regimen based on whether the patient speech data includes data indicative of the at least one patient speech pattern matching at least one characteristic speech pattern, and one or more instructions for reporting with reporting circuitry a conclusion based on the determination of whether the patient has complied with the prescribed treatment regimen, as indicated at 3304. Instruction-bearing medium 3302 may be, for example, a computer-readable medium 3306, a recordable medium 3308, a non-transitory machine-readable data storage medium 3310, or a communications medium 3312.

Figure 34:
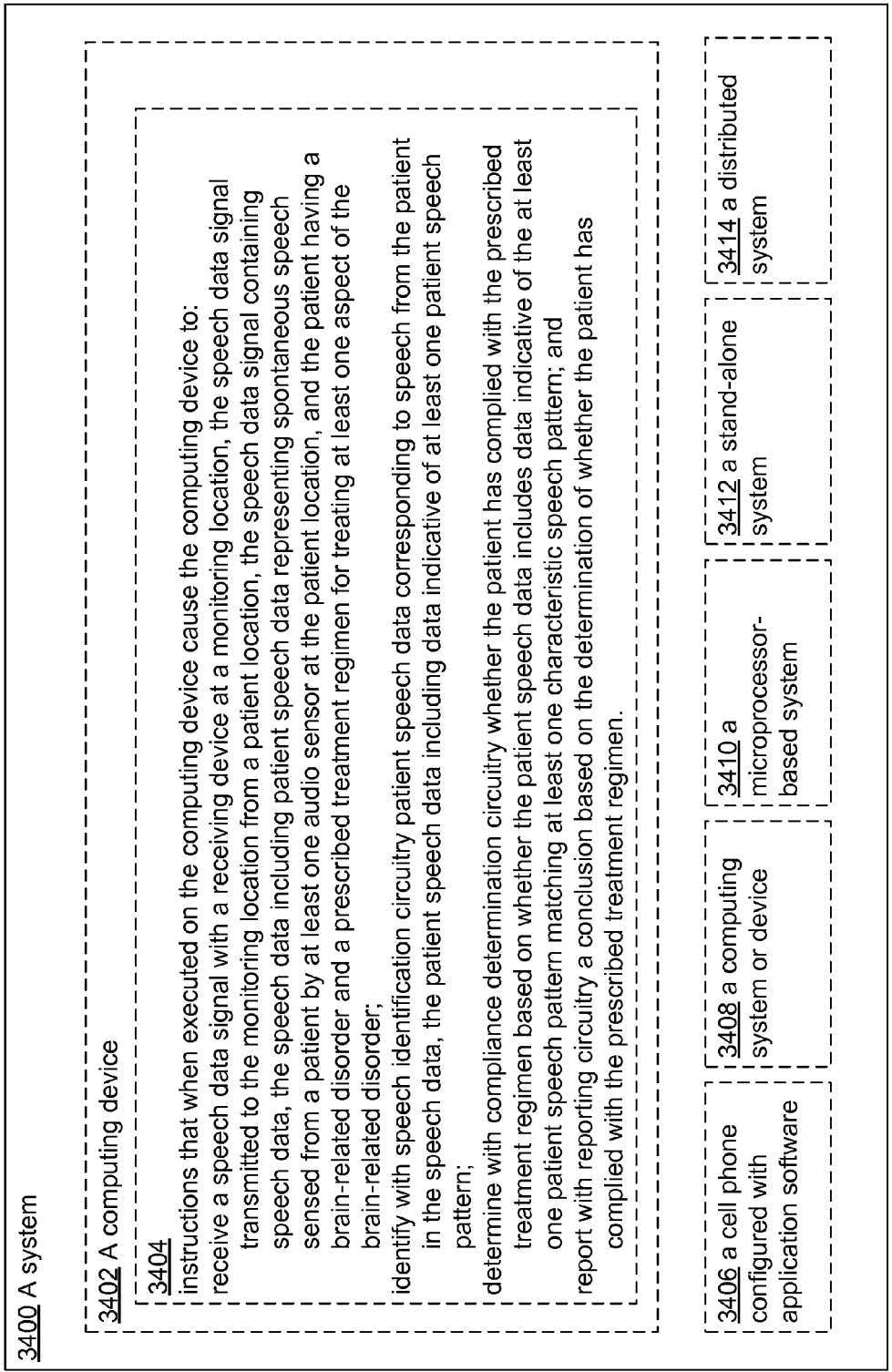
FIG. 34 is a block diagram of a system including a computing device.

FIG. 34 depicts a system 3400 for implementing the method of FIG. 22. System 3400 includes a computing device 3402 and instructions that when executed on computing device 3402 cause computing device 3402 to receive a speech data signal with a receiving device at a monitoring location, the speech data signal transmitted to the monitoring location from a patient location, the speech data signal containing speech data, the speech data including patient speech data representing spontaneous speech sensed from a patient by at least one audio sensor at a patient location, and the patient having a brain-related disorder and a prescribed treatment regimen for treating at least one aspect of the brain-related disorder; identify with speech identification circuitry patient speech data corresponding to speech from the patient in the speech data, the patient speech data including data indicative of at least one patient speech pattern; determine with compliance determination circuitry whether the patient has complied with the prescribed treatment regimen based on whether the patient speech data includes data indicative of the at least one patient speech pattern matching at least one characteristic speech pattern; and report with reporting circuitry a conclusion based on the determination of whether the patient has complied with the prescribed treatment regimen, as indicated at 3404. System 3400 may be, for example, a cell phone configured with application software, as indicated at 3406; a computing system or device 3408; a microprocessor-based system 3410; a stand-alone system 3412; or a distributed system 3414.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configured by," "configurable to," "operable/operative to," "adapted/adaptable," "able to," "conformable/conformed to," etc. Those skilled in the art will recognize that such terms (e.g., "configured to") generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system comprising:
   at least one receiving device for use at a monitoring location for receiving a speech data signal transmitted to the monitoring location from a patient location, the speech data signal containing speech data, the speech data including patient speech data representing spontaneous speech sensed from a patient with at least one audio sensor at the patient location, and the patient having a brain-related disorder and a prescribed treatment regimen for treating at least one aspect of the brain-related disorder;
   speech identification circuitry configured to identify the patient speech data corresponding to speech from the patient in the speech data, the patient speech data including data indicative of at least one patient speech pattern;
   compliance determination circuitry configured to determine compliance of the patient with the prescribed treatment regimen based on whether the patient speech data includes data indicative of the at least one patient speech pattern matching at least one characteristic speech pattern; and
   reporting circuitry configured to report a conclusion based on the determination of whether the patient has complied with the prescribed treatment regimen.

2. The system of claim 1, further comprising control circuitry for controlling at least one of the at least one receiving device, the speech identification circuitry, the compliance determination circuitry, and the reporting circuitry.

3. The system of claim 1, wherein the speech identification circuitry includes:
   patient identification circuitry configured to determine a presence of the patient from at least one identity signal received at the monitoring location from the patient location;
   wherein the speech identification circuitry is configured to identify patient speech data corresponding to speech from the patient in the speech data based at least in part on the determination of the presence of the patient by the patient identification circuitry.

4. The system of claim 3, wherein the identity signal includes at least a portion of the speech data signal, wherein the patient identification circuitry is configured to analyze the speech data signal to determine the presence of the patient by identifying at least a portion of the speech data signal that resembles a known speech data signal of the patient, and wherein the speech identification circuitry is configured to identify patient speech data by identifying speech data corresponding to the presence of the patient.

5. The system of claim 3, wherein the identity signal includes an image signal received from an imaging device at the patient location, wherein the patient identification circuitry is configured to analyze the image signal to determine the presence of the patient, and wherein the speech identification circuitry is configured to identify patient speech data by identifying speech data corresponding to the presence of the patient detected from the image signal.

6. The system of claim 5, wherein the patient identification circuitry is configured to analyze the image signal to determine the presence of the patient through at least one of facial recognition and gait analysis.

7. The system of claim 3, wherein the identity signal includes a biometric signal from at least one biometric sensor at the patient location, wherein the patient identification circuitry is configured to analyze the biometric signal to determine the presence of the patient, and wherein the speech identification circuitry is configured to identify patient speech data by identifying speech data corresponding to the presence of the patient detected from the biometric signal.

8. The system of claim 3, wherein the identity signal includes at least one of an authentication factor, a cell phone identification code, and an RFID.

9. The system of claim 1, wherein at least one of the speech identification circuitry and the compliance determination circuitry includes a speech processor.

10. The system of claim 1, wherein the compliance determination circuitry includes:
    a speech processor for analyzing the patient speech data to determine the at least one patient speech pattern; and
    a comparator for comparing the at least one patient speech pattern with the at least one characteristic speech pattern.

11. The system of claim 1, wherein the compliance determination circuitry includes:
    a comparator for comparing the patient speech data with a characteristic speech data set indicative of the characteristic speech pattern.

12. The system of claim 1, further comprising at least one of an input device for receiving prescription information indicative of the treatment regimen prescribed to the patient and at least one data storage device for storing prescription information indicative of the treatment regimen prescribed to the patient.

13. The system of claim 1, wherein the at least one receiving device includes at least one of a wireless receiver, a computer network connection, a USB port, and a computer drive.

14. The system of claim 1, wherein the reporting circuitry includes at least one of a display device, circuitry for generating a notification, circuitry for transmitting a notification to a wireless device, circuitry for generating an audio alarm, and circuitry for storing a notification in a data storage device.

15. A method of monitoring compliance of a patient with a treatment regimen, comprising:
    receiving a speech data signal with a receiving device at a monitoring location, the speech data signal transmitted to the monitoring location from a patient location, the speech data signal containing speech data, the speech data including patient speech data representing spontaneous speech sensed from a patient by at least one audio sensor at the patient location, and the patient having a brain-related disorder and a prescribed treatment regimen for treating at least one aspect of the brain-related disorder;
    identifying with speech identification circuitry patient speech data corresponding to speech from the patient in the speech data, the patient speech data including data indicative of at least one patient speech pattern;
    determining with compliance determination circuitry whether the patient has complied with the prescribed treatment regimen based on whether the patient speech data includes data indicative of the at least one patient speech pattern matching at least one characteristic speech pattern; and reporting with reporting circuitry a conclusion based on the determination of whether the patient has complied with the prescribed treatment regimen.

16. The method of claim 15, further comprising:
receiving a signal indicative of initiation of treatment of the patient according to the prescribed treatment regimen and beginning to receive the speech data signal with the receiving device responsive to receipt of the signal indicative of initiation of treatment of the patient.

17. The method of claim 15, further comprising:
determining a presence of the patient at the patient location, with patient identification circuitry at the monitoring location, from at least one identity signal received at the monitoring location from the patient location;
wherein identifying with speech identification circuitry patient speech data corresponding to speech from the patient in the speech data signal includes identifying patient speech data based at least in part on the identity signal.

18. The method of claim 17, wherein the identity signal includes at least one of a voice signal, an image signal, a biometric signal, an RFID signal, and a cell phone identification signal.

19. The method of claim 15, further comprising:
determining a time at which the spontaneous speech represented by the patient speech data was detected from the patient relative to a delivery time at which a treatment regimen was delivered to a patient;
comparing the determined time with an expected time for occurrence of the characteristic speech pattern in a subject in response to delivery of the treatment regimen to the subject; and determining whether the patient has complied with the prescribed treatment regimen based in part on whether the determined time matches the expected time.

20. The method of claim 15, wherein at least one of identifying with speech identification circuitry patient speech data corresponding to speech from the patient in the speech data and determining with compliance determination circuitry whether the patient has complied with the prescribed treatment regimen includes:
analyzing the patient speech data to determine the patient speech pattern from the patient speech data; and
comparing the patient speech pattern with the at least one characteristic speech pattern.

21. The method of claim 20, wherein comparing the patient speech pattern with the at least one characteristic speech pattern includes comparing the patient speech pattern with a plurality of characteristic speech patterns; and determining which of the plurality of characteristic speech patterns best matches the patient speech pattern.

22. The method of claim 21, further comprising:
determining a level of compliance of the patient with the prescribed treatment regimen based on which of the plurality of characteristic speech patterns best matches the patient speech pattern;
wherein the characteristic speech pattern that best matches the patient speech pattern indicates the level of compliance of the patient with the prescribed treatment regimen; and
wherein the plurality of characteristic speech patterns includes at least one of a plurality of previous speech patterns of the patient each representative of a speech pattern of the patient at a different level of compliance of the patient with the prescribed treatment regimen, and a plurality of population speech patterns, each population speech pattern representative of a typical speech pattern for a population of patients at a different level of compliance with the prescribed treatment regimen.

23. The method of claim 15, wherein at least one of identifying with speech identification circuitry patient speech data in the speech data and determining with compliance determination circuitry whether the patient has complied with the prescribed treatment regimen includes:
comparing the patient speech data with characteristic speech data indicative of the characteristic speech pattern.

24. The method of claim 23, wherein comparing the speech data with the characteristic speech data indicative of the characteristic speech pattern includes comparing the patient speech data with a plurality of characteristic speech data sets, each said characteristic speech data set indicative of a characteristic speech pattern.

25. The method of claim 24, further comprising at least one of determining which of the plurality of characteristic speech data sets best matches the patient speech data, and identifying a treatment regimen associated with the characteristic speech data set that best matches the patient speech data.

26. The method of claim 24, wherein each said characteristic speech data set corresponds to at least one of a stored speech pattern representative of the patient undergoing a distinct treatment regimen and a stored speech pattern representative of a population of patients undergoing a distinct treatment regimen.

27. The method of claim 15, wherein the at least one characteristic speech pattern includes at least one previous speech pattern of the patient.

28. The method of claim 27, wherein the at least one previous speech pattern is representative of at least one of a speech pattern of the patient prior to initiation of treatment of the brain-related disorder, a speech pattern of the patient after initiation of treatment of the brain-related disorder, a speech pattern of the patient during known compliance of the patient with a treatment of the brain-related disorder, and a speech pattern of the patient during treatment at a specified treatment regimen.

29. The method of claim 15, wherein the at least one characteristic speech pattern includes at least one population speech pattern representative of a typical speech pattern of a population of patients.

30. The method of claim 29, wherein the at least one population speech pattern is representative of at least one of speech patterns of a population without the brain-related disorder, speech patterns of an untreated population with the brain-related disorder, and speech patterns of a population having the brain-related disorder stabilized by a treatment regimen.

31. The method of claim 15, further comprising:
performing, substantially continuously, intermittently, or according to a schedule, at least one of receiving the speech data with the receiving device, identifying the patient speech data, determining whether the patient has complied with the prescribed treatment regimen and reporting with the reporting circuitry.

32. The method of claim 15, further comprising at least one of separating patient speech data from speech data from other people, storing prescription information in a data storage device, the prescription information indicative of the prescribed treatment regimen, receiving prescription information indicative of the prescribed treatment regimen, and suggesting to the patient the treatment regimen for treating at least one aspect of the brain-related disorder.

33. The method of claim 15, wherein receiving the speech data signal includes at least one of receiving a wireless signal, receiving data via a computer network connection, receiving data from a USB device, and receiving data from a data storage device.

34. The method of claim 15, wherein reporting a conclusion based on the determination of whether the patient has complied with the prescribed treatment regimen includes at least one of displaying a report on a display device, generating a notification, transmitting a notification to a wireless device, generating an audio alarm, and storing a notification in a data storage device.

35. The method of claim 15, wherein determining with compliance determination circuitry whether the patient has complied with the prescribed treatment regimen includes at least one of determining that the patient has failed to comply with the prescribed treatment regimen, determining that the patient has complied with the prescribed treatment regimen, and determining a level of compliance of the patient with the prescribed treatment regimen.

36. The method of claim 15, wherein the brain-related disorder includes at least one of schizophrenia, Parkinson's disease, an Autism Spectrum Disorder, dementia, Bipolar Disorder, and depression.

37. A computer program product comprising:
a non-transitory machine-readable data storage medium bearing:
one or more instructions for receiving a speech data signal with a receiving device at a monitoring location, the speech data signal transmitted to the monitoring location from a patient location, the speech data signal containing speech data, the speech data including patient speech data representing spontaneous speech sensed from a patient by at least one audio sensor at a patient location, and the patient having a brain-related disorder and a prescribed treatment regimen for treating at least one aspect of the brain-related disorder;
one or more instructions for identifying with speech identification circuitry patient speech data corresponding to speech from the patient in the speech data, the patient speech data including data indicative of at least one patient speech pattern;
one or more instructions for determining with compliance determination circuitry whether the patient has complied with the prescribed treatment regimen based on whether the patient speech data includes data indicative of the at least one patient speech pattern matching at least one characteristic speech pattern; and
one or more instructions for reporting with reporting circuitry a conclusion based on the determination of whether the patient has complied with the prescribed treatment regimen.

38. The computer program product of claim 37, wherein the non-transitory machine-readable data storage medium bears
one or more instructions for receiving a signal indicative of initiation of treatment of the patient according to the prescribed treatment regimen and beginning to receive the speech data signal with the receiving device responsive to receipt of the signal indicative of initiation of treatment of the patient.

39. The computer program product of claim 37, wherein the non-transitory machine-readable data storage medium bears
one or more instructions for performing substantially continuously, intermittently, or according to a schedule at least one of receiving the speech data with the receiving device, identifying the patient speech data, determining whether the patient has complied with the prescribed treatment regimen and reporting with the reporting circuitry.

40. The computer program product of claim 37, wherein the non-transitory machine-readable data storage medium bears one or more instructions for determining a presence of the patient at the patient location, with patient identification circuitry at the monitoring location, from at least one identity signal received at the monitoring location from the patient location;
wherein identifying with speech identification circuitry patient speech data corresponding to speech from the patient in the speech data signal includes identifying patient speech data based at least in part on the identity signal.

41. The computer program product of claim 40, wherein the identity signal includes at least one of a voice signal, an image signal, a biometric signal, an RFID signal, or a cell phone identification signal.

42. The computer program product of claim 37, wherein the non-transitory machine-readable data storage medium bears
one or more instructions for separating patient speech data from speech data from other people.

43. The computer program product of claim 37, wherein the non-transitory machine-readable data storage medium bears
one or more instructions for suggesting to the patient the prescribed treatment regimen for treating at least one aspect of the brain-related disorder.

44. The computer program product of claim 37, wherein the non-transitory machine-readable data storage medium bears
one or more instructions for determining a time at which the spontaneous speech represented by the patient speech data was detected from the patient relative to a delivery time at which a treatment regimen was delivered to the patient;
comparing the determined time with an expected time for occurrence of the characteristic speech pattern in a subject in response to delivery of the treatment regimen to the subject; and determining whether the patient has complied with the prescribed treatment regimen based in part on whether the determined time matches the expected time.

45. The computer program product of claim 37, wherein at least one of the one or more instructions for identifying with speech identification circuitry patient speech data corresponding to speech from the patient in the speech data and the one or more instructions for determining with compliance determination circuitry whether the patient has complied with the prescribed treatment regimen include:
one or more instructions for analyzing the patient speech data to determine the patient speech pattern from the patient speech data; and
one or more instructions for comparing the patient speech pattern with the at least one characteristic speech pattern.

46. The computer program product of claim 45, wherein the one or more instructions for comparing the patient speech pattern with the at least one characteristic speech pattern include one or more instructions for comparing the patient speech pattern with a plurality of characteristic speech patterns.

47. The computer program product of claim 46, wherein the non-transitory machine-readable data storage medium bears one or more instructions for determining which of the plurality of characteristic speech patterns best matches the patient speech pattern.

48. The computer program product of claim 47, wherein the non-transitory machine-readable data storage medium bears one or more instructions for determining a level of compliance of the patient with the prescribed treatment regimen based on which of the plurality characteristic speech patterns best matches the patient speech pattern; wherein the plurality of characteristic speech patterns includes a plurality of previous speech patterns of the patient each representative of a speech pattern of the patient at a different level of compliance of the patient with the prescribed treatment regimen, and wherein the characteristic speech pattern that best matches the patient speech pattern indicates the level of compliance of the patient with the prescribed treatment regimen.

49. The computer program product of claim 47, wherein the non-transitory machine-readable data storage medium bears one or more instructions for determining a level of compliance of the patient with the prescribed treatment regimen based on which of the plurality of characteristic speech patterns best matches the patient speech pattern; wherein the plurality of characteristic speech patterns includes a plurality of population speech patterns, each population speech pattern representative of a typical speech pattern for a population of patients at a different level of compliance with the prescribed treatment regimen, and wherein the characteristic speech pattern that best matches the patient speech pattern indicates the level of compliance of the patient with the prescribed treatment regimen.

50. The computer program product of claim 37, wherein the one or more instructions for reporting a conclusion based on the determination of whether the patient has complied with the prescribed treatment regimen include one or more instructions for displaying a report on a display device, generating a notification, transmitting a notification to a wireless device, generating an audio alarm, or storing a notification in a data storage device.

51. A system comprising:
  a computing device; and
  instructions that when executed on the computing device cause the computing device to:
    receive a speech data signal with a receiving device at a monitoring location, the speech data signal transmitted to the monitoring location from a patient location, the speech data signal containing speech data, the speech data including patient speech data representing spontaneous speech sensed from a patient by at least one audio sensor at a patient location, and the patient having a brain-related disorder and a prescribed treatment regimen for treating at least one aspect of the brain-related disorder;
    identify with speech identification circuitry patient speech data corresponding to speech from the patient in the speech data, the patient speech data including data indicative of at least one patient speech pattern;
    determine with compliance determination circuitry whether the patient has complied with the prescribed treatment regimen based on whether the patient speech data includes data indicative of the at least one patient speech pattern matching at least one characteristic speech pattern; and
    report with reporting circuitry a conclusion based on the determination of whether the patient has complied with the prescribed treatment regimen.

* * * * *